(12) United States Patent
DiBernardo et al.

(10) Patent No.: US 12,419,869 B2
(45) Date of Patent: Sep. 23, 2025

(54) METHODS OF TREATING MULTIPLE SCLEROSIS

(71) Applicants: Allitia DiBernardo, Philadelphia, PA (US); Tatiana Sidorenko, Allschwil (CH); Michel Burcklen, Allschwil (CH); Sivi Ouwerkerk-Mahadevan, Beerse (BE); Andrea Vaclavkova, Allschwil (CH); Brian Patrick Hennessy, Geneva (CH); Hilke Kracker, Weil am Rhein (DE)

(72) Inventors: Allitia DiBernardo, Philadelphia, PA (US); Tatiana Sidorenko, Allschwil (CH); Michel Burcklen, Allschwil (CH); Sivi Ouwerkerk-Mahadevan, Beerse (BE); Andrea Vaclavkova, Allschwil (CH); Brian Patrick Hennessy, Geneva (CH); Hilke Kracker, Weil am Rhein (DE)

(73) Assignee: Vanda Pharmaceuticals Inc., Washington, DC (US)

( * ) Notice: Subject to any disclaimer, the term of this patent is extended or adjusted under 35 U.S.C. 154(b) by 0 days.

(21) Appl. No.: 18/602,836

(22) Filed: Mar. 12, 2024

(65) Prior Publication Data

US 2024/0285590 A1 Aug. 29, 2024

Related U.S. Application Data

(63) Continuation of application No. 17/962,968, filed on Oct. 10, 2022, now Pat. No. 11,951,097.

(60) Provisional application No. 63/254,369, filed on Oct. 11, 2021.

(51) Int. Cl.
| | |
|---|---|
| *A61K 31/426* | (2006.01) |
| *A61K 9/00* | (2006.01) |
| *A61K 31/138* | (2006.01) |
| *A61P 25/28* | (2006.01) |

(52) U.S. Cl.
CPC ............ *A61K 31/426* (2013.01); *A61P 25/28* (2018.01); *A61K 9/0053* (2013.01); *A61K 31/138* (2013.01)

(58) Field of Classification Search
CPC ................ A61K 31/426; A61K 31/138; A61K 9/0053; A61P 25/38
See application file for complete search history.

(56) References Cited

U.S. PATENT DOCUMENTS

| | | | | |
|---|---|---|---|---|
| 4,284,786 A | * | 8/1981 | Kammerer | ............... A61P 37/08 514/916 |
| 4,959,389 A | * | 9/1990 | Speiser | ................ A61K 31/225 514/502 |
| 8,232,250 B2 | * | 7/2012 | Klinger | ................ A61K 31/785 514/17.9 |
| 10,220,023 B2 | | 3/2019 | Dingemanse | |

FOREIGN PATENT DOCUMENTS

| | | |
|---|---|---|
| EP | 0312697 A2 | 4/1989 |
| WO | 0030622 A2 | 6/2000 |
| WO | 2009115954 A1 | 9/2009 |
| WO | 2010022177 A2 | 2/2010 |
| WO | 2010046835 A1 | 4/2010 |
| WO | 2012061060 A1 | 5/2012 |
| WO | 2014152494 A1 | 9/2014 |
| WO | 20211176070 A1 | 9/2021 |

OTHER PUBLICATIONS

Olsson et al, Oral ponesimod in relapsing-remitting multiple sclerosis: a randomised phase II trial, J Neurol Neurosurg Psychiatry, 85, pp. 1198-1209. (Year: 2014).
Brossard et al. Multiple-Dose Tolerability, Pharmacokinetics, and of Ponesimod,and S1P1 Receptor Modulator: Favorable Impact of Doe Up-Titration. Journal of Clinical Pharmacology, vol. XX, No. XX, pp. 1-10. (Year: 2013).
LeBert et al., "Highly Functional Virus-Specific Cellular Immune Response in Asymptomatic SARS-CoV2 infection", J. Exp. Med., 2021, vol. 218, No. 5, e20202617, pp. 1-17.
Lott et al., "Modeling the Effect of the Selective S1P1 Receptor Modulator Ponesimod on Subsets of Blood Lymphocytes Pharmaceutical Research", 2017, 34(3), 599-609.
Lott et al., "Modeling Tolerance Development for the Effect on Heart Rate of the Selective S1P1 Receptor Modulator Ponesimod", Clin. Pharmacol. Ther., Jun. 2018, 103(6), 1083-1092, Epub Oct. 27, 2017.
Lott et al., "Impact of Demographics, Organ Impairment, Disease, Formulation, and Food on the Pharmacokinetics of the Selective SaP(1) Receptor Modulator Ponesimod Based on 13 Clinical Studies", Clin. Pharmacokinet., Apr. 2017, vol. 56(4), 395-408.
Lott et al., "Population pharmacokinetics of ponesimod and its primary metabolites in healthy and organ-impaired subjects", Eur. J. Pharm. Sci., Jun. 30, 2016, 89, 83-93, Epub Apr. 22, 2016.
Lublin FD, "Disease activity free status in MS", Mult Sler Relat Disord., Jan. 2012, 1(1), 6-7.
O'Connor et al., "Randomized Trial of Oral Teriflunomide for Relapsing Multiple Sclerosis", New England J. Med., 2011, 365, 1293-1230.
Olsson et al., "Correction: oral ponesimod in relapsing-remitting multiple sclerosis: a randomised phase II trial", J Neurol Neurosurg Psychiatry, 2019, vol. 90, pp. e7.

(Continued)

*Primary Examiner* — Sikarl A Witherspoon
(74) *Attorney, Agent, or Firm* — Hoffman Warnick LLC

(57) ABSTRACT

The disclosure relates to methods of treating multiple sclerosis. Also provided are pharmaceutical products containing ponesimod, instructions for use of ponesimod, methods for selling a drug product containing ponesimod, and methods for reducing clinical management events before or during treatment of multiple sclerosis.

8 Claims, 20 Drawing Sheets

(56) References Cited

OTHER PUBLICATIONS

Piali et al., "The selective sphingosine 1-phosphate receptor 1 agonist ponesimod protects against lymphocyte-mediated tissue inflammation", J. Pharmacol. Exp. Ther., May 2011, vol. 337(2), 547-556.

Polman et al., "Diagnostic criteria for multiple sclerosis: 2010 Revisions in the McDonald criteria", Ann. Neurol., 2011, 69(2), 292-302.

Pouzol et al., "Complete resolution of clinical signs and synergism of the combination ponesimod-dimethyl fumarate in rat models of multiple sclerosis". Encore poster presented at AAN, Apr. 1-27, 2018, Los Angeles, CA.

Pouzol et al., "Therapeutic Potential of Ponesimod Alone and in Combination with Dimethyl Fumarate in Experimental Models of Multiple Sclerosis", Innov. Clin. Neurosci., Mar. 1, 2019, 16(3-4), 22-30.

Pozzilli et al., "Maintenance of efficacy, safety and tolerability of ponesimod in patients with relapsing-remitting multiple sclerosis: phase II extension study", Poster presentation at ECTRIMS (2013) European Committee for Treatment & Research in Multiple Sclerosis—29th Congress.

Rey et al., "Desensitization by progressive up-titration prevents first-dose effects on the heart: guinea pig study with ponesimod, a selective S1P1 receptor modulator", PLoS One, Sep. 12, 2013, vol. 8, Issue 9, e74285.

Reyes et al., "Effects of Ethnicity and Sex on the Pharmacokinets and Pharmacodynamics of the Selective Spingosine-1-Phosphate Receptor 1 Modulator Ponesimod: A Clinical Study in Japanese and Caucasian Subjects", Pharmacology, Nov. 14, 2014, vol. 94 (5-6, 223-229.

Reyes et al., "Effects of ponesimod, a selective S1P1 reeptor modulator, on the pharamcokinetics of a hormonal combination contraceptive", Xenobiotica, Sep. 2014, 4, vol. 45, 1-11.

Reyes et al., "Mass balance, pharmacokinetics and metabolism of the seletive S1P receptor modulator ponesimodd in humans", Xenobiotica, Sep. 2014, 4, vol. 45, 1-11.

Scherz et al., "Three different up-titration regimens of ponesimod, an S1P1 receptor modulator, in healthy subjects", The Journal of Clinical Pharmacology, Jun. 2015, vol. 55(6), 688-697.

Sobel et al., "FTY720-P activates Sphingosine-1-phosphate receptor 2 and selectively couples to Ga12/13/Rho/ROCK to induce myofibroblast contraction", Mol. Pharmacol., Jun. 2015, vol. 87(6), 916-927.

Sobel et al., "Sphingosine 1-phosphate (S1P) receptor agonists mediate pro-fibrotic responses in normal human lung fibroblasts via S1P2 and S1P3 receptors and Smad-independent signaling", J. Biol. Chem. 2013, May 24, 2013, vol. 288(21), 14839-14851.

The Author(s), published by Elsevier Ltd., "Incidence of switching to second-line antiretroviral therapy and associated factors in children with HIV: an international cohort collaboration", vol. 6, Feb. 2019, e105-e115.

U.S National Library of Medicine: "Oral Ponesimod Versus Teriflunomide in Relapsing Multiple Sclerosis", Apr. 24, 2015, Retrieved from https://clinicaltrials.gov/ct2/show/study/NCT02425644.

Ufer et al., "Impact of siponmod on vaccination response in a randomized, placebo-controlled study", 2017, 1-9.

Vaclavkova et al., "Oral ponesimod in patients with chronic plaque psoriasis: a randomsed, double-blind, placebo-controlled phase 2 trial", Lancet, Dec. 6, 2014, vol. 384(9959), 2036-2045, Epub Aug. 10, 2014.

Wouters et al., "Pharmaceutical Salts and Co-crystals", RSC Publishing, 2012, pp. 1-9.

You et al., "Therapeutic use of a selective S1P1 receptor modulator ponesimod in autoimmune diabetes", PLoS One, Oct. 24, 2013, vol. 8(10): e77296.

Zhang et al., "Ponesimod protects against neuronal death by suppressing the activation of A1 astrocytes in early brain injury after experimental subarachnoid hemorrhage", J. Neurochem., Aug. 2021, 158(4), 880-897, doi: 10.111/jnc. 15457, Epub Jul. 16, 2021.

Achiron et al., "COVID-19 Vaccination in Patients with Multiple Sclerosis: What We have Learnt by Feb. 2021", Multiple Sclerosis Journal, Apr. 15, 2021, vol.27, No. 6, pp. 864-870.

Achrion et al., "Humoral Immune Response to COVID-19 mRNA Vaccine in Patients with Multiple Sclerosis Treated with High-Efficacy Disease-Modifying Therapies", Ther. Adv. Neurol. Disord., 2021, vol. 14, pp. 1-8.

D'Ambrosio et al., "Therapeutic Advances in Chronic Disease Ponesimod, a selective SIPI receptor modulator: a potential treatment for multiplee sclerosis and other immune-mediated diseases", Ther. Adv. Chronic Dis., Jan. 2016, vol. 7, No. 1, 18-33.

Anderson, "Teriflunomide Slows Brain Volume Loss in MS", Oct. 21, 2015, pp. 1-3.

Anonymous: "Managing you relapses", MS Society, retrieved from https://www.mssociety.org.uk/care-and-support/resources-and-publications/publications-search/managing-a-relapse-booklet, Nov. 2019, pp. 1-48.

Anonimous: "Package leaflet: Information for the patient—Ponesimod", retrieved from https://www.medicins.org.uk/emc/files/pil.12799.pdf, retrieved on Jan. 17, 2023, pp. 1-10.

Anonymous: "Ponesimod (Oral)", Retrieved from https://web.archive.org/web/20210913052832/https://www.drugs.com/cons/ponesimod.html, Dec. 24, 2020, pp. 1-14.

Anonymous: "Ponesimod—Anwendung, Wirkung, Nebenwirkungen I Gelbe Liste", Gelbe Liste, Retrieved from https://web.gelbe-liste.de/wirkstoffe/ Ponesimod_56402, Retrieved on Jan. 10, 2023, pp. 1-5.

Author unknown, "Barriers to paediatric switching to second-line ART", vol. 6, Feb. 2019, e71-e72.

Boehler et al., "Absolute Bioavailability of Ponesimod, a Selective S1P1 Receptor Modulator, in Healthy Male Subjects", European Journal of Drug Metabolism and Pharmacokinetics, 2017, vol. 42(1), 129-134.

Bolli et al., "2-imino-thiazolidin-4-one derivatives as potent, orally active S1P1 receptor agonists", J. Med. Chem., May 27, 2010, vol. 53(10), 4198-4211.

Brossard et al., "Pharmacokinetics and pharmacodynamics of ponesimod, a selective S1P1 receptor modulator, in the first-in-human study", Br. J. Clin. Pharmacol., Dec. 2013, 76(6), 888-896.

Cohen et al., "Mechanisms of fingolimod's efficacy and adverse effects in multiple sclerosis", Ann. Neurol., 2011, vol. 69(5), 759-777.

Cohen et al., "Oral fingolimod or intramuscular interferon for relapsing multiple sclerosis", N. Engl. J. Med., 2010, vol. 362(5), 402-415.

Confavreux et al., "Oral teriflunomideforpatients with relapsing multiple sclerosis (TOWER): a randomised, double-blind, placebo-controlled, phase 3 trial", Lancet Neurol., 2014, vol. 13, No. 3, pp. 247-256.

Confavreux et al., "Tower Trial Group Oral Teriflunomide for patients with relapsing multiple sclerosis (TOWER): a randomized double- blind, placebo-controlled, phase 3 trial", Lancet Neurol., Mar. 2014, 13(3), 247-256.

Cosman et al. High-Dose Glucocorticoids in Multiple Sclerosis Patients Exert Direct Effects on the Kidney and the Skeleton, Journal of Bone and Mineral Research, 7, p. 1097-1105. (Year: 1994).

D'Ambrosio et al., "Differential effects of ponesimod, a selective S1P1 receptor modulator, on blood-circulating human T cell Subpopulations", Immunopharmacol. Immunotoxicol., 2015, vol. 37(1), 103-109.

D'Ambrosio et al, "Ponesimod, a selective S1P1 receptor modulator: a potential treatment for multiple sclerosis and other immune-mediated diseases", Therapeutic Advances in Chronic Disease, vol. 7(1), 2016, 18-33.

De Stefano et al., "Establishing Pathological cut-offs of brain atrophy rates in multiple sclerosis", J. Neurol Neurosurg Psychiatry, 2016, vol. 87, pp. 93-99.

European Medines Agency, "Guidelines on clinical investigation of medicinal products for the treatment of Multiple Sclerosis", Mar.

(56) References Cited

OTHER PUBLICATIONS 26, 2015, EMA/CHMP/771815/2011, Rev. 2, Committee for Medicinal Products for Human Use (CHMP).
FDA, "Determining Whether to Submit an ANDA or a 505(b)(2) Application Guidance for Industry", U.S Department of Health and Human Services, Oct. 2017, pp. 1-14.
Freedman, Teriflunomide in relapsing multiple sclerosis: therapeutic utility, Therapeutic Advances in Chronic Disease, 4, 192-205. (Year: 2013).
Gatfield et al., "Sphingosine-1-Phosphate (S1P) Displays Sustained S1P Receptor Agonism and Signaling through S1P Lyase-dependent Receptor Recycling", Cell Signal., Jul. 2014, vol.. 26(7), 1576-1588.
Giorgio et al., "Cognition in multiple sclerosis: relevance of lesions, brain atrophy and proton MR spectroscopy," Neurol Sci, vol. 31, Issue: 2; 2010, pp. 245-248.
Guerard et al., "Effect of Hepatic or Renal Impairment on the Pharmacokinetics, Safety, and Tolerability of Ponesimod, a Selective S1P1 Receptor Modulator", Basic Clinic. Pharmacol. Toxicol., Article 2016, vol. 118, 356-368.
Handbook of Pharmaceutical Sals, Properties, Selection and Use, P. Heinrich Stahl, Camille G. Wermuth (Eds). Wiley-VCH, 2008 and Pharmaceutical Salts and Co-Crystals, Johan Wouters and Luc Quere (Eds.), RSC Publishing, 2012.
Havrdova et al., "Efficacy and safety of 2 doses of ponesimod (10 and 20 mg o.d.): Interim analysis of a phase II extension trial in relapsing-remitting multiple sclerosi", Oct. 2017—Poster presented; ECTRIMS Online Library, Oct. 27, 2017; Jun. 2008. Abstract No. P1151.
Havrdova et al., "Efficacy and safety of 2 doses of ponesimod (10 and 20 mg o.d.): Interim analysis of a Phase II extension trial in relapsing-remitting multiple sclerosis", Encore poster presented at AAN Apr. 21-27, 2018, Los Angeles, CA.
Hoch et al., "Clinical pharmacology of ponesimod, a selective S1P(1) receptor modulator, after up-titration to supratherapeutic doses in healthy subjects", Eur. J. Pharm. Sci., 2014, vol. 63, 147-153.
Hoch et al., "Effect of ponesimod, selective S1P1 receptor modulator, on the QT interval in healthy individuals", Basic Clin. Pharmacol. Toxicol., May 2015, vol. 116(5), 429-437.
Hudgens et al., "Development and Validation of the FSIQ-RMS: A New Patient-Reported questionnaire to Assess Symptoms and Impacts of Fatigue in Relapsing Multiple Sclerosis", Value Health, Apr. 2019, 22(4), 453-466.
Huwiler et al., "New players on the center stage: Sphingosine 1-phosphate and its receptors as drug targets", J. Biochem. Pharmacol. Review, 2008, vol. 75(10), 1893-1900.
Janssen Pharmaceutical Companies of Johnson & Johnson, "New Head-to-Head Phase 3 Study Data Show Ponesimod Superiority Versus Aubagio (teriflunomide) 14 mg in Adults with Relapsing Multiple Sclerosis (MS)", Sep. 11, 2019, pp. 1-6.
Janssen Pharmaceutical Companies, "PonvoryTM (ponesimod) tablets, for oral use", 2021, pp. 1-34.

Janssen Pharmaceutical Showcases Recent Data in Relapsing Multiple Sclerosis at the 2021 European Committee for Treatment and Research in Multiple Sclerosis Congress,CISION PR Newswire, retrieved from https://www.prnewswire.com/news-releases/janssen-showcases-recent-data-in-relapsing-multiple-sclerosis-at-the-2021-european-committee-for-treatment-and research-in-multiple-sclerosis-congress-301387378.html, Sep. 29, 2021, pp. 1-13.
Juif et al., "Mitigation of Initial Cardiodynamic Effets of the S1P1 Receptor Modulator Ponesimod Using a Novel Up-Titration Regimen", Journal of Clinical Pharamcology, 2016, vol. 57(3), 401-410.
Juif et al., "Clinical pharmacology, efficacy, and safety aspects of spingosine-1-phosphate receptor modulators", Expert Opin. Drug Metab. Toxicol., Aug. 2016, vol. 12(8), 879-895. Epub. Jun. 13, 2016.
Juif et al., "Biocomparison of three formulations of the S1P1 receptor modulator ponesimod in healthy subjects", Drugs in R&D., Jun. 2015, 15(2), 203-210.
Jurcevic et al., "Effects of multiple-dose ponesimod, a selective S1P(1) receptor modulator, on lymphocyte subsets in healthy humans", Drug Des. Devel. Ther., Dec. 28, 2016, vol. 11, 123-131.
Kappos et al., "A Placebo-Controlled Trial of Oral Fingolimod in Relapsing Multiple Sclerosis", N. Engl. J. Med., 2010, vol. 362(5), 37-401.
Kappos et al., "Effect of oral ponesimod on clinical disease activity and MRI-based outcomes in patients with relapsing multiple sclerosis: Phase 3 OPTIMUM study," Multiple sclerosis journal, vol. 26, 2020, pp. 151-152.
Kappos Ludwig et al, "Ponesimod Compared With Teriflunomide in Patients With Relapsing Multiple Sclerosis in the Active-Comparator Phase 3 OPTIMUM Study: A Randomized Clinical Trial", JAMA Neurology, US, (Mar. 29, 2021), vol. 78, No. 5, doi:10.1001/jamaneurol.2021.0405, ISSN 2168-6149, pp. 558-567, XP055806282.
Kappos et al., "The POINT study: a randomized, double-blind, parallel-group, add on, superiority phase 3 study to compare the efficcy and safety of ponesimod to placebo in subjects with active relapsing multiple sclerosis who are treated with dimethyl fumarate", Poster presented at ECTRIMS (European Committee for Treatment and Research in Multiple Sclerosis), Citation for abstract: ECTRIMS Oline Library, Oct. 10, 2018, 228412. Abstract No. P568.
Kappos et al., "Oral fingolimod (FTY720) for relapsing multiple sclerosis", N. Engl. J. Med., 2006, 355(11), 1124-1140.
Keown, "Janssen's Ponesimod Finds Success in Head-to-Head Multiple Sclerosis Trial", Jul. 26, 2019, pp. 1-4.
Kihara et al., "Ponesimod inhibits astrocyte-mediated neuroinflammation and protects against cingulum demyelination via S1P1-selective modulation," SAGE Publications Abstracts Multiple Sclerosis Journal, Oct. 1, 2021, 1-13.
Krause et al., "Modeling clinical efficacy of the S1P receptor modulator ponesimod in psoriasis", J. Dermatol. Sci., Feb. 2018, vol. 89(2), 136-145, Epub Nov. 20, 2017.
Krause et al., "Population pharmacokinetics and pharmacodynamics of ponesimod, a selective S1P1 receptor modulator", J. Pharmacokinet. Pharmacodyn., Jun. 2014, vol. 41(3), 261-278.

\* cited by examiner

METHODS OF TREATING MULTIPLE SCLEROSIS

CROSS-REFERENCE TO RELATED APPLICATIONS

This application is a continuation of U.S. patent application Ser. No. 17/962,968, filed Oct. 10, 2022, which claims the benefit of U.S. Provisional Patent Application No. 63/254,369, filed Oct. 11, 2021, all of which are incorporated by reference herein.

TECHNICAL FIELD

The present disclosure relates to methods of treating multiple sclerosis.

BACKGROUND

Multiple sclerosis (MS) is a chronic autoimmune inflammatory disease of the central nervous system affecting approximately 2.5 million people worldwide. The disease is clinically perceived by relapses and progressive loss of neurological function, primarily attributed to demyelination, axonal loss, and gliosis culminating in long-term multifocal sclerotic plaques in the brain and spinal cord leading to neurological impairment and severe disability. The two main subtypes of MS are relapsing forms of MS (RMS) which represent 85% of MS patients and include relapsing-remitting disease (RRMS), clinically isolated syndrome, and active secondary progressive disease; and primary progressive MS (PPMS) which affects only 15% of MS patients.

Relapses are defined as newly appearing neurological symptoms in the absence of fever or infections that last for more than 24 hours. Relapses may fully recover over days or weeks or lead to persistent residual deficits and accumulation of disability.

The natural history of MS is usually divided into two partially overlapping phases, a predominantly inflammatory phase and a predominantly degenerative phase: after an initial phase of relapsing remitting MS, driven by inflammatory mechanism, patients experience a secondary progressive MS characterized by continuous worsening of symptoms independent of the occurrence of relapses, the degenerative phase of MS. Most currently available disease-modifying treatments (DMTs) address the inflammatory phase of MS and are less efficacious in the degenerative phase.

Current medical practice encourages early intervention with disease-modifying treatments, with the intent of optimizing long-term clinical outcomes.

Key objectives in the management of MS are reducing the rate of relapses and preventing or at least delaying disease progression. Most of the disease-modifying drugs approved for MS have to be administered by injection or infusion (subcutaneous [s.c.], intramuscular [i.m.], or intravenous [i.v.] route). Recently, new disease-modifying drugs administered orally have been approved for RMS.

The following injectable drugs have been approved in at least one country for the treatment of MS:
  Interferon (IFN) β-1a 30 mcg i.m. once weekly (Avonex®)
  IFN β-1a 22 or 44 mcg s.c. 3 times weekly (Rebif®)
  IFN β-1b 250 mcg s.c. every other day (Betaferon®, Extavia®)
  Pegylated IFN β-1a 125 mcg subcutaneously every 2 weeks (Plegridy®)
  Glatiramer acetate 20 mg s.c. once a day (o.d.) or 40 mg subcutaneously 3 times weekly (Copaxone®)
  Glatiramer acetate 20 mg s.c. o.d. (Glatopa®)
  Natalizumab 300 mg i.v. every 4 weeks (Tysabri®)
  Mitoxantrone i.v. every 3 months (Novantrone®)
  Alemtuzumab concentrate for solution for infusion, 12 mg alemtuzumab in 1.2 mL (10 mg/mL) (Lemtrada®)

Several oral drugs have also been approved for MS:
  Fingolimod 0.5 mg orally o.d. (Gilenya®)
  Teriflunomide 7 mg, 14 mg o.d. (Aubagio®)
  Dimethyl fumarate (BG-12) gastro-resistant hard capsules 120/240 mg twice daily (Tecfidera®)
  Cladribine 40 to 100 mg orally per treatment week (Mavenclad®)

Sphingosine-1-phosphate (SIP) plays a central role in lymphocyte trafficking. SIP is synthesized and secreted by many cell types, including platelets, erythrocytes, and mast cells, and elicits a variety of physiological responses. Lymphocyte egress from primary and secondary lymphoid organs is dependent on the S1P1 receptor. S1P1 receptor modulators block lymphocyte migration out of lymphoid tissue into the lymphatic and vascular circulation, thereby reducing peripheral lymphocyte counts and preventing lymphocyte recruitment to sites of inflammation. Following withdrawal of an S1P1 receptor agonist, the functional lymphocytes return to the circulation from their sites of sequestration. Other functions that do not rely on homing mechanisms, such as antibody generation by B lymphocytes, first-line immunological protection by granulocytes and monocytes, and antigen-dependent T-cell activation and expansion, are not affected by this mechanism.

SIP itself induces pleiotropic effects, which are mediated by a family of five G protein-coupled receptors, S1P1-S1P5, located on endothelial cells, vascular and cardiac smooth muscle cells, and cardiac myocytes. The first S1P receptor modulator, fingolimod (FTY720, Gilenya®), which has been approved by the FDA and the EMA for the treatment of MS, is not selective for the S1P1 receptor but interacts with S1P3, S1P4, and S1P5.

Ponesimod, an iminothiazolidinone derivative, is an orally active, selective modulator of the S1P1 that induces a rapid, dose-dependent, and reversible reduction in peripheral blood lymphocyte count by blocking the egress of lymphocytes from lymphoid organs. T and B cells are most sensitive to ponesimod mediated sequestration. In contrast, monocyte, natural killer (NK) cell and neutrophil counts are not reduced by ponesimod. Ponesimod is commercially available as PONVORY™, a once-daily oral medication. In the United States the Food and Drug Administration (FDA) has approved PONVORY™ to treat adults with relapsing forms of multiple sclerosis (MS), to include clinically isolated syndrome, relapsing-remitting disease, and active secondary progressive disease.

In the pharmaceutical industry, the path from drug discovery to reaching an approved product is riddled with uncertainty. That path is one that since 2010 and out of more than 12,000 clinical studies, there is very low likelihood of regulatory approval of less than 10% (from Phase 1 to approval). The final path to approval is also not a certainty nor inevitable as failures continue as late as from Phase 3 to approval. This is not only due to the high unpredictability and uncertainty regarding how a pharmaceutical product will impact human biology, but often human behavior is unpredictable in how data is interpreted by regulatory agencies and whether the data warrants approving a study drug as an approved product for use in commerce.

SUMMARY

The disclosure relates to a pharmaceutical product comprising ponesimod, wherein the pharmaceutical product is packaged, and wherein the package includes a label that identifies ponesimod as an approved product for the treatment of multiple sclerosis. In some embodiments, the patient's multiple sclerosis is relapsing multiple sclerosis. In other embodiments, the relapsing multiple sclerosis comprises relapsing-remitting disease, clinically isolated syndrome, or active secondary progressive disease.

The disclosure provides methods for treating multiple sclerosis in a patient in need thereof, comprising administering an approved product comprising ponesimod in an amount and manner that is described in a drug product label for the approved product and/or in a treatment regimen described herein.

The disclosure also provides methods of selling an approved product comprising ponesimod, said method comprising selling such drug product, wherein a drug product label for a reference listed drug for such drug product includes instructions for treating a patient with multiple sclerosis.

The disclosure further provides methods of offering for sale a drug product comprising ponesimod, said method comprising offering for sale such drug product, wherein a drug product label for a reference listed drug for such drug product includes instructions for treating a patient with multiple sclerosis.

The disclosure further provides methods for reducing clinical management events and/or for easing use of drug treatment for treating multiple sclerosis in a patient in need thereof, comprising administering ponesimod in an amount and manner that is described in a drug product label for an approved product and/or in a treatment regimen described herein, namely administration of about 20 mg of ponesimod orally once daily, with or without utilization of the up-titration dosing procedure also described herein.

The disclosure is also directed to an approved drug product as defined herein, wherein the pharmaceutical product comprises ponesimod in tablet form.

The disclosure also provides methods for concomitant treatment of a beta-blocker and ponesimod in a patient in need thereof, wherein the patient is being treated with the beta-blocker and ponesimod treatment is to be initiated, and wherein the patient has a resting heart rate of greater than 55 beats per minute during treatment with the beta-block and prior to initiation of ponesimod, comprising administering ponesimod without interruption to the beta-blocker treatment.

In other embodiments, the disclosure is directed to methods for concomitant treatment of a beta-blocker and ponesimod for a patient in need thereof, wherein the patient is being treated with the beta-blocker and ponesimod treatment is to be initiated, and wherein the patient has a resting heart rate of less than or equal to 55 beats per minute during treatment with the beta-block and prior to initiation of ponesimod, comprising interrupting the beta-blocker treatment until the patient's heart rate is greater than 55 beats per minute and initiating ponesimod treatment in a titration regimen comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; and 10 mg of ponesimod on days 12, 13, and 14, followed by administering a 20 mg maintenance dose of ponesimod once daily thereafter, and reinitiating the beta-blocker after ponesimod has been up-titrated to the maintenance dosage.

The disclosure also relates to methods of treating multiple sclerosis in a patient in need thereof, wherein the patient has sinus bradycardia, first or second degree AV block, or a history of myocardial infarction or heart failure occurring more than 6 months prior to the initiation of ponesimod treatment, comprising administering an effective regimen of ponesimod to the patient, wherein after a first dose of the ponesimod, the patient is monitored for a period of 4 hours for symptoms of bradycardia. In other embodiments, no first dose monitoring is needed wherein the patient has no sinus bradycardia, no first or second degree AV block, and no history of myocardial infarction or heart failure occurring more than 6 months prior to the initiation of ponesimod treatment.

The disclosure further provides methods of reinitiating treatment with ponesimod following a missed dose in a patient in need thereof, wherein the patient is being treated with an oral, once daily 20 mg maintenance dose and fewer than four consecutive maintenance doses have been missed, comprising resuming treatment with the maintenance dose.

In other embodiments, the disclosure is directed to methods of reinitiating ponesimod following a missed dose for a patient in need thereof, wherein the patient is being treated with an oral, once daily 20 mg maintenance dose or a 14-day titration regimen comprising administering orally once daily titration doses of 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; and 10 mg of ponesimod on days 12, 13, and 14, and four or more consecutive maintenance doses or titration doses have been missed, comprising reinitiating ponesimod with the 14-day titration regimen.

BRIEF DESCRIPTION OF THE DRAWINGS

In FIG. 2A, n(Pon)=No. of subjects in ponesimod arm; rate (Pon)=mean rate in ponesimod arm; n(Ter)=No. of subjects in teriflunomide arm; and rate(Ter)=mean rate in teriflunomide arm. *=Conducted on the Per Protocol Set; **=Relapses with missing EDSS are imputed as confirmed relapses.

In FIG. 3A, subjects with available baseline and at least one post-baseline result are included in the analysis, whereby MMRM=mixed effects repeated measurements model with unstructured covariance, treatment, visit, treatment by visit interaction, baseline by visit interaction as fixed effects, baseline FSIQ score, EDSS strata (<=3.5,>3.5), DMT in last 2 years prior randomization strata (Y,N) as covariates.

In FIG. 4, an event=12 week CDA and subjects without event are censored at their last EDSS assessment without EDSS increase. Unstratified Kaplan-Meier estimates are presented. Bars on graph display pointwise 95% confidence intervals of the estimate. P-value is two-sided and based on the stratified log-rank test. Hazard ratio estimate obtained from stratified Cox regression with Wald confidence limits. Analysis is stratified by EDSS strata (≤3.5; >3.5) and disease modifying therapy in last 2 years prior to randomization strata (Y,N).

In FIG. 5, an event=24 week CDA and subjects without event are censored at their last EDSS assessment without EDSS increase. Unstratified Kaplan-Meier estimates are presented. Bars on graph display pointwise 95% confidence intervals of the estimate. P-value is two-sided and based on the stratified log-rank test. Hazard ratio estimate obtained from stratified Cox regression with Wald confidence limits. Analysis is stratified by EDSS strata (≤3.5; >3.5) and disease modifying therapy in last 2 years prior to randomization strata (Y,N).

In FIG. 7, n(Pon)=subjects in ponesimod group; rate(Pon)=annualized relapse rate in ponesimod group; n(Ter)=subjects in teriflunomide group and rate(Ter)=annualized relapse rate in teriflunomide group. The vertical solid line references the treatment effect from the main analysis. Negative binomial model is applied with Wald confidence limits, offset: log time (years) up to EOS. The main analysis is adjusted for the following covariates: EDSS strata (≤3.5; >3.5); DMT in last 2 years prior to randomization strata (Y,N); and number of relapses in year prior to study entry (≤1; ≥2).

In FIG. 8, p*=interaction p-value; n(Pon)=no. of subjects in ponesimod group; rate(Pon)=mean rate in ponesimod group; n(Ter)=no. of subjects in teriflunomide group and rate(Ter)=mean rate in teriflunomide group. Negative binomial model is applied with Wald confidence limits, offset: log time (years) up to EOS, in each subgroup separately. Interaction p-value is from likelihood ratio test of interaction term in model with treatment, subgroup and treatment by subgroup interactions. The vertical solid line references the treatment effect from the main analysis. The main analysis is adjusted for the following covariates: EDSS strata (≤3.5; >3.5); DMT in last 2 years prior to randomization strata (Y,N); and number of relapses in year prior to study entry (≤1; ≥2). Analyses in subgroups are not adjusted for covariates.

DETAILED DESCRIPTION OF ILLUSTRATIVE EMBODIMENTS

Figure 1:
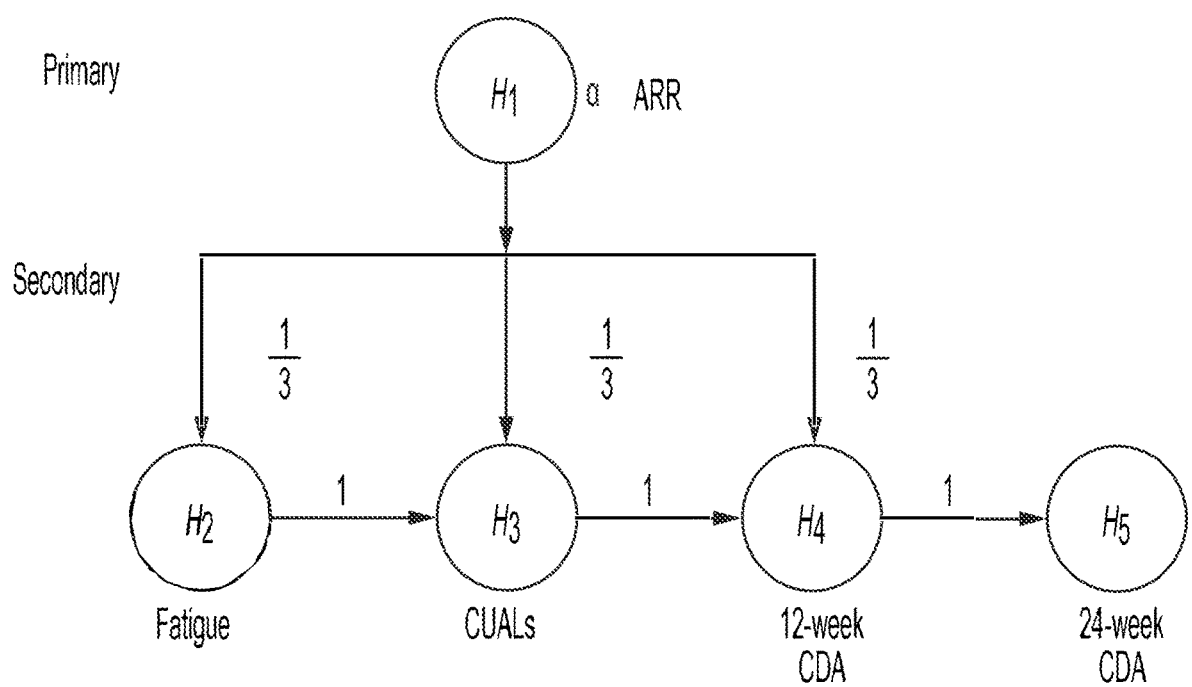
FIG. 1 shows the testing strategy for the study described in Example 1.

In the present disclosure the singular forms "a", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the disclosure which are, for clarity, described herein in the context of separate embodiments, may also be provided in combination in a single embodiment. That is, unless obviously incompatible or excluded, each individual embodiment is deemed to be combinable with any other embodiments and such a combination is considered to be another embodiment. Conversely, various features of the disclosure that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

In some aspects, the present disclosure is directed to methods of avoiding worsening of fatigue-related symptoms in a human patient suffering from multiple sclerosis and fatigue, comprising, optionally, assessing the fatigue-related symptoms of the patient; and administering an effective regimen of ponesimod to the patient, wherein the regimen is sufficient to avoid worsening of the fatigue-related symptoms. As described herein, fatigue is fatigue associated with multiple sclerosis.

In certain aspects, the methods are directed to patients that have had no prior disease modifying treatment (DMT) for multiple sclerosis within about two years prior to initiation of treatment with ponesimod. In some embodiments, the methods are directed to patients that have a baseline expanded disability status scale (EDSS) score of ≤3.5 prior to initiation of treatment with ponesimod. In other embodiments, the methods are directed to patients that have no Gd+/T1 lesions prior to initiation of treatment with ponesimod. Baseline refers to a time period prior to initiation of treatment with ponesimod and/or standard of care treatment. This time period is typically up to about 45 days prior to initiation of treatment, including, for example, up to about 40 days, up to about 35 days, up to about 30 days, up to about 25 days, up to about 20 days, up to about 15 days, or up to about 10 days prior to initiation of treatment with ponesimod and/or standard of care treatment.

In other aspects, the present disclosure is directed to methods of reducing the number of combined unique active lesions (CUALs) in a patient suffering from multiple sclerosis, comprising administering an effective regimen of ponesimod to the patient, wherein the regimen is sufficient to reduce the number of CUALs by at least 40% relative to a patient population at substantially the same level of disease progression receiving a standard of care treatment that does not comprise ponesimod.

In some aspects, the methods of the disclosure are performed on a human patient suffering from multiple sclerosis. In some embodiments, the patient's multiple sclerosis is relapsing multiple sclerosis. In other embodiments, the relapsing multiple sclerosis comprises relapsing-remitting disease, clinically isolated syndrome, or active secondary progressive disease.

As used herein, the term "avoiding worsening of fatigue-related symptoms" refers to preventing the patient's fatigue-related symptoms from becoming worse relative to the patient's fatigue-related symptoms at baseline, wherein baseline refers to a time period prior to initiation of treatment with ponesimod. This time period is typically up to about 45 days prior to initiation of treatment with ponesimod, including, for example, up to about 40 days, up to about 35 days, up to about 30 days, up to about 25 days, up to about 20 days, up to about 15 days, or up to about 10 days prior to initiation of treatment with ponesimod. By avoiding worsening, the methods otherwise relate to stabilizing or improving fatigue-related symptoms.

In some embodiments of the methods of the disclosure, the patient's fatigue-related symptoms are assessed. In some embodiments of the methods of the disclosure, the patient's fatigue-related symptoms are not assessed prior to initiation of treatment with ponesimod. As used herein, "fatigue-related symptoms" refer to symptoms of fatigue experienced by the patient.

In some aspects, the fatigue-related symptoms are symptoms experienced by the patient while doing routine daily activities (e.g. housework, yard work, shopping, working). In some embodiments, the fatigue-related symptoms are those experienced by the patient while doing routine daily activities and include being physically tired, being mentally tired, being physically weak, lacking energy, feeling worn out, or feeling sleepy.

In other embodiments, the fatigue-related symptoms are (1) being physically tired, (2) being mentally tired, (3) being physically weak, (4) lacking energy, (5) feeling worn out, (6) feeling sleepy while doing routine daily activities, and (7) feeling worn out while at rest.

In some embodiments, the patient's fatigue-related symptoms are assessed before initiation of ponesimod administration, for example, at baseline. In other embodiments, the patient's fatigue-related symptoms are assessed after initiation of ponesimod administration to, for example monitor the fatigue-related symptoms during the treatment with ponesimod. In some embodiments, the patient's fatigue-related symptoms are assessed both before initiation of ponesimod administration and after initiation of ponesimod therapy.

The patient's fatigue-related symptoms may be assessed by ascertaining from the patient the nature and severity of any symptoms of fatigue experienced by the patient. In some embodiments, the patient's fatigue-related symptoms are assessed using a patient-reported outcome (PRO) questionnaire.

Figure 2A:
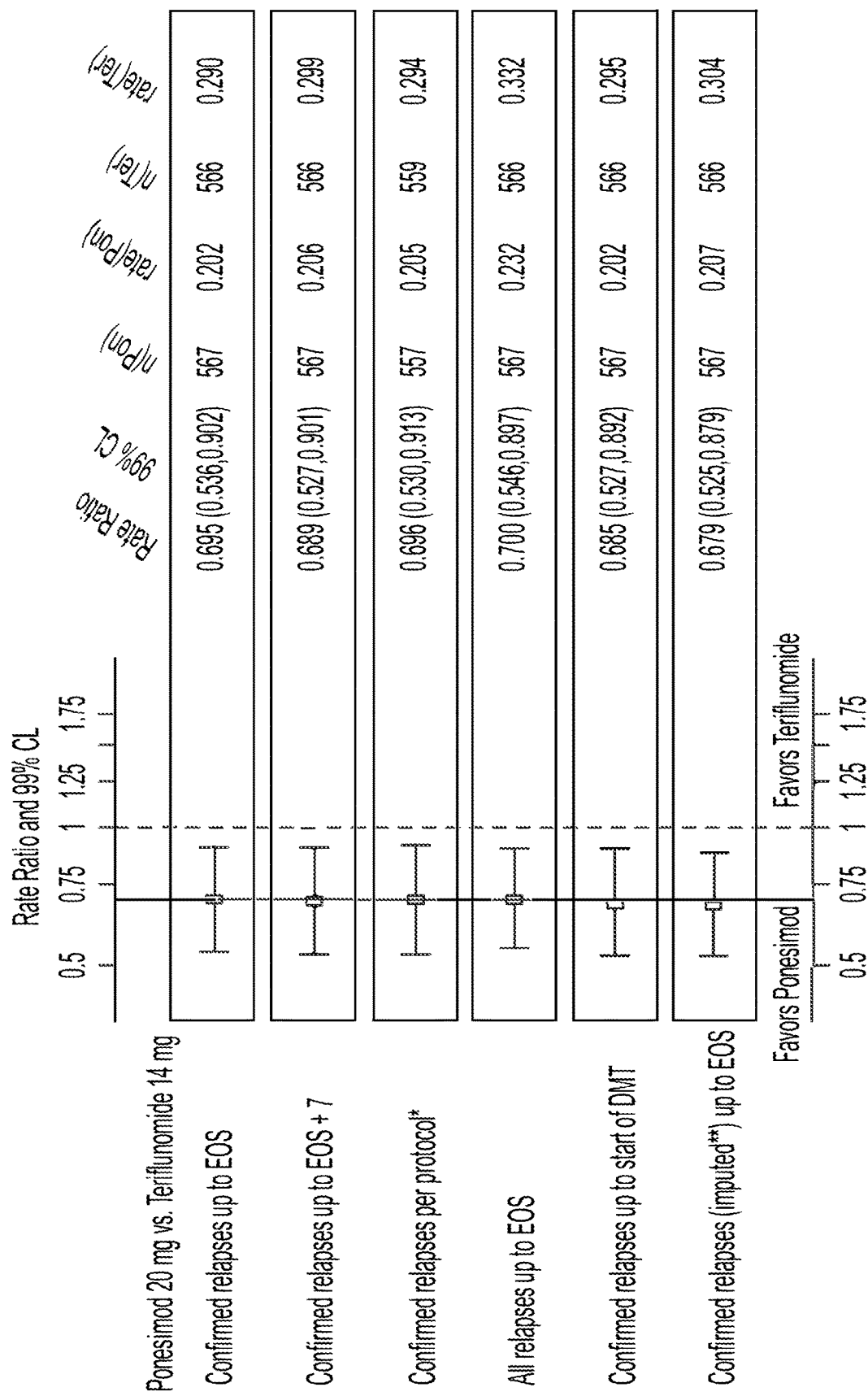
FIG. 2A shows an overview of primary and main supplementary analyses of relapses (Forest plot with 99% CL).
Figure 2B:
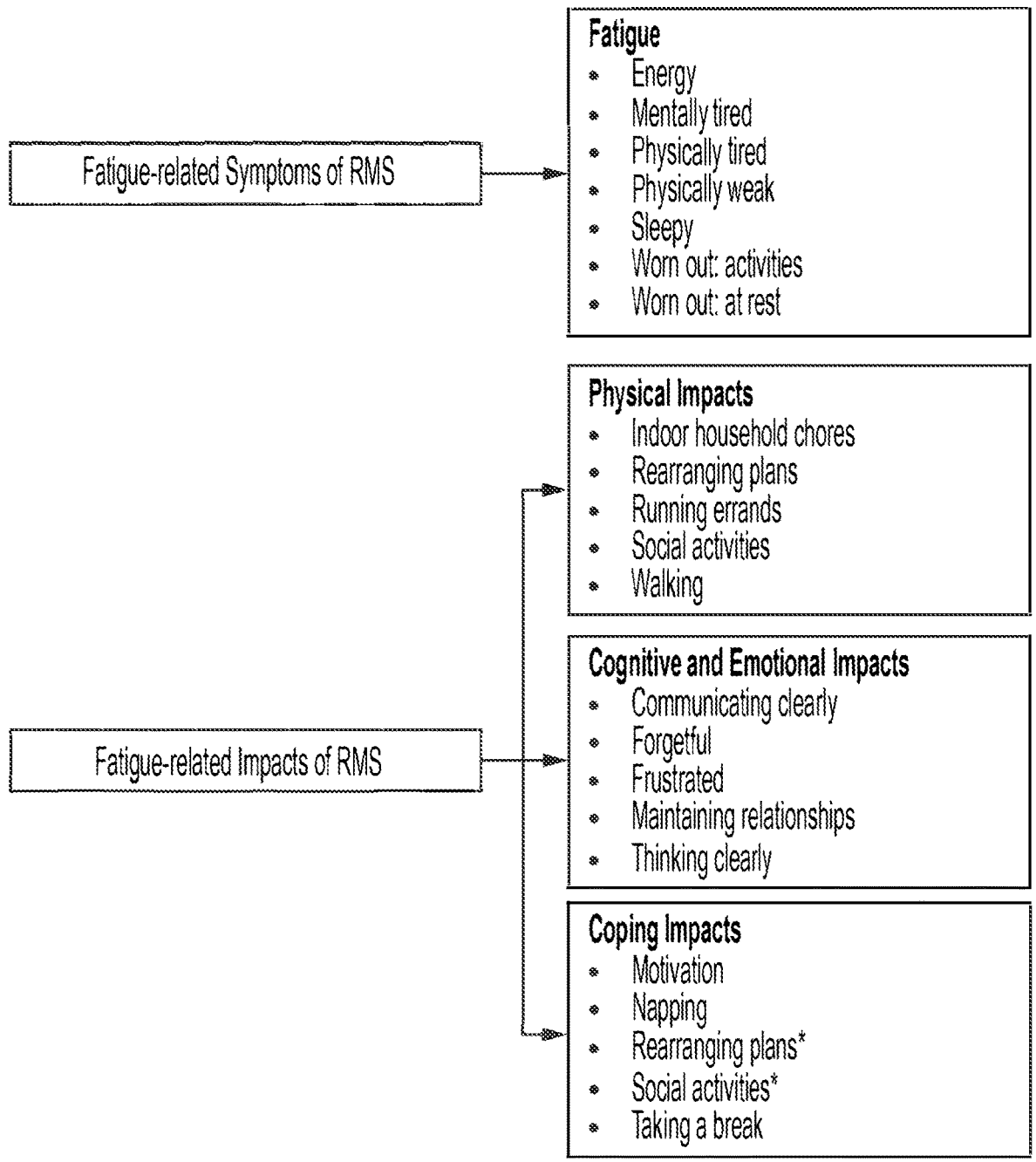
FIG. 2B shows the conceptual framework for the Fatigue Symptoms and Impact Questionnaire—Relapsed Multiple Sclerosis (FSIQ-RMS); *=items also present in physical impacts subdomain.

In some embodiments, the patient-reported outcome questionnaire is the Fatigue Symptoms and Impact Questionnaire—Relapsing Multiple Sclerosis (FSIQ-RMS) (available from Mapi Research Trust). The FSIQ-RMS is an MS specific 20-item PRO measure that comprises 2 domains: one measuring MS symptoms and one measuring MS-related impacts. See Hudgens S, et al., *Development and Validation of the FSIQ-RMS: A New Patient-Reported Questionnaire to Assess Symptoms and Impacts of Fatigue in Relapsing Multiple Sclerosis. Value Health.* 2019 April; 22(4):453-466. doi: 10.1016/j.jval.2018.11.007. Epub 2019 Feb. 21. PubMed PMID: 30975397. With 7 symptom items and 13 impact items (in 3 impacts subdomains: physical, cognitive and emotional, and coping), the FSIQ-RMS is a comprehensive, valid, and reliable measure of fatigue-related symptoms and impacts in RMS patients. FIG. 2B depicts a conceptual framework for the FSIQ-RMS.

In some embodiments, the patient-reported outcome questionnaire is the symptom domain of the FSIQ-RMS. The FSIQ-RMS symptom domain (FSIQ-RMS-S) consists of seven items assessing fatigue-related symptoms with a recall period of 24 hours measured on an 11-point numeric rating scale; the standardized symptom domain score ranges from 0 to 100 with a higher score indicating greater fatigue. This domain (i.e., section 1 of the questionnaire) is completed on 7 consecutive days.

The FSIQ-RMS impact domain (FSIQ-RMS-I) consists of 13 items assessing impacts of fatigue-related symptoms with a recall period of 7 days measured on a 5-point verbal descriptor scale, the standardized impact domain score ranges from 0 to 100 with a higher score indicating greater impact.

In some aspects of the methods of the present disclosure, the patient is administered an effective regimen of ponesimod. An effective regimen is one that elicits the biological or medicinal response in a human tissue system that is being sought by a researcher, medical doctor, or other clinician, which includes alleviation of one or more symptoms of the disease or disorder being treated.

As used herein, the term "ponesimod" refers to the compound (R)-5-[3-chloro-4-(2,3-dihydroxy-propoxy)-benz[Z]ylidene]-2-([Z]-propylimino)-3-o-tolyl-thiazolidin-4-one, which has the following structure:

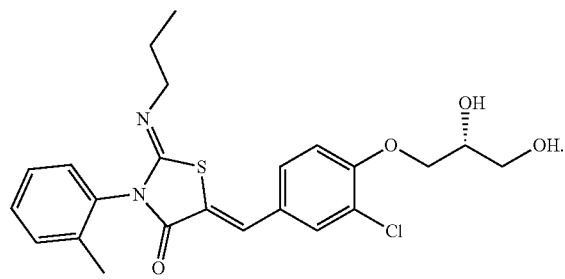 [SMILES: CCC/N=C1\S/C(=C\c2ccc(OC[C@H](O)CO)c(Cl)c2)C(=O)N1c1ccccc1C]

In some embodiments, "ponesimod" also refers to pharmaceutically acceptable salts of ponesimod. The term "pharmaceutically acceptable salt" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example Handbook of Pharmaceutical Salts. Properties, Selection and Use, P. Heinrich Stahl, Camille G. Wermuth (Eds.), Wiley-VCH, 2008 and Pharmaceutical Salts and Co-crystals, Johan Wouters and Luc Quéré (Eds.), RSC Publishing, 2012.

It is to be understood that the present disclosure encompasses ponesimod in any form including amorphous as well as crystalline forms. It is further to be understood that crystalline forms of ponesimod encompasses all types of crystalline forms including polymorphs, solvates and hydrates, salts and co-crystals (when the same molecule can be co-crystallized with different co-crystal formers) provided they are suitable for pharmaceutical administration. In some embodiments, ponesimod is in crystalline form A or crystalline form C as described in WO 2010/046835, incorporated herein by reference. In some embodiments, ponesimod is in crystalline form C.

It should be noted that the amounts of ponesimod described herein are set forth on a ponesimod free base basis. That is, the amounts indicate that amount of the ponesimod molecule administered, exclusive of, for example, solvent (such as in solvates) or counterions (such as in pharmaceutically acceptable salts).

In some embodiments, the effective regimen comprises a daily dose of ponesimod. In some embodiments, the daily dose of ponesimod is administered orally.

In some embodiments, the daily dose of ponesimod is administered once daily.

In some embodiments, the daily dose of ponesimod is about 15 to about 25 mg. In further embodiments, the daily dose of ponesimod is about 15 mg, about 16 mg, about 17 mg, about 18 mg, about 19 mg, about 20 mg, about 21 mg, about 22 mg, about 23 mg, about 24 mg, or about 25 mg. In certain embodiments, the daily dose of ponesimod is about 20 mg.

In some embodiments, about 20 mg of ponesimod is administered orally once daily.

In other embodiments, the effective regimen comprises an up-titration, followed by a daily maintenance dose of ponesimod. An up-titration is a dosing procedure in which the daily dose of ponesimod is gradually increased over a period of days, culminating with administration of the maintenance dose.

In some embodiments, the regimen comprises an up-titration at the initiation of the method of the disclosure. In other embodiments, the regimen comprises an up-titration upon re-initiation of the method after a discontinuation of the method of the disclosure. As used herein, "upon re-initiation of the method after a discontinuation" means an interruption of the administration of ponesimod of at least one, at least two or preferably at least 3 days before treatment is re-initiated. In some embodiments, the regimen comprises an up-titration step at initiation of the method or upon re-initiation of the method after a discontinuation.

In some embodiments of the methods of the disclosure, the up-titration regimen one disclosed in U.S. Pat. No. 10,220,023, incorporated herein by reference. For example, in certain aspects, the up-titration comprises administering orally once daily about 2 mg of ponesimod on days 1 and 2; about 3 mg of ponesimod on days 3 and 4; about 4 mg of ponesimod on days 5 and 6; about 5 mg of ponesimod on day 7; about 6 mg of ponesimod on day 8; about 7 mg of ponesimod on day 9; about 8 mg of ponesimod on day 10; about 9 mg of ponesimod on day 11; and about 10 mg of ponesimod on days 12, 13, and 14.

In other embodiments of the methods of the disclosure, the up-titration comprises administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; and 10 mg of ponesimod on days 12, 13, and 14.

In some embodiments, the maintenance dose is about 20 mg of ponesimod once daily.

In some embodiments, the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by the administering of the 20 mg of ponesimod once daily thereafter.

In some aspects of the disclosed methods, the regimen is sufficient to avoid worsening of the fatigue-related symptoms. A regimen is sufficient to avoid worsening of the fatigue-related symptoms when the patient's fatigue-related symptoms (assessed as described herein) after administration of the ponesimod regimen, are either improved or unchanged compared to the patient's fatigue-related symptoms (assessed as described herein) prior to administration of the ponesimod regimen, for example, at baseline.

In other embodiments, the methods of the disclosure are directed to reducing the number of combined unique active lesions (CUALs) in a patient.

CUALs are new Gd+T1 lesions plus new or enlarging T2 lesions (without double-counting of lesions). The cumulative number of CUAL is considered a reliable outcome measure of inflammatory MS disease activity. Radiological evidence of disease activity is routinely used to support disease diagnosis and to inform therapeutic decisions targeting no evidence of disease activity (NEDA), clinical (relapses or disability accumulation) or radiological (brain lesions on MRI) perspective. See Lublin F D. *Disease activity free status in MS.* Mult Scler Relat Disord. 2012 January; 1(1):6-7. doi: 10.1016/j.msard.2011.08.001. Epub 2011 Aug. 27. PubMed PMID: 25876444.

CUALs are detected using magnetic resonance imaging (MRI) techniques.

In this aspect of the disclosed methods, the ponesimod regimen administered to the patient is sufficient to reduce the number of CUALs by at least 40% relative to a patient population at substantially the same level of disease progression receiving a standard of care treatment. That is, the patient administered the ponesimod regimen will have acquired at least 40% fewer CUALs as compared to a patient having substantially the same degree of MS progression who is receiving a standard of care treatment.

In some embodiments, the ponesimod regimen administered to the patient is sufficient to reduce the number of CUALs by at least 20% to about 65% relative to a patient population at substantially the same level of disease progression receiving a standard of care treatment. In some embodiments, the ponesimod regimen administered to the patient is sufficient to reduce the number of CUALs by at least 30% relative to a patient population at substantially the same level of disease progression receiving a standard of care treatment. In some embodiments, the ponesimod regimen administered to the patient is sufficient to reduce the number of CUALs by at least 50% relative to a patient population at substantially the same level of disease progression receiving a standard of care treatment. In some embodiments, the ponesimod regimen administered to the patient is sufficient to reduce the number of CUALs by at least 55% relative to a patient population at substantially the same level of disease progression receiving a standard of care treatment.

As used herein, the term "standard of care treatment" refers to a physician-prescribed treatment of MS. In some embodiments, the standard of care comprises, consists of, or consists essentially of administering an MS treatment that has been approved by a regulatory authority. In some embodiments, the standard of care treatment is Interferon (IFN) β-1a 30 mcg i.m. once weekly (Avonex®), IFN β-1a 22 or 44 mcg s.c. 3 times weekly (Rebif®), IFN β-1b 250 mcg s.c. every other day (Betaferon®, Extavia®), Pegylated IFN β-1a 125 mcg subcutaneously every 2 weeks (Plegridy®), Glatiramer acetate 20 mg s.c. once a day (o.d.) or 40 mg subcutaneously 3 times weekly (Copaxone®), Glatiramer acetate 20 mg s.c. o.d. (Glatopa®), Natalizumab 300 mg i.v. every 4 weeks (Tysabri®), Mitoxantrone i.v. every 3 months (Novantrone®), Alemtuzumab concentrate for solution for infusion, 12 mg alemtuzumab in 1.2 mL (10 mg/mL) (Lemtrada®), Fingolimod 0.5 mg orally o.d. (Gilenya®), Teriflunomide 7 mg, 14 mg o.d. (Aubagio®), Dimethyl fumarate (BG-12) gastro-resistant hard capsules 120/240 mg twice daily (Tecfidera®), or Cladribine 40 to 100 mg orally per treatment week (Mavenclad®).

In some embodiments, the standard of care treatment comprises a S1P receptor modulator that is not ponesimod.

In other embodiments, the standard of care treatment comprises teriflunomide. In some embodiments, the standard of care treatment comprises administration of about 14 mg of teriflunomide orally once daily.

In some embodiments, the patient has had no prior disease modifying treatment (DMT) for multiple sclerosis. In some embodiments, the patient has had no prior disease modifying treatment (DMT) for multiple sclerosis within about two years prior to initiation of treatment with ponesimod. In some embodiments, patients that have had no prior DMT for multiple sclerosis realize improved efficacy from use of ponesimod to address fatigue with respect to a standard of care treatment that does not comprise ponesimod, such as teriflunomide. Accordingly, with respect to these patients and others, the disclosed methods provide health care providers with options for improved outcomes compared to standard of care.

In some embodiments, the methods are directed to patients having a baseline expanded disability status scale (EDSS) score of ≤3.5. In some embodiments, the methods are directed to patients having no Gd+/T1 lesions at baseline.

The present disclosure also provides pharmaceutical products comprising ponesimod. Typically, the pharmaceutical product is a package or is packaged, for example, a bottle, a pouch, or a blister pack.

In some embodiments, the package includes instructions. In certain embodiments, instructions are for administering ponesimod to a human patient suffering from multiple sclerosis and fatigue in a regimen that is effective to avoid worsening of fatigue-related symptoms. In other embodiments, the package provides instructions and/or fatigue-related symptom data directed to patients having had no prior disease modifying treatment (DMT) for multiple sclerosis for a period of about two years. In further embodiments, the package provides instructions and/or fatigue-related symptom data directed to patients having a baseline expanded disability status scale (EDSS) score of ≤3.5. In yet other embodiments, the package provides instructions and/or fatigue-related symptom data directed to patients having no Gd+/T1 lesions at baseline.

Figure 3A:
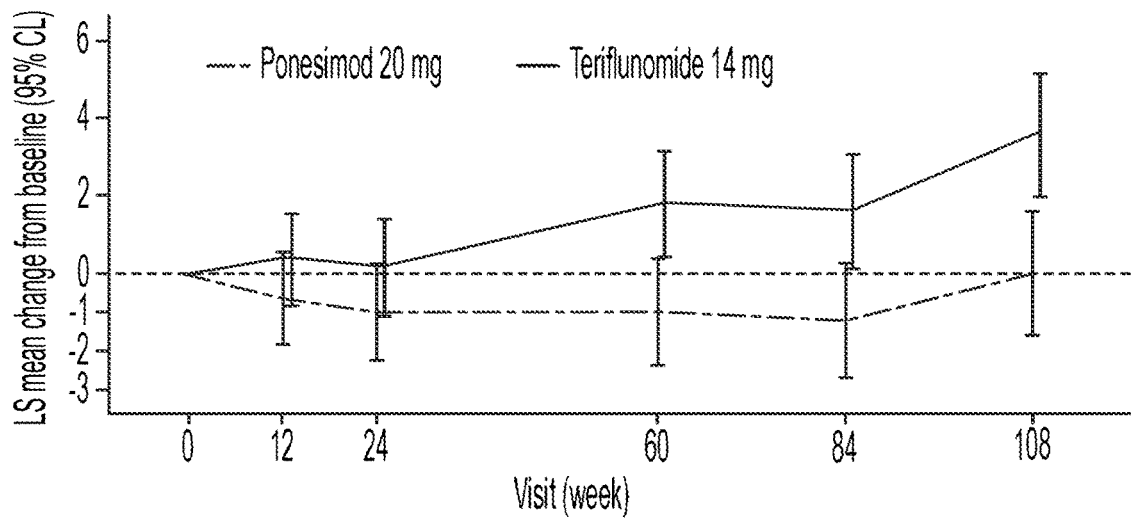
FIG. 3A shows change from baseline up to week 108 for the FSIQ-RMS weekly symptoms score by visit. MMRM (Main analysis) Analysis Set: Full Analysis Set.

As used herein, the term "group level" refers to a group level change or difference between groups of patients, e.g., group level differences in an outcome seen in clinical trials when comparing the treatment groups. For instance, FIG. 3A shows the mean change from baseline for ponesimod 20 mg and teriflunomide 14 mg over time—and it visually shows the separation or difference in change from baseline in the treatment groups.

As used herein, the term "patient level" refers to individual or within patient level of change. As used herein, "clinically meaningful" refers to the practical importance of a treatment effect and whether it has a real genuine, palpable, noticeable effect on symptoms and/or daily life. When interpreting data from a Patient Reported Outcome (PRO), for example, it is helpful to define a level of change on the PRO score over a predetermined time period that should be interpreted as a treatment benefit. Various terms are used for this level of change, including meaningful change threshold (MCT). This threshold can be used to conduct a responder analysis where an individual patient is a responder if the level of change on the PRO score for that patient exceeds the MCT. The proportion of responders between treatment groups can be compared to evaluate treatment effect. For example, in certain embodiments disclosed herein, there is an analysis of the percentage of responders in the ponesimod and teriflunomide treatment groups using an MCT of −6.3 on the FSIQ-RMS weekly symptom score. The percentage of subjects in the stable or improved category is also calculated. And the percentage of responders can also be visualized on a graph (a cumulative distribution function) which shows the cumulative percentage of patients showing all possible levels of change in the respective treatment groups. Accordingly, evaluation of within patient changes using MCT and associated responder analyses are used to provide additional interpretation to a p-value derived from a statistical test As used herein, the term "statistically significant" refers to the likelihood that a relationship between two or more variables is caused by something other than chance. A p-value less than 0.05 (typically ≤0.05) is a common metric for statistical significance and is indicative of strong evidence against the null hypothesis, as there is less than a 5% probability the null is correct (and the results are random).

As used herein, unless otherwise noted, the terms "treating", "treatment" and the like, shall include the management and care of a subject or patient (preferably mammal, more preferably human) for the purpose of combating a disease, condition, or disorder and includes the administration of a compound described herein to prevent the onset of the symptoms or complications, alleviate one or more of the symptoms or complications, or eliminate the disease, condition, or disorder.

The disclosure further relates to a pharmaceutical product comprising ponesimod, wherein the pharmaceutical product is packaged, and wherein the package includes a label that identifies ponesimod as a an approved product for the treatment of multiple sclerosis. In some embodiments, the patient's multiple sclerosis is relapsing multiple sclerosis. In other embodiments, the relapsing multiple sclerosis comprises relapsing-remitting disease, clinically isolated syndrome, or active secondary progressive disease.

The disclosure provides methods for treating multiple sclerosis in a patient in need thereof, comprising administering an approved product comprising ponesimod in an amount and manner that is described in a drug product label for the approved product and/or in a treatment regimen described herein.

In certain aspects, methods of selling a drug product comprising ponesimod are also provided. The terms "sale" or "selling" as used herein refers to transferring a drug product, e.g., a pharmaceutical composition or a dosage form, from a seller to a buyer. In some embodiments, a drug product label for a reference listed drug for the drug product includes instructions for the treatment of multiple sclerosis.

The term "offering for sale," as used herein, refers to the proposal of a sale by a seller to a buyer for a drug product, e.g., a pharmaceutical composition or a dosage form. These methods comprise offering the drug product for sale.

The term "drug product" is product that contains an active pharmaceutical ingredient that has been approved for marketing by a governmental authority, e.g., the Food and Drug Administration or the similar authority in other countries. In the context of the present disclosure, and as reflected in Example 4, an "approved drug product" as used herein means: a pharmaceutical product that i) has been approved for introduction into commerce by a regulatory agency for use in treating adult humans with relapsing forms of multiple sclerosis, to include clinically isolated syndrome, relapsing-remitting disease, and active secondary progressive disease; ii) has an oral, once daily maintenance dosage of 20 mg of ponesimod and, optionally, a 14-day dose titration prior to the maintenance dosage of 20 mg, comprising administering orally, once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; 10 mg of ponesimod on days 12, 13, and 14, followed by the 20 mg maintenance dosage of ponesimod on Day 15 and thereafter; and (iii) demonstrated a statistically significant lower annualized relapse rate (ARR), and, optionally, a statistically significant lower number of Gd-enhancing T1 lesions and/or a statistically significant lower number of new or enlarging T2 lesions, without double counting of lesions, in a patient population with relapsing forms of MS, wherein the patients had an expanded disability status scale (EDSS) score of 0 to 5.5 at baseline, had experienced at least one relapse within the year prior, or two relapses within the prior 2 years, or who had at least one gadolinium-enhancing (Gd-enhancing) lesion on a brain MRI within the prior 6 months or at baseline, wherein patients with primary progressive MS were excluded, compared to the patients in the patient population that were administered a once daily 14 mg dosage of teriflunomide. Elements of the approved drug product are further defined in Example 4, Section 14, including Table 4 therein.

In particular embodiments of the approved drug product, the patients in the patient population were treated for 108 weeks and ARR was reduced by 30.5% compared to teriflunomide 14 mg.

Similarly, "label" or "drug product label" refers to information provided to a patient which provides relevant information regarding the drug product. Such information includes, without limitation, one or more of the description of the drug, clinical pharmacology, indications (uses for the drug product), contraindication (who should not take the drug product), warnings, precautions, adverse events (side effects), drug abuse and dependence, dosage and administration, use in pregnancy, use in nursing mothers, use in children and older patients, how the drug is supplied, safety information for the patient, or any combination thereof. In certain embodiments, the label or drug product label provides an instruction for use in a patient requiring multiple sclerosis medication. In further embodiments, the label or drug product label identifies ponesimod and provides instructions for its use in a patient requiring multiple sclerosis medication.

The term "reference listed drug" or "RLD" as used herein refers to a drug product to which new generic versions are compared to show that they are bioequivalent. It is also a medicinal product that has been granted marketing authorization by a member state of the European Union or by the Commission on the basis of a completed dossier, i.e., with the submission of quality, pre-clinical and clinical data in accordance with Articles 8(3), 10a, 10b or 10c of Directive 2001/83/EC and to which the application for marketing authorization for a generic/hybrid medicinal product refers, by demonstration of bioequivalence, usually through the submission of the appropriate bioavailability studies.

In the United States, a company seeking approval to market a generic equivalent must refer to the RLD in its Abbreviated New Drug Application (ANDA). For example, an ANDA applicant relies on the FDA's finding that a previously approved drug product, i.e., the RLD, is safe and effective, and must demonstrate, among other things, that the generic drug product is the same as the RLD in certain ways. Specifically, with limited exceptions, a drug product for which an ANDA is submitted must have, among other things, the same active ingredient(s), conditions of use, route of administration, dosage form, strength, and (with certain permissible differences) labeling as the RLD. The RLD is the listed drug to which the ANDA applicant must show its ANDA drug product is the same with respect to active ingredient(s), dosage form, route of administration, strength, labeling and conditions of use, among other characteristics. In the electronic Orange Book, there is a column for RLDs and a column for reference standards. In the printed version of the Orange Book, the RLDs and reference standards are identified by specific symbol.

A reference standard is the drug product selected by FDA that an applicant seeking approval of an ANDA must use in conducting an in vivo bioequivalence study required for approval. FDA generally selects a single reference standard that ANDA applicants must use in in vivo bioequivalence testing. Ordinarily, FDA will select the reference listed drug as the reference standard. However, in some instances (e.g., where the reference listed drug has been withdrawn from sale and FDA has determined it was not withdrawn for reasons of safety or effectiveness, and FDA selects an ANDA as the reference standard), the reference listed drug and the reference standard may be different.

FDA identifies reference listed drugs in the Prescription Drug Product, OTC Drug Product, and Discontinued Drug Product Lists. Listed drugs identified as reference listed drugs represent drug products upon which an applicant can rely in seeking approval of an ANDA. FDA intends to update periodically the reference listed drugs identified in the Prescription Drug Product, OTC Drug Product, and Discontinued Drug Product Lists, as appropriate.

FDA also identifies reference standards in the Prescription Drug Product and OTC Drug Product Lists. Listed drugs identified as reference standards represent the FDA's best judgment at this time as to the appropriate comparator for purposes of conducting any in vivo bioequivalence studies required for approval.

In some instances when FDA has not designated a listed drug as a reference listed drug, such listed drug may be shielded from generic competition. If FDA has not designated a reference listed drug for a drug product the applicant intends to duplicate, the potential applicant may ask FDA to designate a reference listed drug for that drug product.

FDA may, on its own initiative, select a new reference standard when doing so will help to ensure that applications for generic drugs may be submitted and evaluated, e.g., in the event that the listed drug currently selected as the reference standard has been withdrawn from sale for other than safety and efficacy reasons.

In Europe, Applicants identify in the application form for its generic/hybrid medicinal product, which is the same as an ANDA or supplemental NDA (sNDA) drug product, the reference medicinal product (product name, strength, pharmaceutical form, marketing authorization holder (MAH, first authorization, Member State/Community), which is synonymous with a RLD, as follows:

1. The medicinal product that is or has been authorized in the European Economic Area (EEA), used as the basis for demonstrating that the data protection period defined in the European pharmaceutical legislation has expired. This reference medicinal product, identified for the purpose of calculating expiry of the period of data protection, may be for a different strength, pharmaceutical form, administration route or presentation than the generic/hybrid medicinal product.

2. The medicinal product, the dossier of which is cross-referred to in the generic/hybrid application (product name, strength, pharmaceutical form, MAH, marketing authorization number). This reference medicinal product may have been authorized through separate procedures and under a different name than the reference medicinal product identified for the purpose of calculating expiry of the period of data protection. The product information of this reference medicinal product will, in principle, serve as the basis for the product information claimed for the generic/hybrid medicinal product.

3. The medicinal product (product name, strength, pharmaceutical form, MAH, Member State of source) used for the bioequivalence study(ies) (where applicable).

The different abbreviated approval pathways for drug products under the Food, Drug, and Cosmetics (FD&C) Act are the abbreviated approval pathways described in sections 505(j) and 505(b)(2) of the FD&C Act (21 U.S.C. 355(j) and 21 U.S.C. 23 355(b)(2), respectively).

According to the FDA ("Determining Whether to Submit an ANDA or a 505(b)(2) Application Guidance for Industry," U.S. Department of Health and Human Services, October 2017, pp. 1-14, the contents of which is incorporated herein by reference), NDAs and ANDAs can be divided into the following four categories:

(1) A "stand-alone NDA" is an application submitted under section 505(b)(1) and approved under section 505(c) of the FD&C Act that contains full reports of investigations of safety and effectiveness that were conducted by or for the applicant or for which the applicant has a right of reference or use.

(2) A section 505(b)(2) application is an NDA submitted under section 505(b)(1) and approved under section 505(c) of the FD&C Act that contains full reports of investigations of safety and effectiveness, where at least some of the information required for approval comes from studies not conducted by or for the applicant and for which the applicant has not obtained a right of reference or use.

(3) An ANDA is an application for a duplicate of a previously approved drug product that was submitted and approved under section 505(j) of the FD&C Act. An ANDA relies on the FDA's finding that the previously approved drug product, i.e., the reference listed drug (RLD), is safe and effective. An ANDA generally must contain information to show that the generic product (a) is the same as the RLD with respect to the active ingredient(s), conditions of use, route of administration, dosage form, strength, and labeling (with certain permissible differences) and (b) is bioequivalent to the RLD. An ANDA may not be submitted if studies are necessary to establish the safety and effectiveness of the product.

(4) A petitioned ANDA is a type of ANDA for a drug product that differs from the RLD in its dosage form, route of administration, strength, or active ingredient (in a product with more than one active ingredient) and for which FDA has determined, in response to a petition submitted under section 505(j)(2)(C) of the FD&C Act (suitability petition), that studies are not necessary to establish the safety and effectiveness of the drug product.

A scientific premise underlying the Hatch-Waxman Act is that a drug product approved in an ANDA under section 505(j) of the FD&C Act is presumed to be therapeutically equivalent to its RLD. Products classified as therapeutically equivalent can be substituted with the full expectation that the substituted product will produce the same clinical effect and safety profile as the prescribed product when administered to patients under the conditions specified in the labeling. In contrast to an ANDA, a section 505(b)(2) application allows greater flexibility as to the characteristics of the product. A section 505(b)(2) application will not necessarily be rated therapeutically equivalent to the listed drug it references upon approval.

The term "therapeutically equivalent to a reference listed drug" means that the drug product is a generic equivalent, i.e., pharmaceutical equivalents, of the reference listed drug product and, as such, is rated an AB therapeutic equivalent to the reference listed drug product by the FDA whereby actual or potential bioequivalence problems have been resolved with adequate in vivo and/or in vitro evidence supporting bioequivalence.

"Pharmaceutical equivalents" means drug products in identical dosage forms and route(s) of administration that contain identical amounts of the identical active drug ingredient as the reference listed drug.

FDA classifies as therapeutically equivalent those products that meet the following general criteria: (1) they are approved as safe and effective; (2) they are pharmaceutical equivalents in that they (a) contain identical amounts of the same active drug ingredient in the same dosage form and route of administration, and (b) meet compendial or other applicable standards of strength, quality, purity, and identity; (3) they are bioequivalent in that (a) they do not present a known or potential bioequivalence problem, and they meet an acceptable in vitro standard, or (b) if they do present such a known or potential problem, they are shown to meet an appropriate bioequivalence standard; (4) they are adequately labeled; and (5) they are manufactured in compliance with Current Good Manufacturing Practice regulations The term "bioequivalent" or "bioequivalence" is the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Section 505 (j)(8)(B) of the FD&C Act describes one set of conditions under which a test and reference listed drug shall be considered bioequivalent:

the rate and extent of absorption of the [test] drug do not show a significant difference from the rate and extent of absorption of the [reference] drug when administered at the same molar dose of the therapeutic ingredient under similar experimental conditions in either a single dose or multiple doses; or the extent of absorption of the [test] drug does not show a significant difference from the extent of absorption of the [reference] drug when administered at the same molar dose of the therapeutic ingredient under similar experimental conditions in either a single dose or multiple doses and the difference from the [reference] drug in the rate of absorption of the drug is intentional, is reflected in its labeling, is not essential to the attainment of effective body drug concentrations on chronic use, and is considered medically insignificant for the drug.

Where these above methods are not applicable (e.g., for drug products that are not intended to be absorbed into the bloodstream), other scientifically valid in vivo or in vitro test methods to demonstrate bioequivalence may be appropriate.

For example, bioequivalence may sometimes be demonstrated using an in vitro bioequivalence standard, especially when such an in vitro test has been correlated with human in vivo bioavailability data. In other situations, bioequivalence may sometimes be demonstrated through comparative clinical trials or pharmacodynamic studies.

The methods may also comprise, consist of, or consist essentially of selling or offering to sell ponesimod into the stream of commerce.

Clinical Management Events

As noted herein, sphingosine-1-phosphate receptor modulators (S1Ps), a class of oral disease, modifying therapies (DMTs) for multiple sclerosis (MS), are cell-trafficking inhibitors that have been shown to have high efficacy. There are at least four S1Ps that are indicated for MS in the United States: fingolimod, siponimod, ozanimod, and ponesimod. Although these S1Ps share some similarities as a class, the individual S1Ps have differences in selectivity for receptor subtypes and phosphorylation requirements, half-lives, and safety profiles that result in different clinical requirements before and after treatment initiation. Some clinical management events are common across the S1Ps, such as complete blood count, electrocardiogram, and liver function tests before treatment initiation. However, each S1P also has unique recommendations for clinical management events described in their US Prescribing Information (USPI), which may impact their overall ease of use. S1Ps with fewer clinical management events may be easier to use than those that require more monitoring.

As used herein, clinical management events refer to management of potential or actual events that may require medical intervention. As described herein, clinical management events prior to initiation of treatment include, for example, first-dose monitoring, genotyping, and/or an eye exam. After initiation, events include, for example, drug-drug interactions (DDI), eye exam, and/or liver function tests.

The disclosure provides methods for reducing clinical management events before or during treatment of multiple sclerosis in a patient in need thereof, comprising administering ponesimod in an amount and manner that is described in a drug product label for an approved product and/or in a treatment regimen described herein, namely administration of about 20 mg of ponesimod orally once daily, with or without utilization of the up-titration dosing procedure also described herein. The reduction and ease of use are relative to a patient population at substantially the same level of disease progression receiving a standard of care treatment comprising an S1P receptor modulator other than ponesimod, including, for example, fingolimod, siponimod, and ozanimod (see Example 3).

Other Aspects of the Disclosure

Beta blockers, also known as beta-adrenergic blocking agents, are widely used medications to reduce blood pressure and may be co-administered in MS patients. Concomitant use of ponesimod and drugs that decrease heart rate may be result in bradycardia and heart block. As a result, caution should be applied when ponesimod is initiated in patients receiving treatment with a beta-blocker because of the additive effects on lowering heart rate. In certain embodiments, for patients receiving a stable dose of a beta-blocker, the resting heart rate should be considered before introducing ponesimod treatment. If the resting heart rate is greater than 55 bpm under chronic beta-blocker treatment, ponesimod can be introduced. If the resting heart rate is less than or equal to 55 bpm, beta-blocker treatment should be interrupted until the baseline heart rate is greater than 55 bpm. In this case, treatment with ponesimod can then be initiated and treatment with a beta-blocker can be reinitiated after ponesimod has been up-titrated (via the 14-day titration regimen) to the target maintenance dosage.

For example, the negative chronotropic effect of coadministration of ponesimod and propranolol was evaluated in a dedicated pharmacodynamics safety study. In particular, the 14-day dose titration regimen of ponesimod was administered to subjects receiving propranolol (80 mg) once daily. As noted in Example 4, no significant changes in pharmacokinetics of ponesimod or propranolol were observed.

In particular embodiments, where a patient is being treated with a beta-blocker and ponesimod treatment is to be initiated, and wherein the patient has a resting heart rate of greater than 55 beats per minute during treatment with the beta-block and prior to initiation of ponesimod, ponesimod is administered without interruption to the beta-blocker treatment. In other embodiments, where a patient is being treated with a beta-blocker and ponesimod treatment is to be initiated, and wherein the patient has a resting heart rate of less than or equal to 55 beats per minute during treatment with the beta-block and prior to initiation of ponesimod, beta-blocker treatment is interrupted until the patient's heart rate is greater than 55 beats per minute and ponesimod treatment is initiated in a titration regimen comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; and 10 mg of ponesimod on days 12, 13, and 14, followed by administering a 20 mg maintenance dose of ponesimod once daily thereafter, and the beta-blocker is reinitiated after ponesimod has been up-titrated to the maintenance dosage.

Because initiation of ponesimod treatment results in a decrease in heart rate (HR), first-dose 4-hour monitoring is also recommended for patients with sinus bradycardia (HR less than 55 beats per minute (bpm)), first- or second-degree (Mobitz type I) AV block, or a history of myocardial infarction or heart failure occurring more than 6 months prior to treatment initiation and in stable condition. As part of the first dose 4-hour monitoring, a first dose of ponesimod (e.g. 2 mg of ponesimod as part of the titration regimen) is administered in a setting where resources to appropriately manage symptomatic bradycardia are available. Patients are to be monitored for 4 hours after the first dose for signs and symptoms of bradycardia with pulse and blood pressure measurements, preferably with a minimum of hourly measurements. Further, in additional embodiments, an electrocardiogram (ECG) is obtained for these patients prior to dosing and at the end of the 4-hour observation period.

Accordingly, methods include treating multiple sclerosis in a patient in need thereof, wherein the patient has sinus bradycardia, first or second degree AV block, or a history of myocardial infarction or heart failure occurring more than 6 months prior to the initiation of ponesimod treatment, comprising administering an effective regimen of ponesimod to the patient, wherein after a first dose of the ponesimod, the patient is monitored for a period of 4 hours for symptoms of bradycardia. In other embodiments, no first dose monitoring is needed wherein the patient has no sinus bradycardia, no first or second degree AV block, and no history of myocardial infarction or heart failure occurring more than 6 months prior to the initiation of ponesimod treatment.

If any abnormalities are present after four hours, even in the absence of symptoms, monitoring may be continued until the abnormality resolves. Abnormalities include, for example, a heart rate 4 hours post-dose that is less than 45 bpm; a heart rate 4 hours post-dose that is at the lowest value post-dose, suggesting that the maximum pharmacodynamic effect on the heart may not have occurred; and/or an ECG 4 hours post-dose that shows new onset second-degree or higher AV block.

If post-dose symptomatic bradycardia, bradyarrhythmia, or conduction related symptoms occur, or if ECG 4 hours post-dose shows new onset second degree or higher AV block or QTc greater than or equal to 500 msec, appropriate management actions can be initiated. For example, the patient can begin continuous ECG monitoring, and can otherwise be monitored until the symptoms have resolved if no pharmacological treatment is required. If pharmacological treatment is required, the patient can be continued to be monitored, including overnight, and the 4-hour monitoring can be repeated after the second dose of ponesimod.

In other embodiments, where patients have a preexisting heart and/or cerebrovascular condition; a prolonged QTc interval before dosing or during the 4-hour observation, or at additional risk for QT prolongation, or on concurrent therapy with QT prolonging drug with a known risk of torsades de pointes; and/or receiving concurrent therapy with drugs that slow heart rate or AV conduction, advice from a cardiologist should be sought to determine the most appropriate monitoring strategy, which can include, for example, overnight monitoring during treatment initiation.

Although interruption during treatment is not preferred, this disclosure is also related to reinitiating ponesimod after treatment interruption. For example, if fewer than 4 consecutive doses are missed during titration, treatment is resumed with the first missed titration dose and the titration schedule is resumed as that dose and titration day. If fewer than 4 doses are missed during maintenance, treatment is resumed with the maintenance dose. If 4 our more consecutive doses are missed during titration or maintenance, treatment is reinitiated with Day 1 of the 14 day titration regimen, with first dose monitoring as described herein for those patients needing such monitoring.

In other embodiments, use or concomitant use of certain drugs with ponesimod should be contraindicated, avoided, or discontinued. For example, methods include treating multiple sclerosis in a patient in need thereof, comprising administering an effective regimen of ponesimod to the patient wherein the treatment further comprises avoiding, contradicting, or discontinuing concomitant use of alemtuzumab. Other methods include treating multiple sclerosis in a patient in need thereof, comprising administering an effective regimen of ponesimod to the patient wherein the treatment further comprises avoiding, contradicting, or discontinuing concomitant use of QT prolonging drugs with known arrhythmogenic properties, heart rate lowering calcium channel blockers (such as, for example, verapamil or diltiazem), or other drugs that reduce heart rate (such as, for example, digoxin). Additional methods include treating multiple sclerosis in a patient in need thereof, comprising administering an effective regimen of ponesimod to the patient wherein the treatment further comprises avoiding, contradicting, or discontinuing concomitant use of strong CYP3A4 and UGT1A1 inducers (such as, for example, rifampin, phenytoin, or carbamazepine) that decrease systemic exposure of the ponesimod.

Aspects of the Disclosure—the Present Disclosure Pertains to and Includes at Least the Following Additional Aspects 1. A method for treating multiple sclerosis in a patient in need thereof, comprising administering an approved drug product comprising ponesimod in an amount and manner that is described in a drug product label for the approved drug product.
2. The method of aspect 1, wherein about 20 mg of ponesimod is administered orally once daily
3. The method of aspect 1 or aspect 2, wherein the treatment comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by administering 20 mg of ponesimod once daily thereafter.
4. The method of any one of aspects 1-3, wherein the multiple sclerosis is relapsing multiple sclerosis.
5. The method of aspect 4, wherein the relapsing multiple sclerosis comprises relapsing-remitting disease, clinically isolated syndrome, or active secondary progressive disease.
6. A method of selling an approved drug product comprising ponesimod, said method comprising selling such drug product, wherein a drug product label for a reference listed drug for such drug product includes instructions for treating a patient with multiple sclerosis.
7. A method of offering for sale a drug product comprising ponesimod, said method comprising offering for sale such drug product, wherein a drug product label for a reference listed drug for such drug product includes instructions for treating a patient with multiple sclerosis.
8. The method of aspect 6 or aspect 7, wherein the drug product is an ANDA drug product, a supplemental New Drug Application drug product, or a 505(b)(2) drug product.
9. A pharmaceutical product comprising ponesimod, wherein the pharmaceutical product is packaged, and wherein the package includes a label that identifies ponesimod as an approved drug product for the treatment of multiple sclerosis.
10. A method for treating multiple sclerosis in a patient in need thereof, comprising administering an effective regimen of ponesimod to the patient wherein the treatment further comprises avoiding, contradicting, or discontinuing concomitant use of alemtuzumab.
11. A method for treating multiple sclerosis in a patient in need thereof, comprising administering an effective regimen of ponesimod to the patient wherein the treatment further comprises avoiding, contradicting, or discontinuing concomitant use of QT prolonging drugs with known arrhythmogenic properties, heart rate lowering calcium channel blockers (such as, for, example, verapamil or diltiazem), or other drugs that reduce heart rate (such as, for example, digoxin).
12. A method for treating multiple sclerosis in a patient in need thereof, comprising administering an effective regimen of ponesimod to the patient wherein the treatment further comprises avoiding, contradicting, or discontinuing concomitant use of strong CYP3A4 and UGT1A1 inducers (such as, for example, rifampin, phenytoin, or carbamazepine) that decrease systemic exposure of the ponesimod.

The following Examples are provided to illustrate some of the concepts described within this disclosure. While the Examples are considered to provide an embodiment, it should not be considered to limit the more general embodiments described herein Example A: Fatigue Symptoms and Impact Questionnaire—Relapsing Multiple Sclerosis (FSIQ-RMS)

The patient-reported outcome questionnaire used for the below Examples is the Fatigue Symptoms and Impact Questionnaire—Relapsing Multiple Sclerosis (FSIQ-RMS). The FSIQ-RMS is an MS specific 20-item PRO measure that comprises 2 domains: one measuring MS symptoms (7 items) and one measuring MS-related impacts (13 items). The 7 symptom items and 13 impact items (in 3 impacts subdomains: physical, cognitive and emotional, and coping) are presented below.
MS Symptoms Domain 7 Items
For the MS symptoms domain, the FSIQ-RMS asks about a patient's fatigue-related symptoms of relapsing MS over the past 24 hours while doing routine daily activities (e.g., housework, yard work, shopping, working, etc.) for Items 1-6 or while at rest (e.g., reading a book, watching TV, etc.) for Item 7. Patients are asked to select a response on a scale of 0 to 10 that best describes their experience and are asked to not skip any questions, with no answers being right or wrong.
Item 1—In the past 24 hours, while doing routine daily activities, how physically tired did you feel? The scale is from 0 to 10, with 0 being not physically tired at all and 10 being extremely physical tired.
Item 2—In the past 24 hours, while doing routine daily activities, how mentally tired did you feel? The scale is from 0 to 10, with 0 being not mentally tired at all and 10 being extremely mentally tired.
Item 3—In the past 24 hours, while doing routine daily activities, how physical weak did you feel? The scale is from 0 to 10, with 0 being not weak at all and 10 being extremely weak.
Item 4—In the past 24 hours, how would you rate your energy while doing routine daily activities? The scale is from 0 to 10, with 0 being a lot of energy and 10 being no energy at all.
Item 5—In the past 24 hours, while doing routine daily activities, how worn out did you feel? The scale is from 0 to 10, with 0 being not worn out at all and 10 being extremely worn out.

Item 6—In the past 24 hours, while doing routine daily activities, how sleepy did you feel? The scale is from 0 to 10, with 0 being not sleepy at all and 10 being extremely sleepy Item 7—In the past 24 hours, how worn out did you feel while at rest? The scale is from 0 to 10, with 0 being not worn out at all and 10 being extremely worn out.

MS-Related Impacts—13 Items

For the MS-related impacts domain, the FSIQ-RMS asks about how a patient's life was affected by fatigue-related symptoms of relapsing MS in the past 7 days. Patients are asked to select a response on a scale of 0 to 4 that best describes their experience and are asked to not skip any questions, with no answers being right or wrong.

Item 1—Thinking about your fatigue-related symptoms over the past 7 days, how much difficulty did you have running errands (such as grocery shopping or going to the bank or ATM)? The scale is from 0 to 4, with 0 being no difficulty; 1 being a little difficulty; 2 being moderate difficulty; 3 being quite a bit of difficulty; and 4 being extreme difficulty.

Item 2—Thinking about your fatigue-related symptoms over the past 7 days, how much difficulty did you have communicating clearly? The scale is from 0 to 4, with 0 being no difficulty; 1 being a little difficulty; 2 being moderate difficulty; 3 being quite a bit of difficulty; and 4 being extreme difficulty.

Item 3—Thinking about your fatigue-related symptoms over the past 7 days, how much difficulty did you have thinking clearly? The scale is from 0 to 4, with 0 being no difficulty; 1 being a little difficulty; 2 being moderate difficulty; 3 being quite a bit of difficulty; and 4 being extreme difficulty.

Item 4—Thinking about your fatigue-related symptoms over the past 7 days, how difficult was it for you to motivate yourself to do routine daily activities? The scale is from 0 to 4, with 0 being no difficulty; 1 being a little difficulty; 2 being moderate difficulty; 3 being quite a bit of difficulty; and 4 being extreme difficulty.

Item 5—Thinking about your fatigue-related symptoms over the past 7 days, how much difficulty did you have doing indoor household chores? The scale is from 0 to 4, with 0 being no difficulty; 1 being a little difficulty; 2 being moderate difficulty; 3 being quite a bit of difficulty; and 4 being extreme difficulty.

Item 6—Thinking about your fatigue-related symptoms over the past 7 days, how much difficulty did you have walking? The scale is from 0 to 4, with 0 being no difficulty; 1 being a little difficulty; 2 being moderate difficulty; 3 being quite a bit of difficulty; and 4 being extreme difficulty.

Item 7—Thinking about your fatigue-related symptoms over the past 7 days, how much difficulty did you have maintaining relationships with people you are close to? The scale is from 0 to 4, with 0 being no difficulty; 1 being a little difficulty; 2 being moderate difficulty; 3 being quite a bit of difficulty; and 4 being extreme difficulty.

Item 8—Thinking about your fatigue-related symptoms over the past 7 days, how much difficulty did you have taking part in social activities (such as going to the movies or going out to eat)? The scale is from 0 to 4, with 0 being no difficulty; 1 being a little difficulty; 2 being moderate difficulty; 3 being quite a bit of difficulty; and 4 being extreme difficulty.

Item 9—Thinking about your fatigue-related symptoms over the past 7 days, how frustrated were you? The scale is from 0 to 4, with 0 being not at all; 1 being a little bit; 2 being somewhat; 3 being quite a bit; and 4 being extremely.

Item 10—Thinking about your fatigue-related symptoms over the past 7 days, how often were you forgetful? The scale is from 0 to 4, with 0 being never; 1 being rarely; 2 being some of the time; 3 being most of the time; and 4 being almost all of the time.

Item 11—Thinking about your fatigue-related symptoms over the past 7 days, how often did you have to take a nap? The scale is from 0 to 4, with 0 being never; 1 being rarely; 2 being some of the time; 3 being most of the time; and 4 being almost all of the time.

Item 12—Thinking about your fatigue-related symptoms over the past 7 days, how often did you have to take a break? The scale is from 0 to 4, with 0 being never; 1 being rarely; 2 being some of the time; 3 being most of the time; and 4 being almost all of the time.

Item 13—Thinking about your fatigue-related symptoms over the past 7 days, how often did you have to rearrange your plans? The scale is from 0 to 4, with 0 being never; 1 being rarely; 2 being some of the time; 3 being most of the time; and 4 being almost all of the time.

Example 1

Study Design

A prospective, multicenter, randomized, double-blind, active controlled, parallel-group, phase III, superiority study was conducted. The study was designed to compare the efficacy, safety, and tolerability of ponesimod 20 mg vs teriflunomide 14 mg in adult subjects with relapsing MS.

Randomization: Subjects were randomized in a 1:1 ratio to ponesimod 20 mg or teriflunomide 14 mg, stratified by prior use of MS disease modifying treatment (DMT) in the last two years prior to randomization (yes, no) and by baseline expanded disability status scale (EDSS) score (EDSS≤3.5, EDSS>3.5).

Inclusion Criteria

This study enrolled adult male and female subjects aged 18 to 55 years with established diagnosis of MS, as defined by the 2010 revision of McDonald Diagnostic Criteria [Polman C H, et al. *Diagnostic criteria for multiple sclerosis: 2010 revisions to the McDonald criteria*. Ann Neurol. 2011; 69(2):292-302], with relapsing course from onset (i.e., relapsing-remitting multiple sclerosis and secondary progressive multiple sclerosis [SPMS] with superimposed relapses). The trial included up to a maximum 15% of subjects with SPMS with superimposed relapses.

Subjects had active disease evidenced by one or more MS attacks with onset within the period of 12 to 1 months prior to baseline EDSS assessment, or by two or more MS attacks with onset within the 24 to 1 months prior to baseline EDSS assessment, or with one or more gadolinium-enhancing (Gd+) lesion(s) of the brain on an MRI performed within 6 months prior to baseline EDSS assessment. Enrolled subjects were ambulatory with an EDSS score of up to 5.5 inclusive. The subjects were treatment-naïve (i.e., no MS disease-modifying therapy received at any time in the past) or previously treated with interferon (IFN) β-1a, IFN β-1b, glatiramer acetate, dimethyl fumarate, or natalizumab.

Exclusion Criteria:

Subjects with significant medical conditions or therapies for such conditions (e.g., cardiovascular, pulmonary, immunological, hepatic, ophthalmological, ocular) or lactating or pregnant women were not eligible to enter the study.

Subjects with contraindications to MRI or with clinically relevant medical or surgical conditions that, in the opinion of the investigator, would put the subject at risk by participating in the study were not eligible to enter the study.

Study/Treatment Duration:

For an individual subject, the maximum duration of the study was approximately 118 weeks consisting of 6 weeks of screening, 108 weeks of treatment and 4 weeks of safety follow-up. Subjects discontinuing treatment prematurely had an option to stay in a post-treatment observation period (PTOP) for up to 108 weeks.

The study consisted of the following periods:

Pre-randomization period—Up to 45 days before randomization.

Treatment period: The double-blind treatment period lasted for 108 weeks. It consisted of a randomization visit, visits at two, four, and 12 weeks after randomization, and 12-weekly visits thereafter.

End-of-Treatment (EOT):

The EOT visit took place at Week 108 (or earlier in case of premature discontinuation of study drug). In all cases, the EOT visit took place one day after the last dose of study drug but no later than 7 days after the last dose of study drug.

Subjects who completed treatment until Week 108 were eligible to enroll in an extension study conducted under a separate protocol. Subjects who discontinued study drug prematurely for any reason were not eligible for the extension study.

Subjects who prematurely discontinued study drug treatment were subsequently treated according to local standard of care at the investigator's discretion and were followed in the post-treatment observation period.

Post-Treatment Safety Follow-Up (FU) Period:

Teriflunomide is eliminated slowly from plasma. An accelerated elimination procedure was used by all subjects after the last dose of study drug. A safety FU after the last dose of study drug was mandated.

All Subjects Entered the Safety FU Period:

For subjects who entered the extension study, the FU period started after the last dose of study drug and ended with a safety FU visit (FU1) 14-22 days after the last dose of study drug or with an abbreviated FU2 23-37 days after the last dose of study drug (if compliance to the teriflunomide accelerated elimination procedure was assessed as not sufficient at FU1).

For subjects who did not enter the extension study, the safety FU period lasted for 30 days after the last dose of study drug and included two safety FU visits (FU1, FU2) at 14-22 and 30-37 days after the last dose of study drug, respectively.

Post-Treatment Observation Period (PTOP):

Subjects who prematurely discontinued study treatment enter the PTOP which lasts until 108 weeks after randomization (i.e., planned EOT period). It consisted of an abbreviated schedule of assessments at the time of the originally scheduled 12-weekly visits.

End-of-Study (EOS)

EOS was reached when treatment, safety FU, and, if applicable, PTOP have been completed.

For subjects who completed the 108-week treatment period and entered the extension study, the EOS visit corresponded to the FU visit (FU1) conducted 14-22 days after the last study drug dose or to the abbreviated FU2 visit conducted 23-37 days after the last study drug dose (if needed for compliance reasons with the teriflunomide accelerated elimination procedure).

For all other subjects, the EOS visit corresponded to the 30-day FU visit (FU2) or to the last visit of PTOP (i.e., Week 108 Visit of the PTOP), whichever was last.

Study Treatment:

The treatment period consisted of an up-titration period (from Day 1 to 14) and a maintenance period (Day 15 until EOT).

During an initial phase of the study, the study drugs in the up-titration period were administered in a double-dummy fashion. Ponesimod (or matching placebo) was presented as tablet, and teriflunomide 14 mg (or matching placebo) was presented as capsule (i.e., daily administration of one tablet and one capsule). At a later phase, the double-dummy material (tablet and capsule) was replaced by the daily administration of one capsule containing either ponesimod or teriflunomide.

In the maintenance period, the study treatment consisted of the daily administration of one capsule containing ponesimod 20 mg or teriflunomide 14 mg.

To reduce the first-dose effect of ponesimod, an up-titration scheme was implemented from Day 1 to Day 14:

Days 1 and 2; 2 mg.
Days 3 and 4; 3 mg.
Days 5 and 6; 4 mg.
Day 7; 5 mg.
Day 8; 6 mg.
Day 9; 7 mg.
Day 10; 8 mg.
Day 11; 9 mg.
Days 12, 13, and 14; 10 mg.
Day 15 until EOT; 20 mg.

Primary analysis set for efficacy: The Full Analysis Set (FAS) included all randomized subjects. Subjects were evaluated according to the treatment they were randomized to.

Primary efficacy variable/primary timepoint: The primary endpoint was annualized relapse rate (ARR) up to the end of study (EOS) defined as the number of confirmed relapses per subject-year. All available data up to EOS, regardless of treatment discontinuation was included (ITT approach).

Secondary efficacy variables and testing strategy: Four secondary efficacy endpoints were analyzed as per the statistical testing strategy outlined in FIG. 1.

Change from baseline to Week 108 in fatigue-related symptoms as measured by the symptoms domain of the FSIQ-RMS patient-reported outcome [Fatigue]

Cumulative number of combined unique active lesions from baseline to Week 108 on brain MRI [CUALs]

Time to first 12-week confirmed disability accumulation (CDA) from baseline to EOS on Expanded Disability Status Scale (EDSS) [12-week CDA]

Time to first 24-week CDA from baseline to EOS on EDSS [24-week CDA]

See FIG. 1 for a schematic representation of the testing strategy.

The primary endpoint was powered with $\alpha=0.01$. The secondary endpoints tested with an overall $\alpha=0.05$.

The sample size for the study was based on the primary endpoint and determined assuming a negative binomial distribution for number of confirmed relapses. A sample size of 1100 subjects (550 per treatment arm) would provide a power of approximately 90% for a significance level of 1%, under the assumption that ARR is 0.320 for teriflunomide 14 mg and 0.215 for ponesimod 20 mg (which corresponds to a rate ratio of 0.67) and using a dispersion=0.9. An annual dropout rate of approximately 15% was assumed for the first year and 7.5% for the second year.

Statistical Methods

The Full Analysis Set (FAS) included all randomized subjects. In order to adhere to the intention-to-treat principle as much as possible, subjects were evaluated according to the treatment they have been randomized to.

The Per-Protocol Set (PPS) comprises all subjects included in the FAS without any major protocol deviations, that impact the assessment of the primary/secondary endpoints, occurring prior to or at randomization.

The Safety Set (SAF) included all randomized subjects who received at least one dose of study treatment. Subjects were analyzed based on actual treatment taken, not randomized treatment.

A generalized linear model with negative binomial distribution was fitted for the primary efficacy endpoint ARR. Two-sided hypotheses were expressed in terms of the model parameters $\mu$P20 mg and $\mu$T14 mg. The primary null hypothesis was that the ARR ($\mu$) does not differ between ponesimod 20 mg and teriflunomide 14 mg.

The null hypothesis was tested by a two-sided Wald test within the negative binomial regression model with a two-sided significance level of 0.01 for conclusive evidence and 0.05 for a positive study. Two-sided 99% and 95% Wald confidence intervals were calculated for the relative reduction in mean ARR for ponesimod 20 mg compared to teriflunomide 14 mg.

The primary statistical analysis of the ARR endpoint was performed on the FAS using a negative binomial model for confirmed relapses, with the stratification variables prior use of disease-modifying therapies (DMTs) and EDSS category as well as the number of relapses in the year prior to study entry, included in the model and time in the study as an offset variable. Sensitivity analyses was performed on the PPS and also based on different subgroups derived from baseline variables.

The secondary efficacy endpoints were tested if the primary analysis on ARR leads to the rejection of the null hypothesis in favor of ponesimod 20 mg at an overall two-sided significance level of 0.05. A fallback method was used for testing the family of hypotheses related to the following three secondary endpoints: Absolute change of FSIQ-RMS from baseline to Week 108; Cumulative number of CUAL from baseline to Week 108; Time to 12-week CDA from baseline up to EOS. This was followed in a hierarchical manner by testing Time to 24-week CDA from baseline up to EOS; at the remaining alpha.

The endpoints were analyzed using the FAS population. All secondary endpoints were also analyzed using the PPS population.

Primary Objective

To determine whether ponesimod is more efficacious than teriflunomide in terms of reducing relapses in subjects with RMS.

Results

Disposition and baseline characteristics: A total of 1133 subjects were randomized to the study, 567 to ponesimod 20 mg and 566 to teriflunomide 14 mg. Overall treatment and study discontinuation were balanced across both treatment arms, 83% of subjects completed treatment. The mean age was 36.7 years and 64.9% of subjects were female. Most subjects were recruited in Europe with 50.6% from EU countries. Mean baseline EDSS score was 2.6 and mean disease duration was 7.6 years. Mean pre-study 12-month relapse rate was 1.3, and 42.6% subjects had ≥1 gadolinium-enhancing (Gd+) T1 lesions. The treatment arms were generally balanced in terms of demographics and baseline disease characteristics.

1. Subject and Treatment Information

A total of 1468 subjects were screened. Of those, 1133 subjects were randomized (567 to ponesimod 20 mg and 566 to teriflunomide 14 mg) across 162 sites in 28 countries, and 1131 subjects received at least one dose of study drug. The disposition of subjects is summarized in Table 1 and a summary of reasons (primary reason) for treatment discontinuation are shown in Table 2. Overall treatment and study discontinuation were balanced across both treatment arms. A total of 6.5% and 2.5% of the subjects discontinued due to AEs or tolerability related reasons in ponesimod 20 mg and teriflunomide 14 mg, respectively, while 1.9% and 4.3% discontinued due to efficacy related reasons. There were 2 deaths reported during the study—both on teriflunomide 14 mg.

1.1 Disposition and Treatment Discontinuation Information

TABLE 1

Disposition of subjects
Analysis Set: Subjects screened

|  | Ponesimod 20 mg N = 567 n (%) | Teriflunomide 14 mg N = 566 n (%) | Total N = 1133 n (%) |
| --- | --- | --- | --- |
| Subjects screened |  |  | 1468 |
| Subjects re-screened |  |  | 110 |
| Subjects randomized | 567 (100) | 566 (100) | 1133 (100) |
| Subjects randomized after re-screening | 47 (8.3) | 36 (6.4) | 83 (7.3) |
| Subjects treated | 565 (99.6) | 566 (100) | 1131 (99.8) |
| Subjects completed treatment as per protocol | 471 (83.1) | 473 (83.6) | 944 (83.3) |
| Subjects completed study as per protocol | 490 (86.4) | 495 (87.5) | 985 (86.9) |
| Subjects completed treatment and study as per protocol | 465 (82.0) | 465 (82.2) | 930 (82.1) |
| Subjects stayed in study beyond safety follow-up (PTOP) | 67 (11.8) | 62 (11.0) | 129 (11.4) |

Percentages based on subjects randomized Safety follow-up is up to EOT + 30 days. PTOP = Post-treatment observation period.

TABLE 2

Reasons for premature treatment discontinuation
Analysis Set: Safety Set

|  | Ponesimod 20 mg N = 565 n (%) | Teriflunomide 14 mg N = 566 n (%) | Total N = 1131 n (%) |
|---|---|---|---|
| Subjects who prematurely discontinued study treatment | 94 (16.6) | 93 (16.4) | 187 (16.5) |
| Reasons for premature discontinuation of study treatment |  |  |  |
| Subject decision | 39 (6.9) | 49 (8.7) | 88 (7.8) |
| Efficacy related | 7 (1.2) | 14 (2.5) | 21 (1.9) |
| Tolerability related | 8 (1.4) | 5 (0.9) | 13 (1.1) |
| Other | 19 (3.4) | 26 (4.6) | 45 (4.0) |
| Not known | 5 (0.9) | 4 (0.7) | 9 (0.8) |
| Physician decision | 40 (7.1) | 23 (4.1) | 63 (5.6) |
| Adverse event | 29 (5.1) | 9 (1.6) | 38 (3.4) |
| Lack of efficacy/treatment failure | 4 (0.7) | 10 (1.8) | 14 (1.2) |
| Other | 7 (1.2) | 4 (0.7) | 11 (1.0) |
| Pre-specified study treatment discontinuation criteria | 12 (2.1) | 16 (2.8) | 28 (2.5) |
| Lost to follow-up | 2 (0.4) | 3 (0.5) | 5 (0.4) |
| Death | 0 | 2 (0.4) | 2 (0.2) |
| Reason not provided | 1 (0.2) | 0 | 1 (0.1) |

1.2 Demographic and Baseline Characteristics

Randomization was stratified by prior-DMT in the last two years prior to randomization (yes: 39.5%; no: 60.5%) and EDSS score at baseline (≤3.5: 83.3%; >3.5 16.7%). The mean age was 36.7 years and the majority of subjects (64.9%) were female. Most subjects were recruited in Europe with 50.6% from EU countries. Mean baseline EDSS score was 2.6, mean disease duration was 7.6 years and 97.4% were RRMS subjects. Mean pre-study 12-month relapse rate was 1.3, and 42.6% subjects had ≥1 Gd+T1 lesions on brain MRI. The treatment arms were generally balanced in terms of demographics and baseline disease characteristics (Tables 3 and 4).

TABLE 3

Demographic characteristics
Analysis Set: Full Analysis Set

|  | Ponesimod 20 mg N = 567 | Teriflunomide 14 mg N = 566 | Total N = 1133 |
|---|---|---|---|
| Sex [n (%)] |  |  |  |
| N | 567 | 566 | 1133 |
| Male | 204 (36.0) | 194 (34.3) | 398 (35.1) |
| Female | 363 (64.0) | 372 (65.7) | 735 (64.9) |
| Age (years) |  |  |  |
| N | 567 | 566 | 1133 |
| Mean | 36.7 | 36.8 | 36.7 |
| SD | 8.74 | 8.74 | 8.74 |
| Median | 36.0 | 37.0 | 37.0 |
| Q1, Q3 | 30.0, 44.0 | 30.0, 44.0 | 30.0, 44.0 |
| Min, Max | 18, 55 | 18, 55 | 18, 55 |
| Race [n (%)] |  |  |  |
| N | 567 | 566 | 1133 |
| White | 551 (97.2) | 553 (97.7) | 1104 (97.4) |
| American Indian or Alaska Native | 0 | 1 (0.2) | 1 (0.1) |
| Black or African American | 3 (0.5) | 2 (0.4) | 5 (0.4) |
| Other | 5 (0.9) | 2 (0.4) | 7 (0.6) |
| Not applicable | 8 (1.4) | 8 (1.4) | 16 (1.4) |
| Geographical region/Country of enrolling site [n (%)] |  |  |  |
| European Union (EU) + UK | 289 (51.0) | 284 (50.2) | 573 (50.6) |
| Europe Non-EU + Russia | 233 (41.1) | 239 (42.2) | 472 (41.7) |
| North America | 32 (5.6) | 24 (4.2) | 56 (4.9) |
| Rest of World | 13 (2.3) | 19 (3.4) | 32 (2.8) |

TABLE 4

Baseline disease characteristics
Analysis Set: Full Analysis Set

|  | Ponesimod 20 mg N = 567 | Teriflunomide 14 mg N = 566 | Total N = 1133 |
|---|---|---|---|
| Baseline EDSS | | | |
| N | 567 | 566 | 1133 |
| Mean | 2.57 | 2.56 | 2.56 |
| SD | 1.174 | 1.229 | 1.201 |
| Median | 2.50 | 2.50 | 2.50 |
| Q1, Q3 | 1.50, 3.50 | 1.50, 3.50 | 1.50, 3.50 |
| Min, Max | 0.0, 5.5 | 0.0, 5.5 | 0.0, 5.5 |
| Any DMT(a) received within 2 years prior to Randomization (eCRF) [n (%)] | | | |
| N | 567 | 566 | 1133 |
| Yes | 213 (37.6) | 211 (37.3) | 424 (37.4) |
| No | 354 (62.4) | 355 (62.7) | 709 (62.6) |
| Time since first symptoms (years) at randomization | | | |
| N | 567 | 566 | 1133 |
| Mean | 7.63 | 7.65 | 7.64 |
| SD | 6.781 | 6.782 | 6.779 |
| Median | 5.84 | 5.70 | 5.77 |
| Q1, Q3 | 2.40, 10.97 | 2.24, 11.03 | 2.32, 11.01 |
| Min, Max | 0.2, 40.8 | 0.2, 30.8 | 0.2, 40.8 |
| Number of relapses in last year prior to study entry | | | |
| N | 567 | 565 | 1132 |
| Mean | 1.2 | 1.3 | 1.3 |
| SD | 0.61 | 0.65 | 0.63 |
| Median | 1.0 | 1.0 | 1.0 |
| Q1, Q3 | 1.0, 1.0 | 1.0, 2.0 | 1.0, 1.0 |
| Min, Max | 0, 4 | 0, 5 | 0, 5 |
| Multiple sclerosis subtype [n (%)] | | | |
| N | 567 | 566 | 1133 |
| RRMS | 552 (97.4) | 552 (97.5) | 1104 (97.4) |
| SPMS | 15 (2.6) | 14 (2.5) | 29 (2.6) |
| Presence of Gd + T1 lesions at baseline (from central reader) [n (%)] | | | |
| N | 567 | 564 | 1131 |
| Yes | 226 (39.9) | 256 (45.4) | 482 (42.6) |
| No | 341 (60.1) | 308 (54.6) | 649 (57.4) |
| Volume of T2 lesions at baseline [mm3] (from central reader) | | | |
| N | 565 | 563 | 1128 |
| Mean | 8301.4 | 9489.2 | 8894.3 |
| SD | 10346.28 | 11265.42 | 10826.32 |
| Median | 4841.3 | 5651.0 | 5171.7 |
| Q1, Q3 | 1679.6, 11004.4 | 2022.9, 12978.7 | 1851.3, 11754.1 |
| Min, Max | 0, 86053 | 0, 82776 | 0, 86053 |
| Highly active disease [n (%)] | | | |
| N | 567 | 566 | 1133 |
| Yes | 202 (35.6) | 200 (35.3) | 402 (35.5) |
| No | 365 (64.4) | 366 (64.7) | 731 (64.5) |

(a)DMT = MS disease-modifying treatment.

RRMS = Relapsing-remitting multiple sclerosis, SPMS = Secondary progressive multiple sclerosis.

1.3 Extent of Exposure

The mean treatment exposure (irrespective of interruptions) was 96.7 weeks in the ponesimod 20 mg arm and 97.5 weeks in the teriflunomide 14 mg arm. The cumulative exposure to ponesimod 20 mg was 1045 subject-years and was 1057 subject-years for teriflunomide 14 mg arm.

TABLE 5

Study treatment exposure
Analysis Set: Safety Set

| | Ponesimod 20 mg N = 565 | Teriflunomide 14 mg N = 566 |
|---|---|---|
| Treatment exposure, irrespective of interruptions (weeks) | | |
| N | 564 | 566 |
| Mean | 96.69 | 97.45 |
| SD | 29.018 | 27.022 |
| Median | 108.00 | 108.00 |
| Q1, Q3 | 107.29, 108.71 | 107.29, 108.57 |
| Min, Max | 0.3, 111.3 | 0.1, 113.0 |
| Treatment exposure, irrespective of interruptions | | |
| N | 564 | 566 |
| Cumulative exposure (years) | 1045.2 | 1057.1 |

Treatment exposure based on study drug log. Treatment duration only presented for subjects with available complete treatment end date. Interruptions derived based on study drug log and number of capsules taken.

2. Primary Endpoint Analysis

Primary efficacy endpoint: Ponesimod 20 mg statistically significantly reduced ARR (confirmed relapses) up to EOS by 30.5% compared to teriflunomide 14 mg (ARR=0.202 for ponesimod 20 mg vs. 0.290 for teriflunomide 14 mg, rate ratio: 0.695 [99% CL: 0.536:0.902], p=0.0003). The primary endpoint results are robust, all sensitivity and supplementary analyses are in line with the primary analysis.

A relapse is defined as new, worsening or recurrent neurological symptoms that occur at least 30 days after the onset of a preceding relapse, and that last at least 24 hours, in the absence of fever or infection.

The new, worsening or recurrent neurological symptoms were evaluated by the treating neurologist and, if all the elements of the above definition were verified, and in the absence of another, better explanation of the subject's symptoms, the event was considered as a relapse. The onset date of the relapse corresponded to the onset date of the symptoms.

A relapse was confirmed by the treating neurologist only when the subjects' symptoms were accompanied by an increase in EDSS/FS (functional system) scores, which were consistent with the subject's symptoms, from a previous clinically stable EDSS/FS assessment (i.e., performed at least 30 days after the onset of any previous relapse), obtained by the efficacy assessor and consistent with the following:

An increase of at least half a step (0.5 points; unless EDSS=0, then an increase of at least 1.0 points is required) or An increase of at least 1.0 point in at least two FS scores, or An increase of at least 2.0 points in at least one FS score (excluding bladder/bowel and cerebral).

The primary statistical analysis was performed up to EOS on the FAS using a negative binomial regression model for confirmed relapses, with treatment as a factor and the binary stratification variables (EDSS≤3.5 versus EDSS>3.5; DMTs within last 2 years prior to randomization [Yes/No]) and the number of relapses in the year prior to study entry (categories≤1 (or missing) and >2) included in the model. The model also included an offset variable defined as the log of time on study (in years) from randomization up to EOS.

Ponesimod 20 mg statistically significantly reduced ARR (confirmed relapses) up to EOS by 30.5% compared to teriflunomide 14 mg (ARR=0.202 for ponesimod 20 mg vs. 0.290 for teriflunomide 14 mg, rate ratio: 0.695 [99% CL: 0.536:0.902], p=0.0003).

Figure 7:
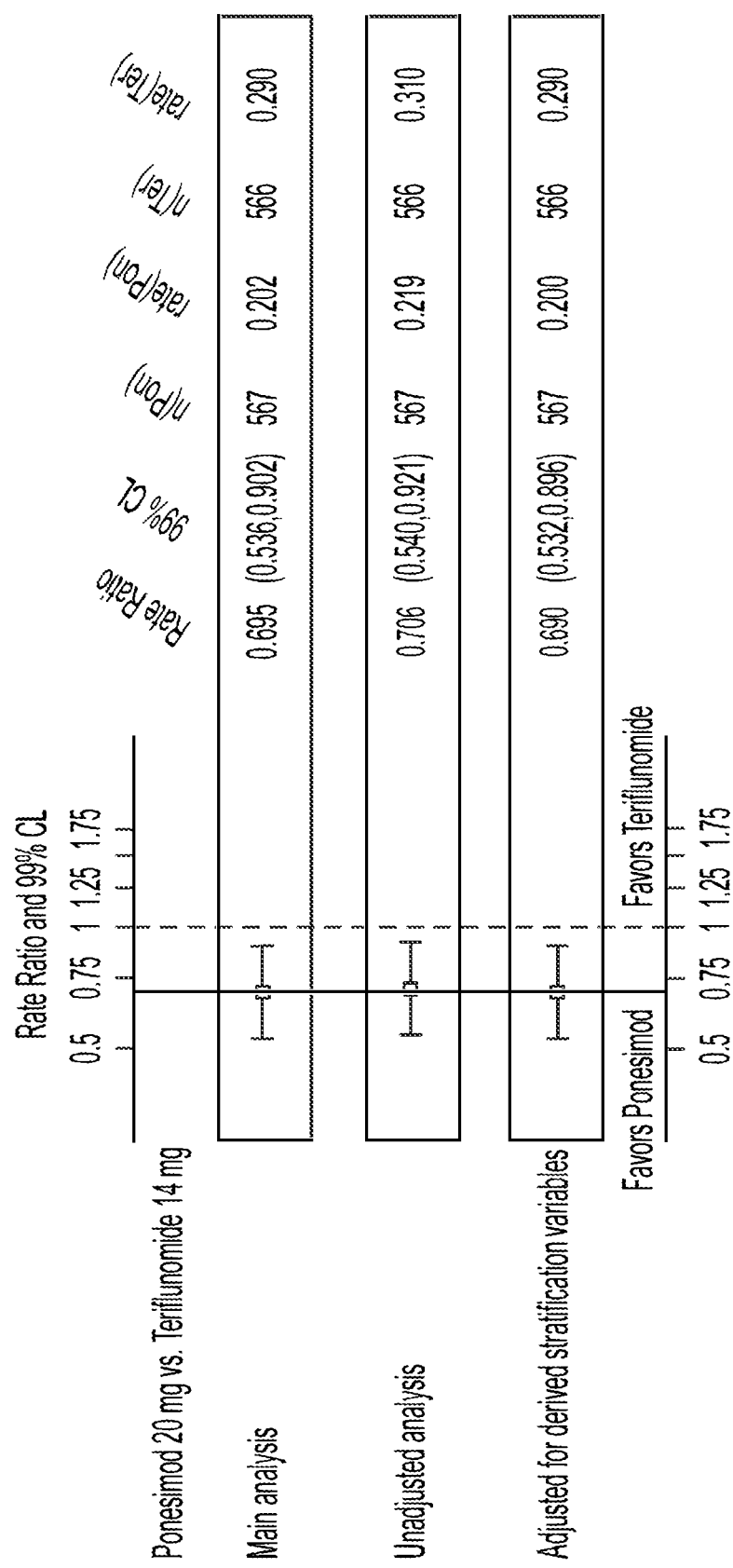
FIG. 7 is a Forest plot (with 99% CL) showing an overview of primary and sensitivity analyses for confirmed relapses up to EOS (Analysis Set: Full Analysis Set).
Figure 8:
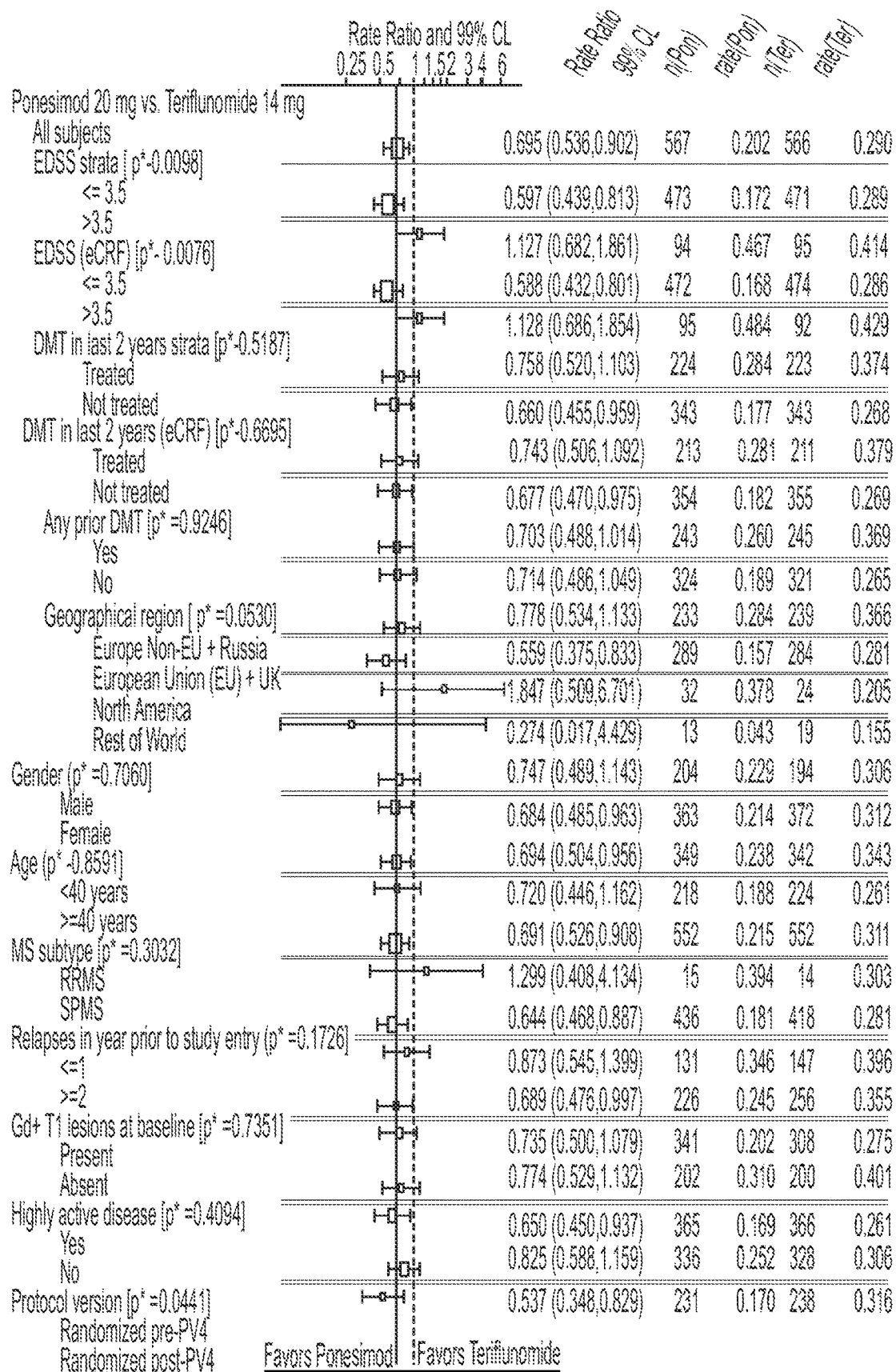
FIG. 8 is a Forest plot (with 99% CL) showing subgroup analyses of confirmed relapses up to EOS (Analysis Set: Full Analysis Set).

The primary endpoint results were robust; all sensitivity (see FIG. 7) and supplementary analyses (see FIG. 2A) are in line with the primary analysis. Subgroup analysis [see FIG. 8], shows most notably that there appears to be a treatment-by-EDSS stratum interaction.

TABLE 6

Confirmed relapses up to EOS—ARR from negative binomial regression (Primary analysis)
Analysis Set: Full Analysis Set

| | Ponesimod 20 mg N = 567 | Teriflunomide 14 mg N = 566 |
|---|---|---|
| Mean estimate (ARR) | 0.202 | 0.290 |
| 99% CL | (0.165, 0.246) | (0.244, 0.345) |
| 95% CL | (0.173, 0.235) | (0.254, 0.331) |
| Treatment effect (rate ratio) | 0.695 | |
| 99% CL | (0.536, 0.902) | |
| 95% CL | (0.570, 0.848) | |
| p-value | 0.0003 | |
| Dispersion estimate | 0.765 | |
| Number of subjects included in analysis | 567 | 566 |
| Total number of relapses | 242 | 344 |
| Total time (years) | 1119 | 1137 |
| Raw ARR | 0.216 | 0.303 |

3. Secondary Endpoint(S) Main Analyses 3.1 Fatigue—Change from Baseline to Week 108 in FSIQ-RMS Weekly Symptoms Score Change from baseline to Week 108 in the FSIQ-RMS weekly symptoms score, based on the full analysis set, was statistically significantly lower in the ponesimod 20 mg arm compared with teriflunomide 14 mg, based on an MMRM analysis (mean=−0.01 for ponesimod 20 mg vs. 3.56 for teriflunomide 14 mg, mean difference: −3.57 [95% CL: −5.83: −1.32], p=0.0019, an increase from baseline indicates worsening in fatigue symptoms). See FIG. 3A.

Figure 3B:
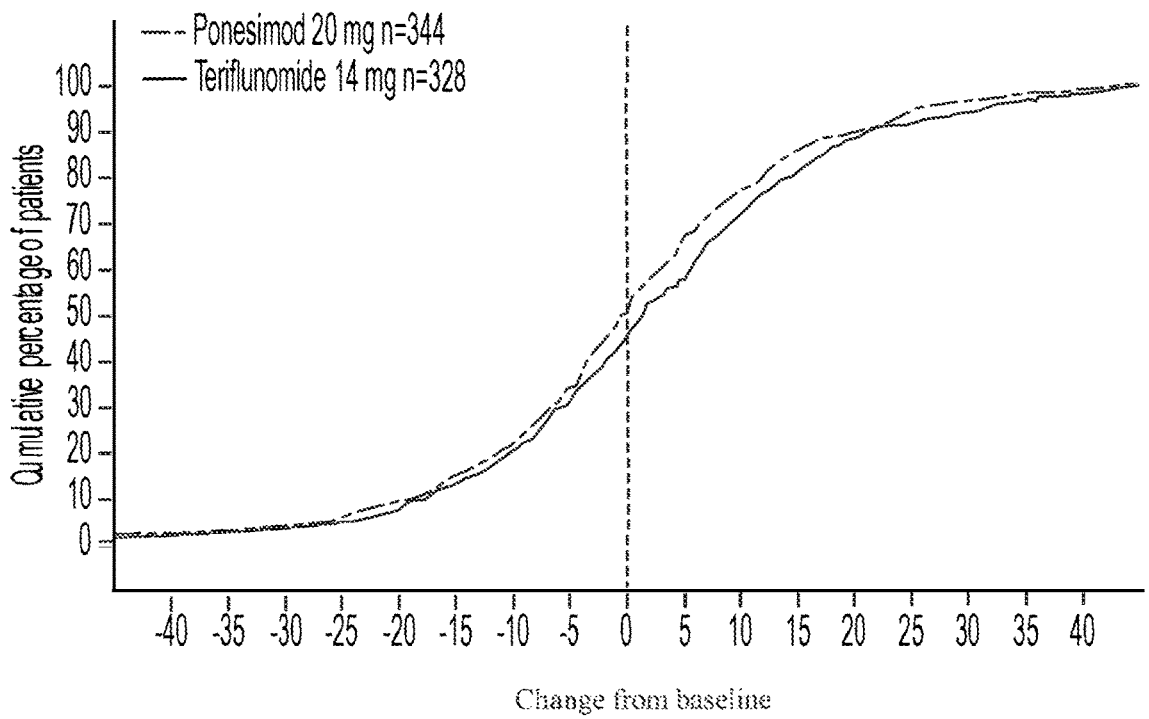
FIG. 3B shows cumulative distribution function of change from baseline at week 108 for the FSIQ-RMS weekly symptoms score.

Cumulative distribution function of change is shown in FIG. 3B. Results of the study are summarized below in Table 6A. In addition to the observation of statistical significance at the group level change from baseline favoring ponesimod, there is also observed a statistically significant difference in patients who were stable or improved on ponesimod compared to teriflunomide. This suggests a statistically significant and clinically meaningful difference for ponesimod at the patient level.

TABLE 6A

Summary of Change from Baseline to Week 108 for FSIQ-RMS Weekly Symptoms Score Based on Full Analysis Set.

| Visit | Change in FSIQ-RMS-S: Total Score | N | Ponesimod | N | Teriflunomide | P-Value |
|---|---|---|---|---|---|---|
| Week 108 | Improved (<−6.3) | 105 | 30.5% | 98 | 29.9% | 0.5163 |
| | Stable (−6.3 < x < +6.3) | 132 | 38.4% | 107 | 32.6% | |
| | Stable or Improved | 237 | 68.9% | 205 | 62.5% | 0.045 |
| | Worsened (≥6.3) | 107 | 31.1% | 123 | 37.5% | |

The FSIQ-RMS is an MS specific 20-item PRO measure that comprises 2 domains: one measuring MS symptoms and one measuring MS-related impacts. The symptoms domain of the scale was used in this study to compare the effect of ponesimod and teriflunomide on fatigue. This new tool has a number of advantages compared to the available fatigue tools for MS. See Hudgens S, et al., *Development and Validation of the FSIQ-RMS: A New Patient-Reported Questionnaire to Assess Symptoms and Impacts of Fatigue in Relapsing Multiple Sclerosis. Value Health.* 2019 April; 22(4):453-466. doi: 10.1016/j.jval.2018.11.007. Epub 2019 Feb. 21. PubMed PMID: 30975397. With 7 symptom items and 13 impact items (in 3 impacts subdomains: physical, cognitive and emotional, and coping), the FSIQ-RMS is a comprehensive, valid, and reliable measure of fatigue-related symptoms and impacts in RMS patients.

The FSIQ-RMS symptom domain (FSIQ-RMS-S) consists of seven items assessing fatigue-related symptoms with a recall period of 24 hours measured on an 11-point numeric rating scale; the standardized symptom domain score ranges from 0 to 100 with a higher score indicating greater fatigue. This domain (i.e., section 1 of the questionnaire) is completed on 7 consecutive days.

The FSIQ-RMS impact domain (FSIQ-RMS-I) consists of 13 items assessing impacts of fatigue-related symptoms with a recall period of 7 days measured on a 5-point verbal descriptor scale, ranging from no impact to extreme impact; the impact domain score ranges from 0 to 100 with a higher score indicating greater impact. As the impact domain of the FSIQ-RMS (i.e., section 2 of the questionnaire) has a 7-day recall period, it was completed on the last day (i.e., seventh day) of completion of section 1.

FSIQ-RMS was completed during the pre-randomization period, at Visits 6, 7, 10, and 12 (Weeks 12, 24, 60, 84), 14 (EOT), and at unscheduled visits due to relapses (R1, R2, etc.) or other unscheduled visits (U1, U2, etc.) as described below. If applicable, FSIQ-RMS was performed at the corresponding visits in the PTOP.

The completion of the FSIQ-RMS during the pre-randomization period was done as follows: At Visit 1 (Screening), subjects who appear eligible based on the assessments made during this visit (but prior to the results from the laboratory assessments are received) were provided with the electronic device containing the FSIQ-RMS.

Once the results from the laboratory assessments confirmed the subject's eligibility, and provided no other assessment performed in the meantime excluded the subject, the site coordinator contacted and asked the subject to start the completion of the FSIQ-RMS. At home, the subject completed the symptom domain of the FSIQ-RMS for 7 days (i.e., section 1 of the questionnaire). On the seventh day, the subject completed the impact domain of the FSIQ-RMS (i.e., section 2 of the questionnaire). The information captured from this assessment was used as the baseline data for the FSIQ-RMS. Ideally, the FSIQ-RMS was completed during the 7 consecutive days preceding the randomization.

After randomization, the symptoms domain of the FSIQ-RMS (i.e., section 1 of the questionnaire) was completed by the subject at home on a daily basis, starting in the evening of the day of a visit when the FSIQ-RMS was administered (Day 1 of questionnaire administration cycle) and during the 6 subsequent days (i.e., over 7 days in total). Subjects returned the completed FSIQ-RMS diary at the next scheduled visit. On the seventh day, the subject completed the impact domain of the FSIQ-RMS (i.e., section 2 of the questionnaire). If applicable, at the end of the PTOP, the FSIQ-RMS was completed prior to Visit 14A (Week 108), ideally, during the 7 consecutive days preceding the visit.

Results for the secondary endpoint of change from baseline to Week 108 in the symptoms domain of the FSIQ-RMS (assessed over a 7-day period) have shown the superiority of ponesimod 20 mg over teriflunomide 14 mg.

3.2 MRI—Combined Unique Active Lesions (CUAL) from Baseline to Week 108.

CUAL are new Gd+T1 lesions plus new or enlarging T2 lesions (without double-counting of lesions).

The cumulative number of CUAL is considered a reliable outcome measure of inflammatory MS disease activity. Radiological evidence of disease activity is routinely used to support disease diagnosis and to inform therapeutic decisions targeting no evidence of disease activity (NEDA), clinical (relapses or disability accumulation) or radiological (brain lesions on MRI) perspective. See Lublin F D. *Disease activity free status in MS.* Mult Scler Relat Disord. 2012 January; 1(1):6-7. doi: 10.1016/j.msard.2011.08.001. Epub 2011 Aug. 27. PubMed PMID: 25876444.

MRI scans were performed at Visits 2 (Baseline), 10 (Week 60), and 14 (EOT) and at any unscheduled visit (U1, U2, etc.). If applicable, MRI scans also were performed at the corresponding visits in the PTOP (Visits 10A and 14A). Testing at all visits were performed up to 7 days prior to or after the visit date. In case of premature study treatment discontinuation, the MRI at EOT did not need to be performed if the EOT visit occurred within less than 4 weeks of the MRI assessment at Visit 10 (Week 60).

MRI variables included the number and volume of new and total Gd+ lesions on T1-weighted MRI scans, number of new and enlarging lesions and lesion volume on T2-weighted MRI, and global measures of loss of brain tissue.

Lesion count of MRI performed within 24 months prior to the study were recorded on the MS history page of the eCRF. These scans were not analyzed by the medical image analysis center (MIAC).

T1-weighted imaging before and after i.v. administration of 0.1 mmol/kg body weight (=0.2 mL/kg) of Gd as well as PD-T2-weighted imaging was performed. Gd may cause nausea and vomiting and in very rare cases allergic reactions that could require immediate anti-anaphylactic therapy (such as steroids, epinephrine/adrenaline, etc.).

Ponesimod 20 mg statistically significantly reduced by 56% the number of CUALs between baseline and week 108 compared to teriflunomide 14 mg (mean CUALs per year=1.405 for ponesimod 20 mg vs. 3.164 for teriflunomide 14 mg, rate ratio: 0.44 [95% CL: 0.36:0.54], p<0.0001). A total of 4.9% and 4.9% of subjects had a baseline but no post-baseline MRI; sensitivity analyses using a range of methods (data not shown) for imputation of missing data supported the primary results (p<0.0001 in all cases).

Ponesimod 20 mg was clearly superior in reducing the number of CUALs vs teriflunomide 14 mg, fully supporting and complementing the results of the primary endpoint.

TABLE 7

CUAL from baseline to Week 108—negative binomial regression of lesions per year (Main analysis)
Analysis Set: Full Analysis Set

|  | Ponesimod 20 mg N = 567 | Teriflunomide 14 mg N = 566 |
|---|---|---|
| Mean estimate (Lesions per year) | 1.405 | 3.164 |
| 95% CL | (1.215, 1.624) | (2.757, 3.631) |
| Treatment effect (Rate Ratio) | 0.444 | |
| 95% CL | (0.364, 0.542) | |
| p-value | <0001 | |
| Dispersion estimate | 2.409 | |
| Number of subjects included in analysis | 539 | 536 |
| Total number of lesions | 1671 | 3714 |
| Total time (years) | 1072 | 1067 |
| Raw mean lesions/year | 1.559 | 3.481 |

Mean estimate = CUAL per year, Rate Ratio: ponesimod vs. teriflunomide. Negative binomial model is applied with Wald confidence intervals and p-value. Offset: Log Time (years) up to last MRI scan. Covariates: EDSS strata (<=3.5, >3.5), DMT within last 2 years prior to randomization strata (Y, N), and Gd+ T1 lesions at baseline (absent or present). Subjects with baseline and at least one post-baseline MRI are included in the analysis.

3.3 EDSS—Time to First 12-Week Confirmed Disability Accumulation (CDA)

The 12-week confirmed disability accumulation, also sometimes referred to as disability progression (CDA/CDP) is a common endpoint in RMS studies, while 24-week CDA/CDP is regarded as the more robust and clinically relevant endpoint. See European Medicines Agency, *Guideline on clinical investigation of medicinal products for the treatment of Multiple Sclerosis*, 26 Mar. 2015, EMA/CHMP/771815/2011, Rev. 2, Committee for Medicinal Products for Human Use (CHMP). Teriflunomide 14 mg has shown a statistically significant reduction in the risk of 12-week CDP in the TEMSO and TOWER studies. See O'Connor P, et al. N Engl J Med. 2011; 365:1293-30; Confavreux C, et al.; TOWER Trial Group. *Oral teriflunomide for patients with relapsing multiple sclerosis (TOWER): a randomised, double-blind, placebo-controlled, phase 3 trial.* Lancet Neurol. 2014 March; 13(3):247-56. doi: 10.1016/S1474-4422 (13)70308-9. Epub 2014 Jan. 23. PubMed PMID: 24461574.

A 12-week CDA is an increase of at least 1.5 in EDSS for subjects with a baseline EDSS score of 0.0 or an increase of at least 1.0 in EDSS for subjects with a baseline EDSS score of 1.0 to 5.0, or an increase of at least 0.5 in EDSS for subjects with a baseline EDSS score≥5.5 which is to be confirmed after 12 weeks.

Baseline EDSS is defined as the last EDSS score recorded prior to randomization. The initial EDSS increase, meeting the above criteria, is defined as the onset of disability accumulation.

All EDSS measurements (with or without relapse, at a scheduled or unscheduled visit) were used to determine the onset of disability accumulation. However, EDSS scores used for confirmation of disability accumulation were obtained at a scheduled visit (i.e., unscheduled visits cannot be used as confirmatory visits) outside any ongoing relapse. In this context, relapse duration is defined as period between start and end dates if available and limited to 90 days from onset if end date is not available or duration is longer than 90 days.

In order to confirm that the EDSS increase is persistent, all EDSS measurements between the onset and the 12-week EDSS confirmation (minus 7-day visit time-window) need to show an increase in EDSS, meeting the criteria for accumulation of disability as defined above.

Figure 4:
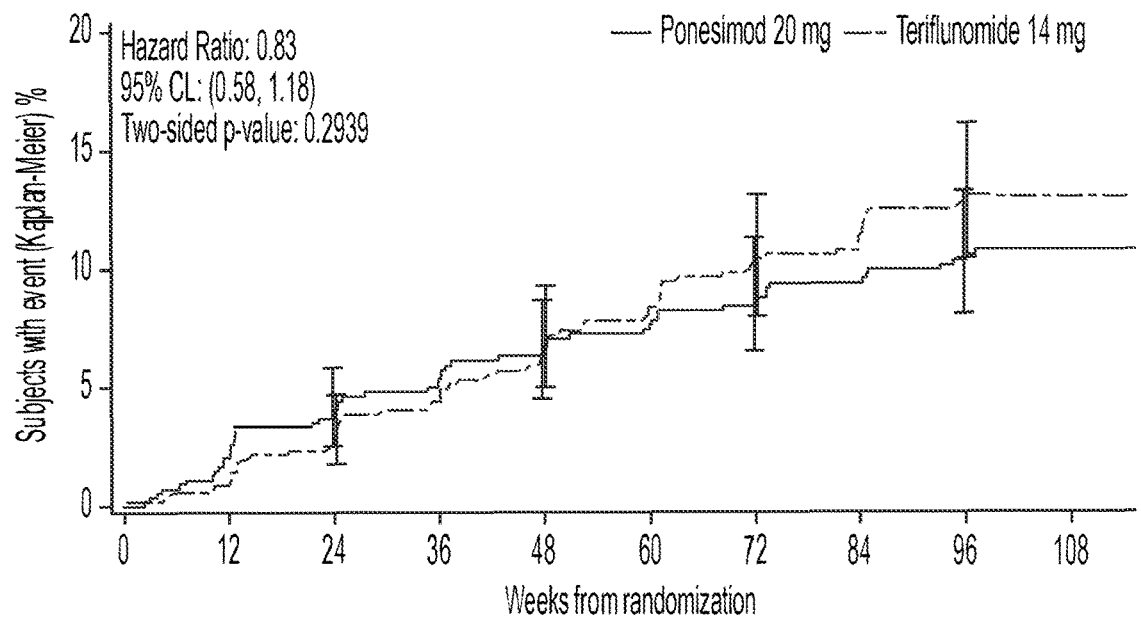
FIG. 4 is a Kaplan-Meier curve (main analysis) showing the time to first 12-week confirmed disability accumulation (CDA) up to end-of-study (EOS): Analysis Set: Full Analysis Set.

A 12-week CDA was observed in 10.1%, and 12.4% of subjects up to EOS in the ponesimod 20 mg and teriflunomide 14 mg arms, respectively. The risk of 12-week CDA was not found to be statistically significantly different for ponesimod 20 mg as compared with teriflunomide 14 mg (hazard ratio: 0.83 [95% CL, 0.58 to 1.18]; log-rank p=0.2939). Consequently, the formal testing procedure was stopped. See Table A3; see also FIG. 4.

TABLE A3

Testing strategy: Overview of secondary endpoint results
Analysis Set: Full Analysis Set

| Endpoint | Effect Measure | Estimate | 95% CL | Alpha available | p-value | Significant |
|---|---|---|---|---|---|---|
| FSIQ-RMS change from baseline to Week 108 | Mean difference | −3.57 | −5.83, −1.32 | 0.0167 | 0.0019 | Yes |
| CUAL from baseline to Week 108 | Rate ratio | 0.44 | 0.36, 0.54 | 0.0333 | <.0001 | Yes |
| Time to first 12-week CDA | Hazard ratio | 0.83 | 0.58, 1.18 | 0.0500 | 0.2939 | No |
| Time to first 24-week CDA | Hazard ratio | 0.84 | 0.57, 1.24 | 0.0000 | 0.3720 | NA |

CUAL = Combined unique active lesions; CDA = Confirmed disability accumulation; NA = Not applicable.
Effect measures display results of Ponesimod 20 mg vs. Teriflunomide 14 mg.
Alpha available = Alpha available as per testing strategy for testing the corresponding endpoint.

3.4 EDSS—Time to First 24-Week Confirmed Disability Accumulation (CDA)

Figure 5:
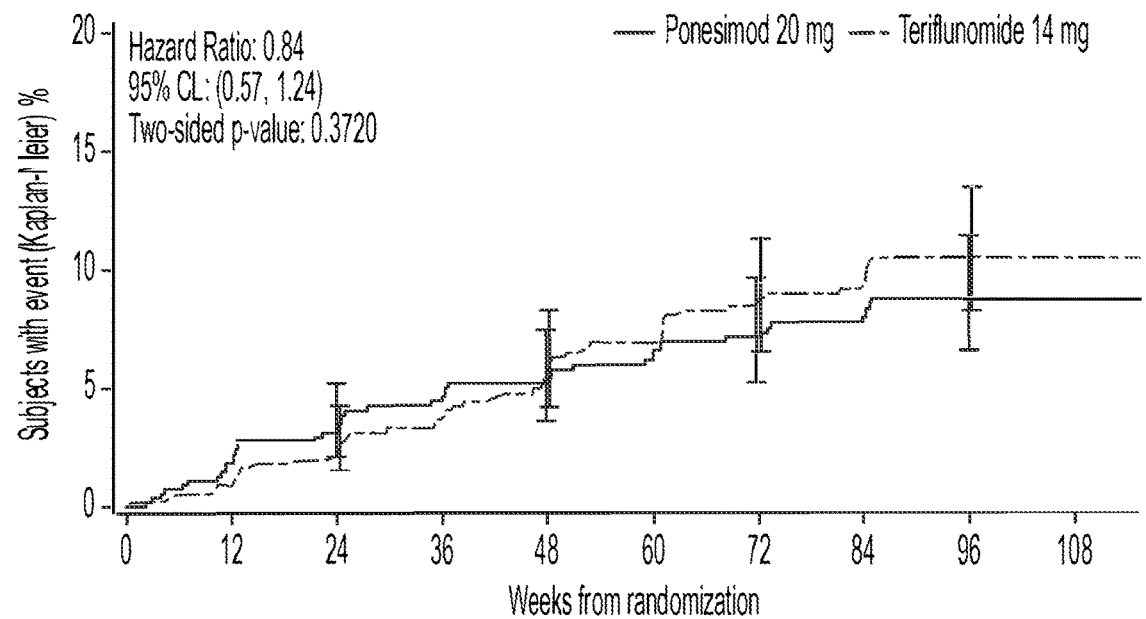
FIG. 5 is a Kaplan-Meier curve (Main analysis) showing the time to first 24-week CDA up to EOS: Analysis Set: Full Analysis Set.

24-week CDA was not formally tested and only evaluated in an exploratory manner. A 24-week CDA was observed in 8.1%, and 9.9% of subjects up to EOS in the ponesimod 20 mg and teriflunomide 14 mg arms, respectively. The risk of 24-week CDA for ponesimod 20 mg as compared with teriflunomide 14 mg was not found to be statistically significantly different at a nominal $\alpha=0.05$ (hazard ratio: 0.84 [95% CL, 0.57 to 1.24]; log-rank p=0.3720). See FIG. 5.

A 24-week CDA is an increase of at least 1.5 in EDSS for subjects with a baseline EDSS score of 0.0 or an increase of at least 1.0 in EDSS for subjects with a baseline EDSS score of 1.0 to 5.0, or an increase of at least 0.5 in EDSS for subjects with a baseline EDSS score≥5.5 which is to be confirmed after 24 weeks.

Baseline EDSS is defined as the last EDSS score recorded prior to randomization. The initial EDSS increase, meeting the above criteria, is defined as the onset of disability accumulation.

All EDSS measurements (with or without relapse, at a scheduled or unscheduled visit) were used to determine the onset of disability accumulation. However, EDSS scores used for confirmation of disability accumulation were obtained at a scheduled visit (i.e., unscheduled visits cannot be used as confirmatory visits) outside any ongoing relapse. In this context, relapse duration is defined as period between start and end dates if available and limited to 90 days from onset if end date is not available or duration is longer than 90 days.

In order to confirm that the EDSS increase is persistent, all EDSS measurements between the onset and the 24-week EDSS confirmation (minus 7-day visit time-window) need to show an increase in EDSS, meeting the criteria for accumulation of disability as defined above.

In this study, ponesimod 20 mg reduced by 17% and 16% the risk of 12- and 24-week CDA, respectively, compared to teriflunomide 14 mg, however, the difference did not reach statistical significance. This study was not powered for 12- or 24-week CDA, so results were not bound to be statistically different.

4. Safety 4.1 Summary of All Adverse Events

An overview of treatment emergent AEs (TEAEs) is presented in Table 8.

TABLE 8

Overview of treatment-emergent adverse events (AE)
Analysis Set: Safety Set

| Characteristic Subject with at least one | Ponesimod 20 mg N = 565 n (%) | Teriflunomide 14 mg N = 566 n (%) |
|---|---|---|
| AE | 502 (88.8) | 499 (88.2) |
| Severe AE | 39 (6.9) | 26 (4.6) |
| Drug-Related AE | 278 (49.2) | 238 (42.0) |
| AE leading to study drug discontinuation | 49 (8.7) | 34 (6.0) |
| Serious AE | 49 (8.7) | 46 (8.1) |
| Fatal AE | 0 | 2 (0.4) |

Overall, the proportion of subjects who experienced at least one TEAE was similar in both treatment arms (88.8% and 88.2% of subjects in the ponesimod 20 mg and the teriflunomide 14 mg arms, respectively).

The most common TEAEs in the ponesimod 20 mg arm were ALT increased (19.5%), nasopharyngitis (19.3%), headache (11.5%) and upper respiratory tract infection (10.6%). The most common TEAEs in the ponesimod 20 mg arm were ALT increased (19.5% vs 9.4% in the teriflunomide arm), nasopharyngitis (19.3% vs 16.8%), headache (11.5% vs 12.7%) and upper respiratory tract infections (10.6% vs 10.4%).

TEAEs leading to premature treatment discontinuation were reported in 8.7% of ponesimod 20 mg subjects compared to 6.0% of teriflunomide 14 mg subjects [see Table 9]. While the number of events was low, the difference in the type of AEs leading to treatment discontinuation was mainly driven by anticipated class effects on respiratory system and macular edema. No infections led to permanent study treatment discontinuation in the study.

TABLE 9

Treatment-emergent AEs leading to premature discontinuation of study drug by SOC
Analysis Set: Safety Set

| System Organ Class | Ponesimod 20 mg N = 565 n (%) | Teriflunomide 14 mg N = 566 n (%) |
|---|---|---|
| Subjects with at least one AE | 49 (8.7) | 34 (6.0) |
| Investigations | 12 (2.1) | 10 (1.8) |
| Respiratory, thoracic and mediastinal disorders | 7 (1.2) | 0 |
| Eye disorders | 5 (0.9) | 0 |
| Gastrointestinal disorders | 4 (0.7) | 4 (0.7) |
| Blood and lymphatic system disorders | 3 (0.5) | 2 (0.4) |
| General disorders and administration site conditions | 3 (0.5) | 2 (0.4) |
| Hepatobiliary disorders | 3 (0.5) | 2 (0.4) |
| Pregnancy, puerperium and perinatal conditions | 3 (0.5) | 3 (0.5) |
| Vascular disorders | 3 (0.5) | 0 |
| Nervous system disorders | 2 (0.4) | 4 (0.7) |
| Social circumstances | 2 (0.4) | 1 (0.2) |
| Cardiac disorders | 1 (0.2) | 2 (0.4) |
| Musculoskeletal and connective tissue disorders | 1 (0.2) | 1 (0.2) |
| Neoplasms benign, malignant and unspecified (incl cysts and polyps) | 1 (0.2) | 1 (0.2) |
| Psychiatric disorders | 1 (0.2) | 1 (0.2) |
| Skin and subcutaneous tissue disorders | 1 (0.2) | 2 (0.4) |
| Reproductive system and breast disorders | 0 | 1 (0.2) |
| Surgical and medical procedures | 0 | 1 (0.2) |

System Organ Classes are based on MedDRA version 21.0. SOCs are sorted by descending order of frequency in the ponesimod arm.

There were two deaths reported in the study, one due to coronary artery insufficiency and one due to multiple sclerosis. Both deaths occurred in subjects receiving teriflunomide 14 mg.

The proportion of subjects who experienced at least one SAL was similar in both treatment arms (8.7% and 8.1% of subjects in the ponesimod 20 mg and the teriflunomide 14 mg arms, respectively).

An overview of ALs of special interest (ALSIs) addressing anticipated risks of ponesimod is presented in Table 10. The most common ALSIs were reported for category hepatobiliary disorders/liver enzyme abnormality (25.7% vs 14.5% in ponesimod 20 mg compared to teriflunomide 14 mg, respectively), followed by category hypertension (10.1% vs 9.0%), and pulmonary events (8.0% vs 2.7%).

TABLE 10

Treatment-emergent AESIs by category
Analysis Set: Safety Set

| AESI Category | Ponesimod 20 mg N = 565 n (%) | Teriflunomide 14 mg N = 566 n (%) |
| --- | --- | --- |
| Hepatobiliary disorders/ Liver enzyme abnormality | 145 (25.7) | 82 (14.5) |
| Hypertension | 57 (10.1) | 51 (9.0) |
| Pulmonary events | 45 (8.0) | 15 (2.7) |
| Effect on heart rate and rhythm (including hypotension) | 29 (5.1) | 24 (4.2) |
| Herpetic infection | 27 (4.8) | 27 (4.8) |
| Infection | 9 (1.6) | 5 (0.9) |
| Seizure | 8 (1.4) | 1 (0.2) |
| Macular edema | 6 (1.1) | 1 (0.2) |
| Skin malignancy | 5 (0.9) | 1 (0.2) |
| Non-skin malignancy | 1 (0.2) | 1 (0.2) |

Categories are sorted by descending order of frequency in the ponesimod 20 mg arm. AESI - Adverse Event of Special Interest. Infection AESI are identified by the AEs from the Infections and Infestations SOC, only if reported as serious or severe.

The proportion of subjects who experienced ALT increase >3×ULN was higher in the ponesimod arm (17.3%) compared to teriflunomide (8.3%) whereas ALT increase >8×ULN was higher in the teriflunomide arm (2.1%) compared to ponesimod (0.7%). Based on the individual case review, most ALT/AST increases ≥3×ULN occurred as a single transient asymptomatic episode, resolving with continued treatment or after protocol mandated treatment discontinuation. All but one case of bilirubin increase ≥2×ULN occurred in subjects with pre-treatment bilirubin increases. One case of potential Hy's law occurred in a subject with pre-existing transaminase elevation (ALT>5×ULN), and the event fully resolved within 2 weeks after treatment discontinuation.

The incidence of treatment-emergent heart rate and rhythm (including hypotension) AESIs on Day 1 was higher in the ponesimod 20 mg arm (2.1%) than in the teriflunomide 14 mg arm (0.4%). See Table 10A. However, the overall incidence of first dose AESI on Day 1 was low (2.1%) in ponesimod. None of these events were serious nor led to permanent discontinuation of study treatment. Discharge criteria at 4 hours post-dose were met for ca. 99% of subjects. No 2nd or higher degree AV block was observed. ECG HR effect: nadir at 2 hours post-dose (siponimod—3-4 hours, fingolimod—around by 6 hours). Low incidence of low HR outliers (post-dose HR 40 bpm), all 3 of them with a pre-treatment HR of <55 bpm, which is a known risk factor for post-dose bradycardia with S1P receptor modulators.

Figure 6:
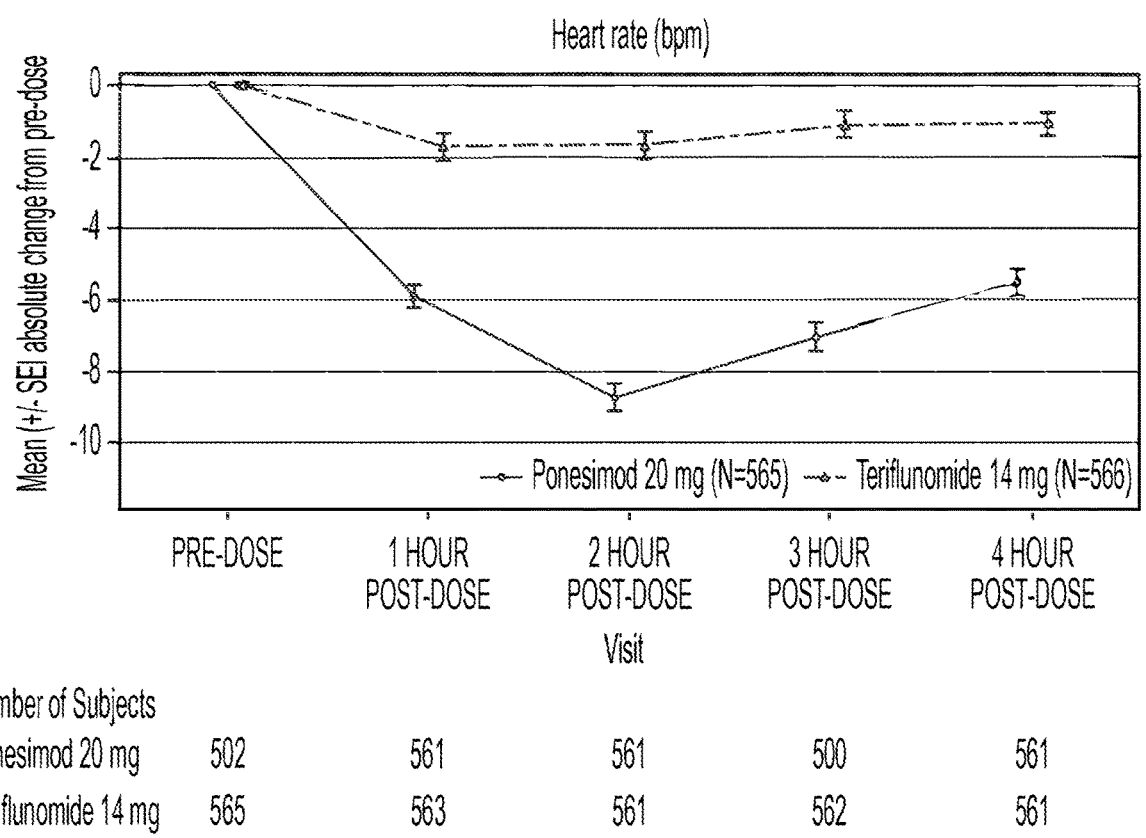
FIG. 6 shows the 12-lead electrocardiogram (ECG) heart rate and absolute change from pre-dose at Day 1, by hour (Analysis Set: Safety Set). As per up-titration regimen, the dose of ponesimod on Day 1 is 2 mg.

The mean heart rate reduction compared to pre-dose reached a maximum for ponesimod 20 mg at 2-hours post dose, −8.7 bpm compared to −1.7 bpm for teriflunomide 14 mg (FIG. 6). There were 3 subjects with asymptomatic post-dose HR≤40 bpm in the ponesimod 20 mg arm (none on teriflunomide 14 mg); all of these subjects had a pre-treatment HR<55 bpm, which would require post-dose monitoring according to regulatory precedence of siponimod [Mayzent® USPI].

Example 1A: FSIQ-RMS and Physical, Cognitive, and Coping Impact

TABLE 10A

Treatment-emergent AESI by PT: Effect on heart rate and rhythm (including hypotension) on Day 1
Analysis Set: Safety Set

| Preferred Term | Ponesimod 20 mg N = 565 n (%) | Teriflunomide 14 mg N = 566 n (%) |
| --- | --- | --- |
| Subjects with at least one AE | 12 (2.1) | 2 (0.4) |
| Bradycardia | 4 (0.7) | 0 |
| Atrioventricular block first degree | 3 (0.5) | 0 |
| Defect conduction intraventricular | 2 (0.4) | 0 |
| Bundle branch block left | 1 (0.2) | 0 |
| Bundle branch block right | 1 (0.2) | 0 |
| Sinus arrhythmia | 1 (0.2) | 0 |
| Sinus bradycardia | 1 (0.2) | 0 |
| Electrocardiogram QT prolonged | 0 | 1 (0.2) |
| Presyncope | 0 | 1 (02) |

Preferred Terms are based on MedDRA version 21.0.
Preferred terms are sorted by descending order of frequency in the ponesimod arm.
AESI - Adverse Event of Special Interest Change from baseline to Week 108 for the physical, cognitive/emotional and coping impacts sub-domains of FSIQ-RMS are shown in FIG. 9, FIG. 10 and FIG. 11, respectively.

Figure 9:
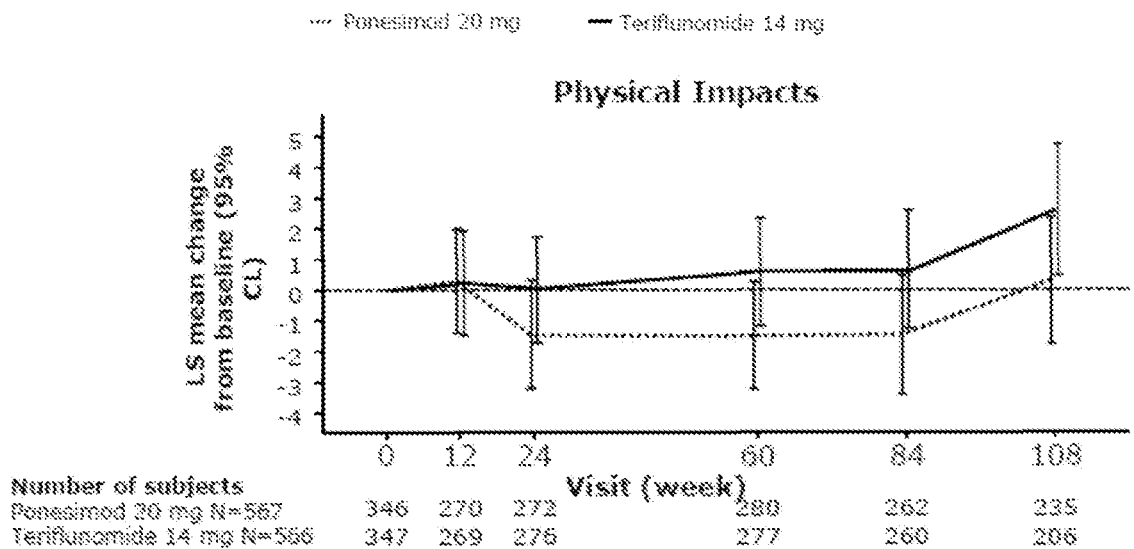
FIG. 9 shows change from baseline to week 108 in the FSIQ-RMS for the physical impact sub-domain.
Figure 10:
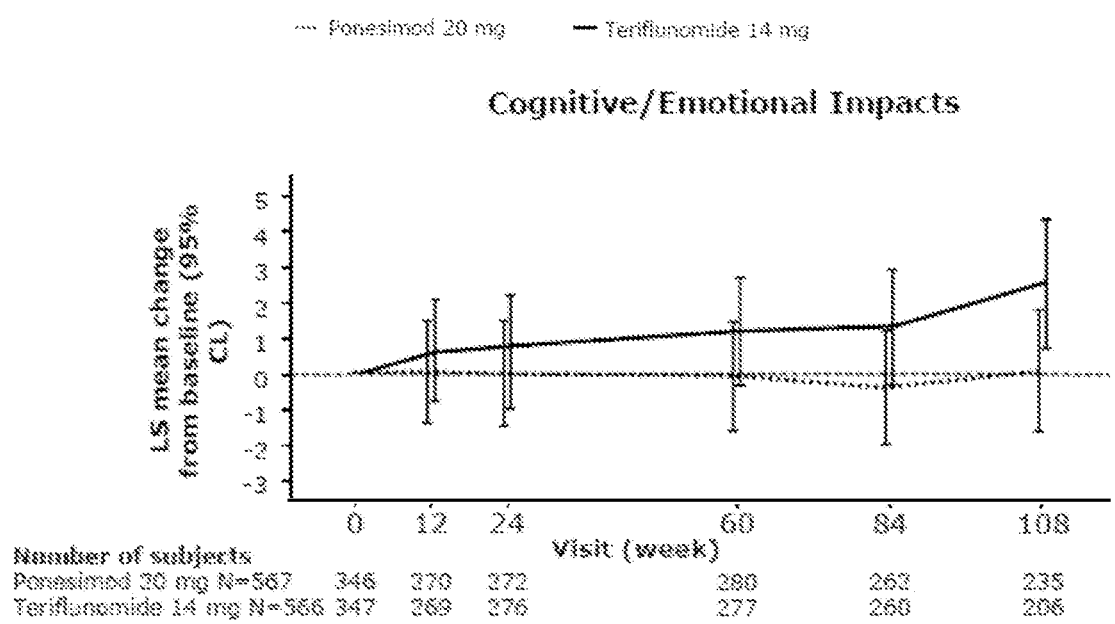
FIG. 10 shows change from baseline to week 108 in the FSIQ-RMS for the cognitive/emotional impacts sub-domain.
Figure 11:
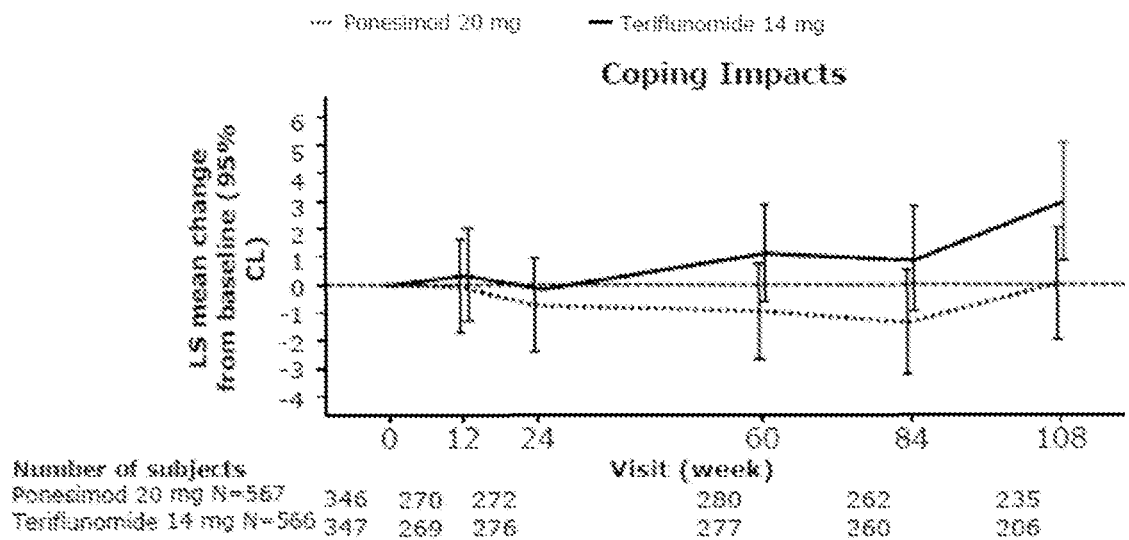
FIG. 11 shows change from baseline to week 108 in the FSIQ-RMS for the coping impact sub-domain.

FIGS. 9, 10 and 11 show the FSIQ-RMS physical, cognitive/emotional and coping impacts sub-domains at the group level, based on the full analysis set, for the ponesimod 20 mg treatment arm and the teriflunomide 14 mg treatment arm.

Example 1B: Change From Baseline to Week 108—Baseline Fatigue Below the Median

Figure 12:
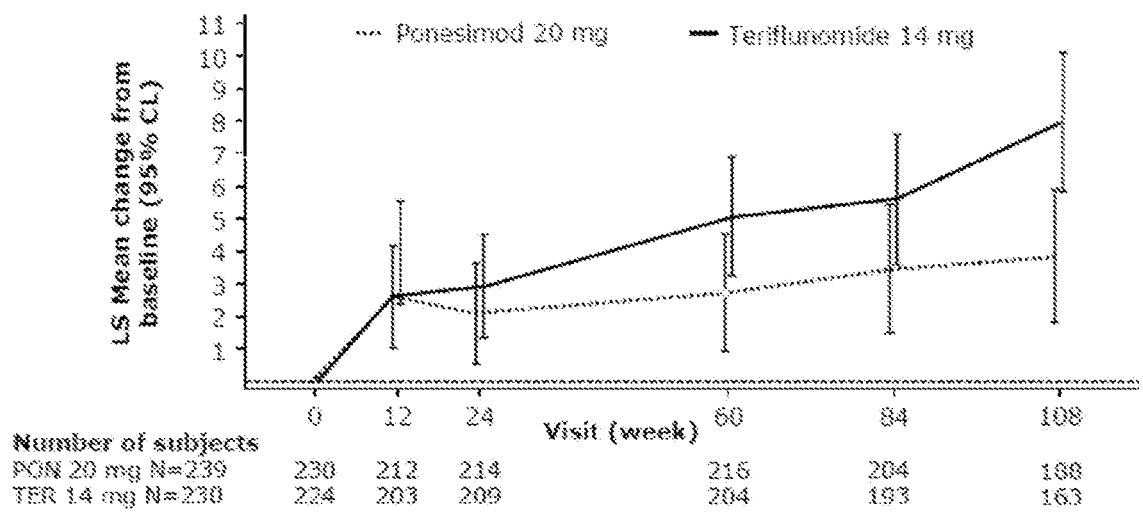
FIG. 12 shows change from baseline to week 108 in FSIQ-RMS weekly symptoms score for patients with baseline fatigue below the median.
Figure 13:
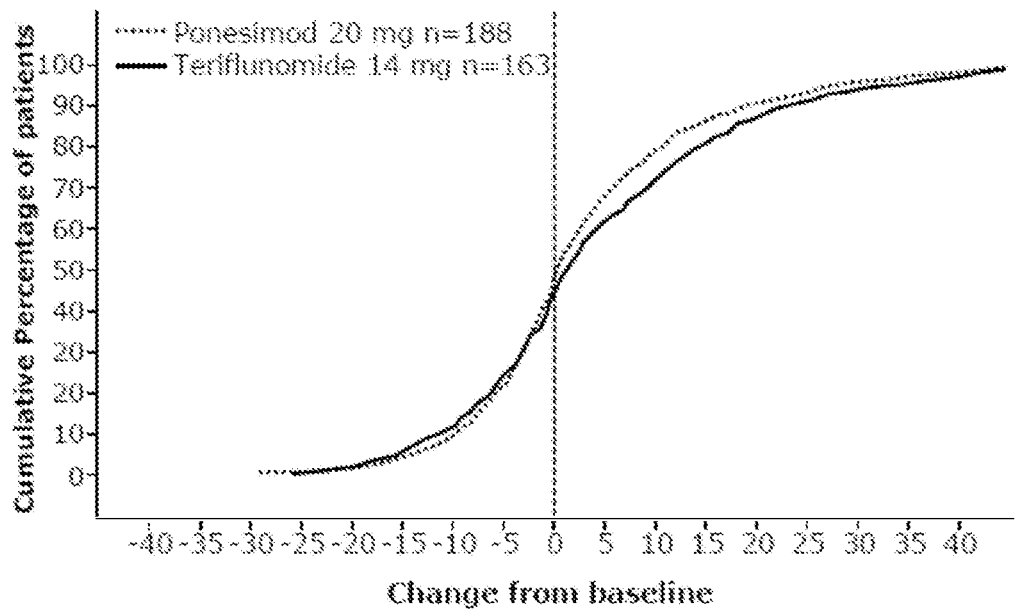
FIG. 13 shows cumulative distribution function of change from baseline at week 108 in FSIQ-RMS weekly symptoms score for patients with baseline fatigue below the median.

Mean change from baseline to Week 108 in FSIQ-RMS weekly symptoms score for patients with baseline fatigue below the median is shown in FIG. 12. Cumulative distribution function of change is shown in FIG. 13. Results are summarized in Table 11A below. Baseline fatigue (i.e., weekly symptoms score at baseline) is provided in Table 11B and was used for the baseline fatigue below the median in this Example and the baseline fatigue above the median in Example 1C.

Almost 65% of low baseline fatigue patients remained stable or improved over the 108 weeks on ponesimod, as compared to about 55% over the 108 weeks on teriflunomide.

TABLE 11A

Change From Baseline to Week 108, Baseline Fatigue
Below the Median for Ponesimod and Teriflunomide

| Visit | Change From Baseline to Week 108: Baseline Fatigue Below the Median | N | Ponesimod | N | Teriflunomide | P-Value |
|---|---|---|---|---|---|---|
| WEEK 108 | Improved (<−6.3) | 36 | 19.1% | 34 | 20.9% | 0.736 |
|  | Stable (−6.3 < x < +6.3) | 85 | 45.2% | 55 | 33.7% |  |
|  | Stable or Improved | 121 | 64.4% | 89 | 54.6% | 0.088 |
|  | Worsened (≥6.3) | 67 | 35.6% | 74 | 45.4% |  |

TABLE 11B

Baseline fatigue (symptoms score of FSIQ at baseline).

|  | Ponesmiod | Teriflunomide |
|---|---|---|
| Minimum | 0.0 | 0.0 |
| Q1 | 14.49 | 17.93 |
| Median | 30.41 | 30.71 |
| Q3 | 46.33 | 46.33 |
| Maximum | 95.40 | 88.40 |

Example 1C: Change from Baseline to Week 108—Baseline Fatigue Above the Median

Figure 14:
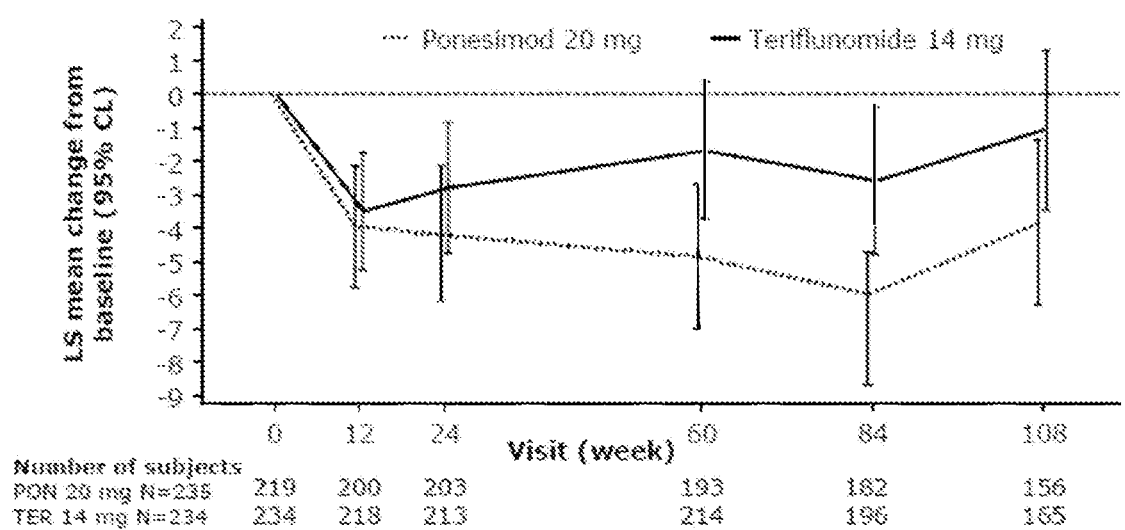
FIG. 14 shows change from baseline to week 108 in FSIQ-RMS weekly symptoms score for patients with baseline fatigue above the median.
Figure 15:
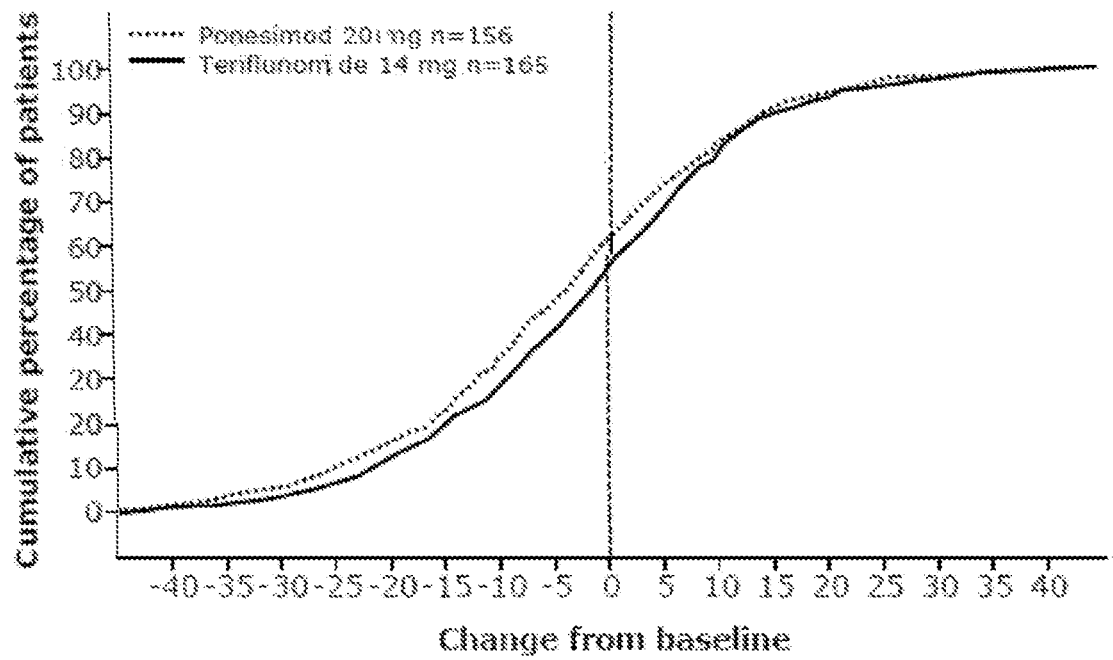
FIG. 15 shows cumulative distribution function of change from baseline at week 108 in FSIQ-RMS weekly symptoms score for patients with baseline fatigue above the median.

Mean change from baseline to Week 108 in FSIQ-RMS weekly symptoms score for patients with baseline fatigue above the median is shown in FIG. 14. Cumulative distribution function of change is shown in FIG. 15.

Figure 16:
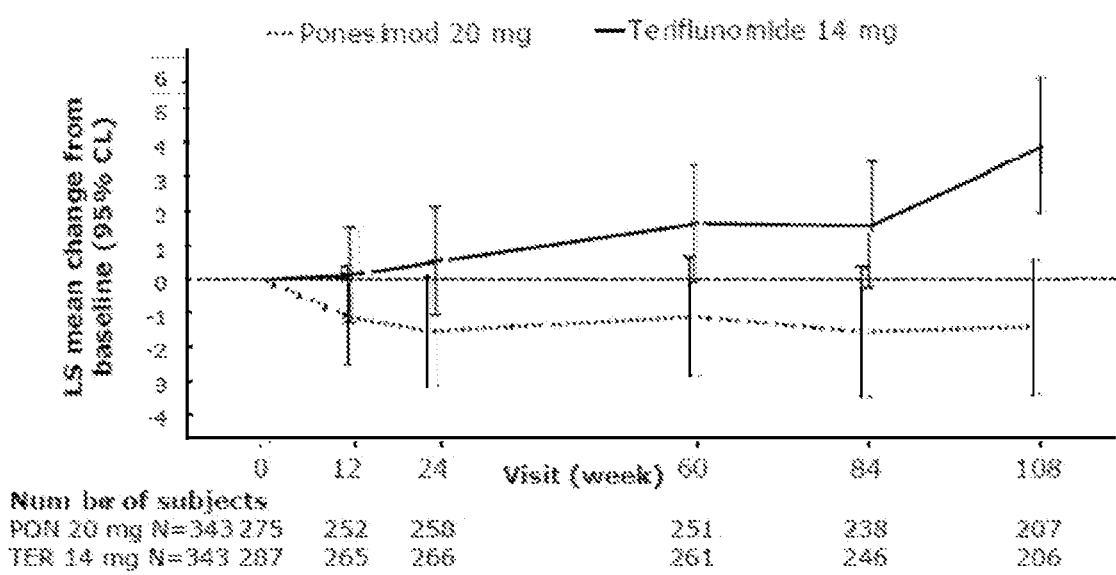
FIG. 16 shows change from baseline to week 108 in FSIQ-RMS weekly symptoms score for patients without DMT treatment two years prior to randomization.
Figure 17:
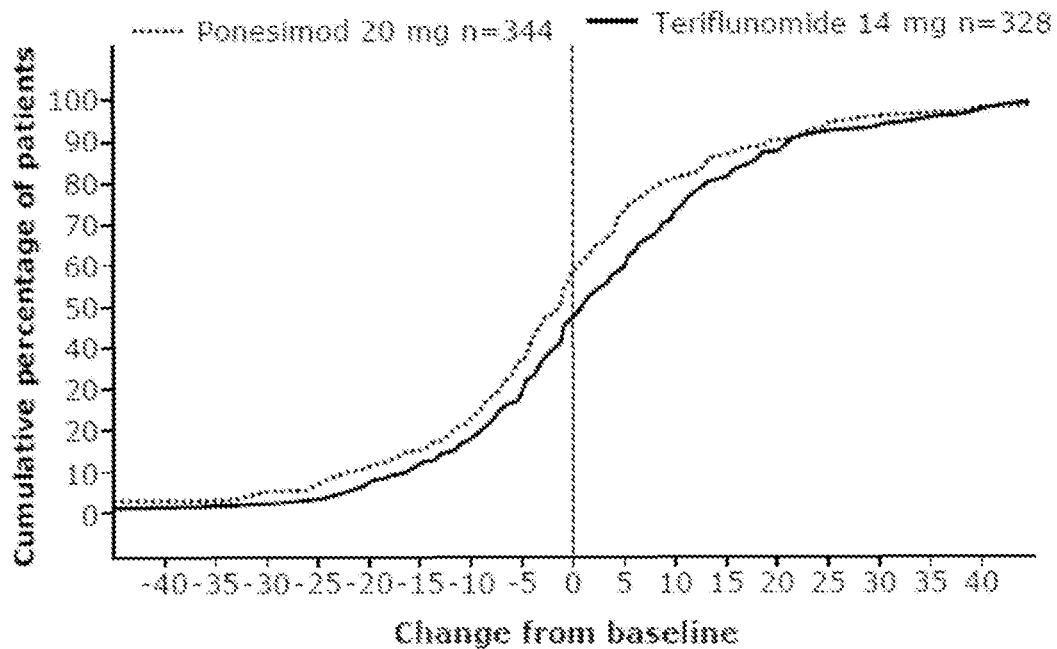
FIG. 17 shows cumulative distribution function of change from baseline at week 108 in FSIQ-RMS weekly symptoms score for patients without DMT treatment two years prior to randomization.

Example 1D: Change From Baseline to Week 108—Patients with No Prior DMT Treatment Mean change from baseline to Week 108 in FSIQ-RMS weekly symptoms score for patients with no prior DMT treatment within about two years prior to initiation of treatment is shown in FIG. 16. Cumulative distribution function of change is shown in FIG. 17. Results are summarized in Table 12 below.

Patient improvement was clinically meaningful in 31.4% of patients on ponesimod (P=0.052), and about 75% of patients on ponesimod remained stable or improved by Week 108 (P=0.003).

TABLE 12

Change From Baseline to Week 108 in Patients with no
Prior DMT Treatment for Ponesimod and Teriflunomide

| Visit | Change From Baseline to Week 108: No Prior DMT Treatment | N | Ponesimod | N | Teriflunomide | P-Value |
|---|---|---|---|---|---|---|
| Week 108 | Improved (<−6.3) | 65 | 31.4% | 54 | 26.2% | 0.052 |
|  | Stable (−6.3 < x < +6.3) | 91 | 44.0% | 76 | 36.9% |  |
|  | Stable or Improved | 156 | 75.4% | 130 | 63.1% | 0.003 |
|  | Worsened (≥6.3) | 51 | 24.6% | 76 | 36.9% |  |

Figure 18:
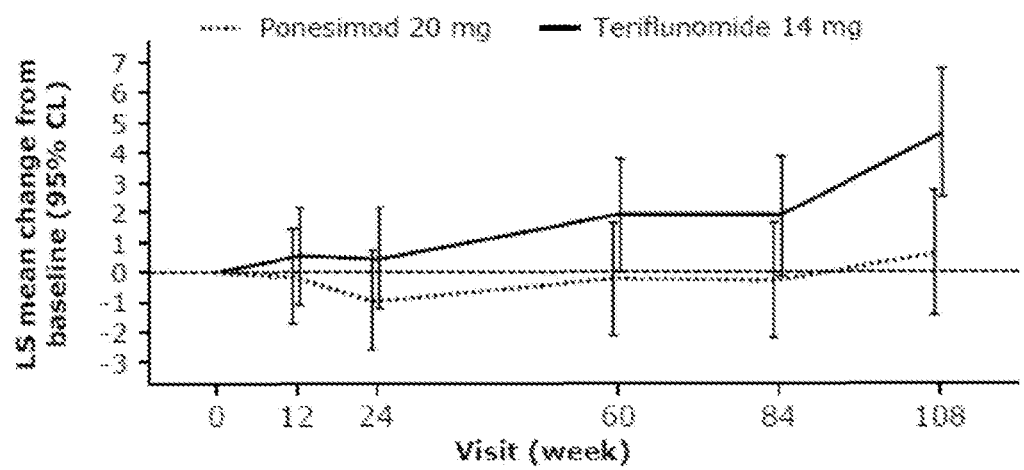
FIG. 18 shows change from baseline to week 108 in FSIQ-RMS weekly symptoms score for patients without Gd+/T1 lesions at baseline.
Figure 19:
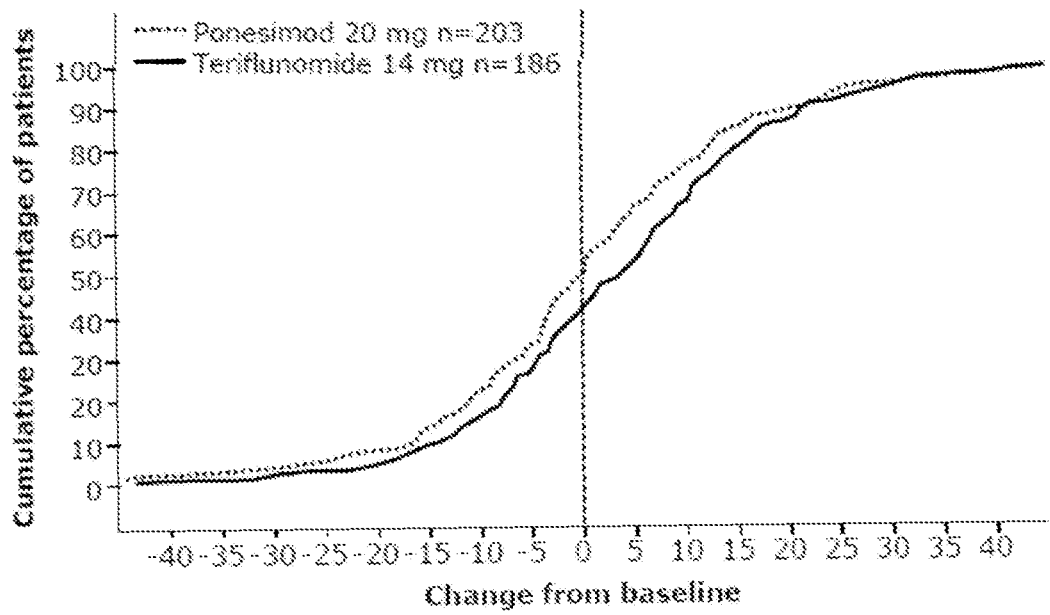
FIG. 19 shows cumulative distribution function of change from baseline at week 108 in FSIQ-RMS weekly symptoms score for patients without Gd+/T1 lesions at baseline.

Example 1E: Change from Baseline to Week 108 in Patients without Gd+T1 Lesions at Baseline Mean change from baseline to Week 108 for change in FSIQ-RMS weekly symptoms score in patients without Gd+T1 lesions at baseline is shown in FIG. 18. Cumulative distribution function of change is shown in FIG. 19. Results are summarized in Table 13 below.

Patients who had stable or improved symptoms of fatigue without baseline Gd+T1 lesions demonstrated a statistically significant difference for ponesimod compared to teriflunomide, about 68% for ponesimod vs. about 57% for teriflunomide (p=0.021).

TABLE 13

Change From Baseline to Week 108 in Patients without Gd + T1 Lesions at Baseline

| Visit | Change From Baseline to Week 108: No Gd + T1 Lesions | N | Ponesimod | N | Teriflunomide | P-Value |
|---|---|---|---|---|---|---|
| Week 108 | Improved (<−6.3) | 61 | 30.0% | 48 | 25.8% | 0.257 |
|  | Stable (−6.3 < x < +6.3) | 76 | 37.4% | 58 | 31.2% |  |

TABLE 13-continued

Change From Baseline to Week 108 in Patients without Gd + T1 Lesions at Baseline

| Visit | Change From Baseline to Week 108: No Gd + T1 Lesions | N | Ponesimod | N | Teriflunomide | P-Value |
|---|---|---|---|---|---|---|
| | Stable or Improved | 137 | 67.5% | 106 | 57.0% | 0.021 |
| | Worsened (≥6.3) | 66 | 32.5% | 80 | 43.0% | |

Figure 20:
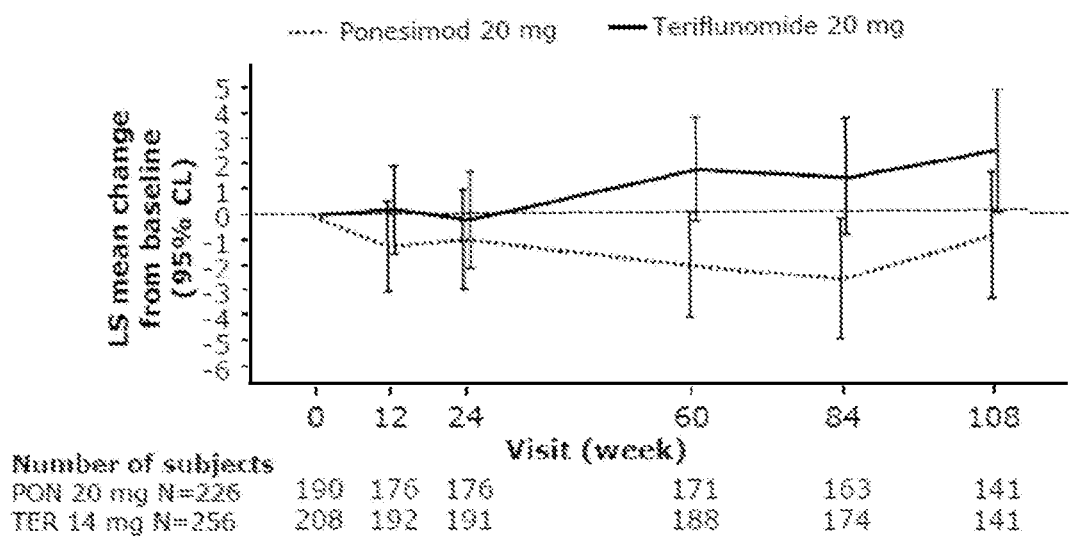
FIG. 20 shows change from baseline to week 108 in FSIQ-RMS weekly symptoms score for patients with Gd+/T1 lesions at baseline.
Figure 21:
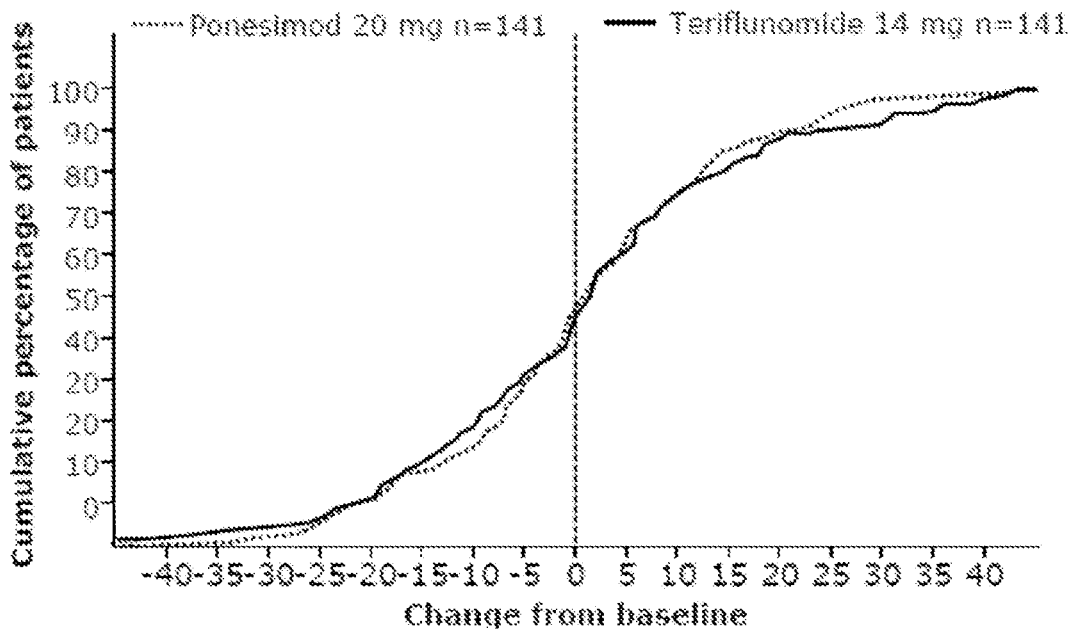
FIG. 21 shows cumulative distribution function of change from baseline at week 108 in FSIQ-RMS weekly symptoms score for patients with Gd+/T1 lesions at baseline.

Example 1F: Change from Baseline to Week 108 in Patients with Gd+T1 Lesions at Baseline Mean change from baseline to Week 108 for change in FSIQ-RMS weekly symptoms score in patients with Gd+T1 lesions at baseline is shown in FIG. 20. Cumulative distribution function of change is shown in FIG. 21.

Example 1G: Change From Baseline to Week 108—Baseline EDSS≤3.5

Figure 22:
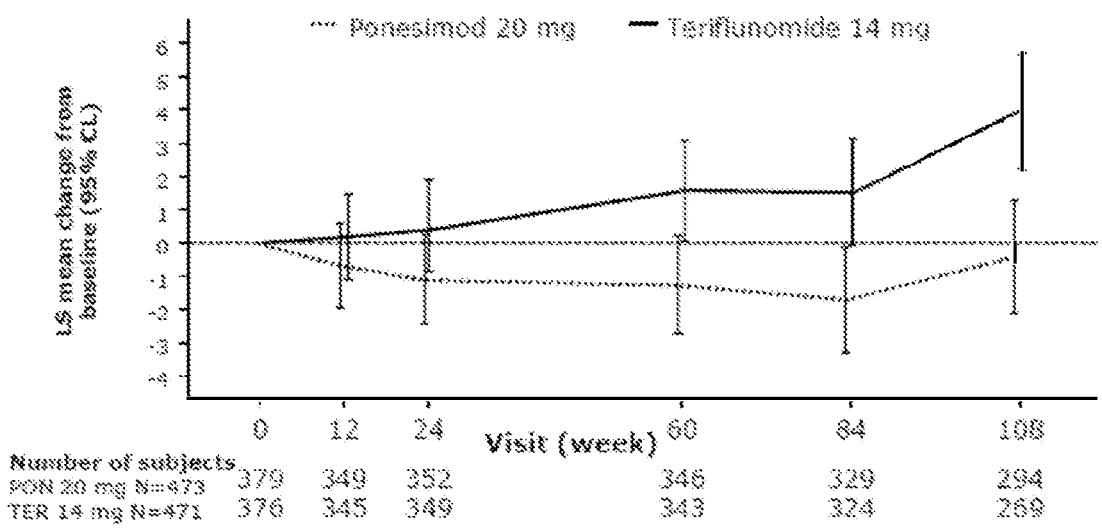
FIG. 22 shows change from baseline to week 108 in FSIQ-RMS weekly symptoms score for patients with baseline EDSS≤3.5.
Figure 23:
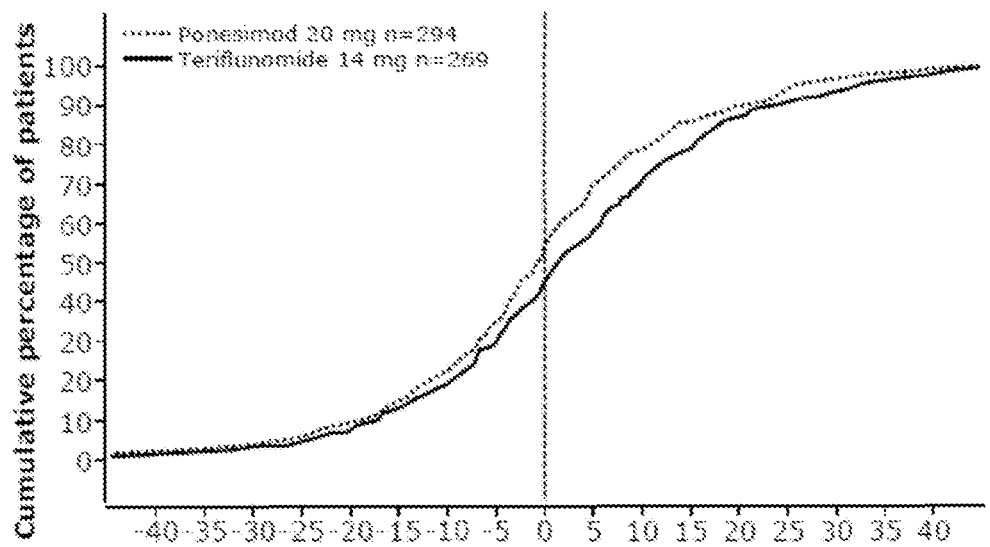
FIG. 23 shows cumulative distribution function of change from baseline at week 108 in FSIQ-RMS weekly symptoms score for patients with baseline EDSS≤3.5.

Mean change from baseline to Week 108 for change in FSIQ-RMS weekly symptoms score for patients with lower baseline EDSS is shown in FIG. 22. Cumulative distribution function of change is shown in FIG. 23. Results are summarized in Table 14 below.

TABLE 14

Change From Baseline to Week 108 in Patients with Baseline EDSS ≤3.5

| Visit | Change From Baseline to Week 108: Baseline EDSS <3.5 | N | Ponesimod | N | Teriflunomide | P-Value |
|---|---|---|---|---|---|---|
| Week 108 | Improved (<−6.3) | 90 | 30.6% | 75 | 27.9% | 0.318 |
| | Stable (−6.3 < x < +6.3) | 120 | 40.8% | 92 | 34.2% | |
| | Stable or Improved | 210 | 71.4% | 167 | 62.1% | 0.010 |
| | Worsened (≥6.3) | 84 | 28.6% | 102 | 37.9% | |

Figure 24:
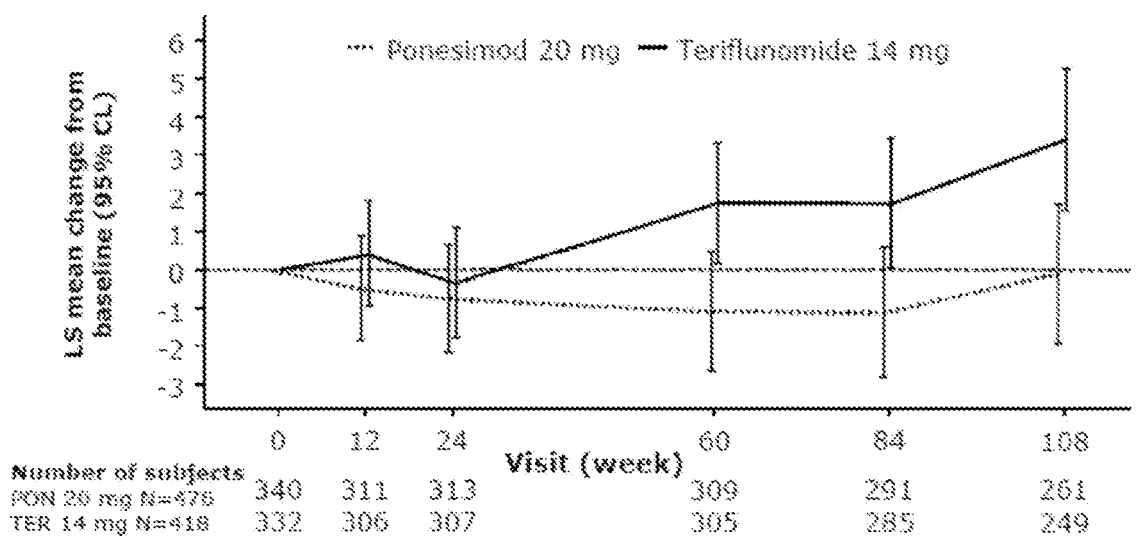
FIG. 24 shows change from baseline to week 108 in FSIQ-RMS weekly symptoms score for patients having one or fewer relapses at baseline.
Figure 25:
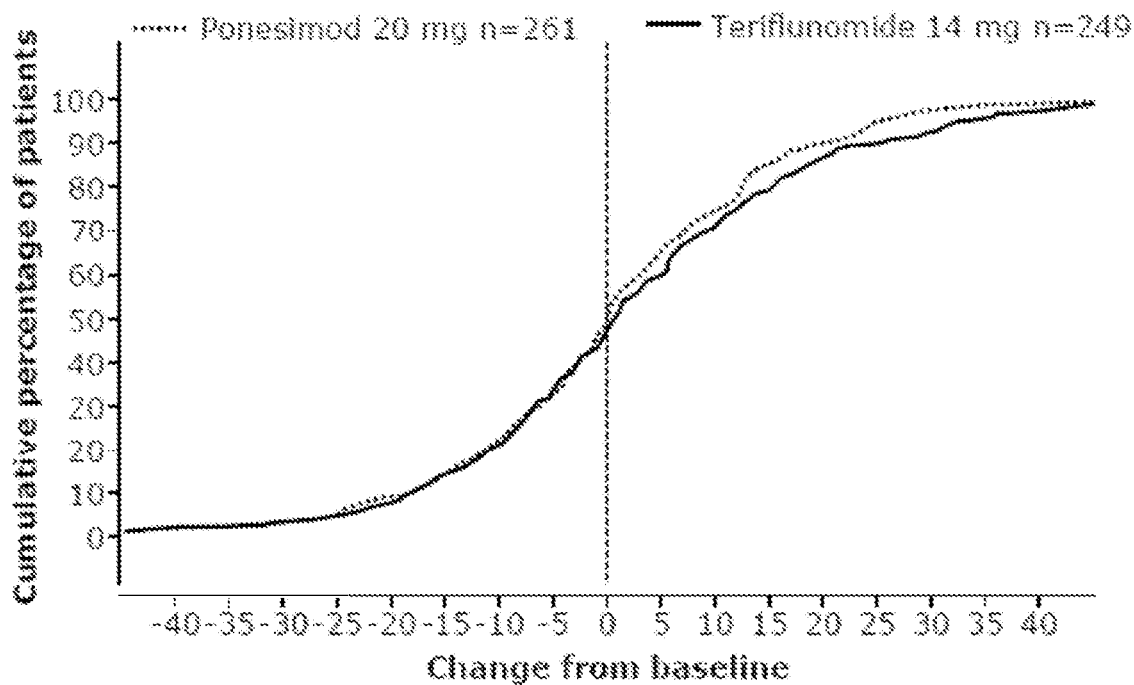
FIG. 25 shows cumulative distribution function of change from baseline at week 108 in FSIQ-RMS weekly symptoms score for patients having one or fewer relapses at baseline.

Example 1H: Change From Baseline to Week 108—Patients with One or Fewer Prior Relapses at Baseline Mean change from baseline to Week 108 for change in FSIQ-RMS weekly symptoms score for patients with one or fewer prior relapses at baseline is shown in FIG. 24. Cumulative distribution function of change is shown in FIG. 25.

Figure 26:
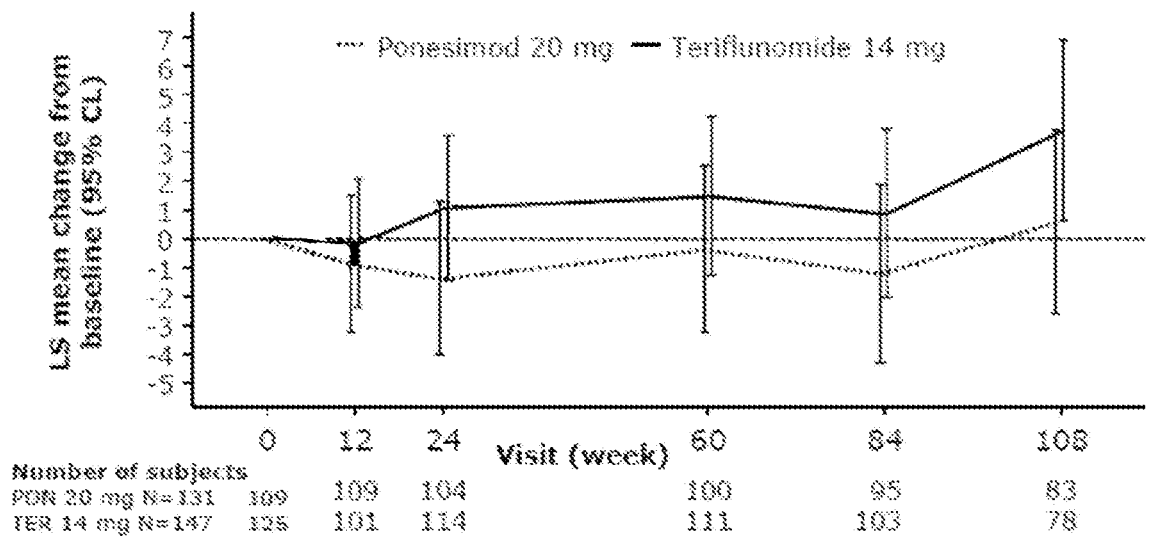
FIG. 26 shows change from baseline to week 108 in FSIQ-RMS weekly symptoms score for patients having two or more relapses at baseline.
Figure 27:
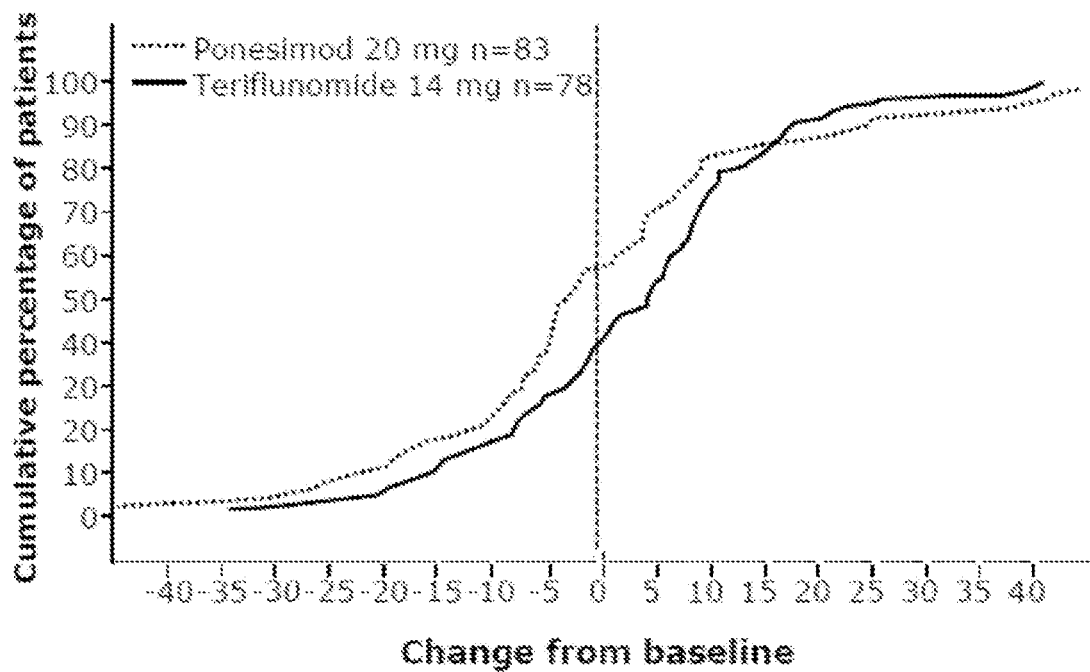
FIG. 27 shows cumulative distribution function of change from baseline at week 108 in FSIQ-RMS weekly symptoms score for patients having two or more relapses at baseline.

Example 1I: Change From Baseline to Week 108—Patients with Two or More Prior Relapses at Baseline Mean change from baseline to Week 108 for change in FSIQ-RMS weekly symptoms score for patients with two or more prior relapses at baseline is shown in FIG. 26. Cumulative distribution function of change is shown in FIG. 27.

Example 2: Pre-Specified MRI Endpoints and No Evidence of Disease Activity (NEDA) Status In this study, prespecified MRI-based endpoints and no evidence of disease activity (NEDA) status is evaluated.

Patients (18-55 years) with RMS (expanded disability status scale scores: 0-5.5) were randomized (1:1) to receive ponesimod (PON) 20 mg or teriflunomide (TER) 14 mg for 108 weeks. MRI assessments were: volume of T2 lesions; mean number of new gadolinium-enhancing (Gd+) T1 lesions and new/enlarging T2 lesions; and absence of active MRI lesions at week 108. NEDA-3 status (absence of confirmed relapse, Gd+T1 lesions and new/enlarging T2 lesions on annual MRIs, and 12-week confirmed disability accumulation) was evaluated from baseline to week 108.

A total of 985/1133 (86.9%) randomized patients completed the study. MRI findings for PON vs TER from baseline to week 108, respectively, were: least square (LS) mean difference (PON-TER) in change from baseline in total volume of T2 lesions: −399.2 mm$^3$ (95% CLs: −651.5; −146.8, p=0.002); mean number of new Gd+T1 lesions per scan: 0.18 vs 0.43 (rate ratio [RR]:0.42, 95% CLs:0.31; 0.56, p<0.0001); mean numbers of new/enlarging T2 lesions per year: 1.40 vs 3.16 (RR:0.44, 95% CLs:0.36; 0.54, p<0.0001); PON vs TER odds ratio (OR [95% CL]) for absence of new Gd+T1 lesions: 2.18 (1.61; 2.95, p<0.0001) and absence of new/enlarging T2 lesions: 1.71 (1.30; 2.25, p=0.0001). At week 108, 28.2% (159/564) PON vs 18.3% (102/558) TER patients (OR: 1.70, CL:1.27; 2.28, p=0.0004) achieved NEDA-3. The most frequent reason for not achieving NEDA-3 status at week 108 was presence of new/enlarging T2 lesions.

Patients treated with ponesimod demonstrated a higher proportion of patients achieving NEDA-3 status compared to those treated with teriflunomide.

Conclusions

This study demonstrates the superior efficacy of ponesimod over the active control. This study is the first study showing a statistically significant effect on fatigue symptoms in a pre-defined secondary endpoint (disease specific validated PRO), targeting a key unmet need.

This study also demonstrates that the safety profile of ponesimod appears to be consistent with previously observed safety findings with ponesimod, and the known safety profile of other S1P receptor modulators. The gradual up-titration appears to successfully mitigate first-dose effects of ponesimod and supports forgoing first dose monitoring for patients with no risk factors for symptomatic bradycardia.

Example 3—Clinical Management

Introduction

Sphingosine-1-phosphate receptor modulators (S1Ps), a class of oral disease modifying therapies (DMTs) for multiple sclerosis (MS), are cell-trafficking inhibitors that have been shown to have high efficacy.

Four S1Ps are indicated for MS in the United States: fingolimod, siponimod, ozanimod, and ponesimod. Although these S1Ps share some similarities as a class, the individual S1Ps have differences in selectivity for receptor subtypes and phosphorylation requirements, half-lives, and safety profiles that result in different clinical requirements before and after treatment initiation.

Some clinical management events are common across the S1Ps, such as complete blood count, electrocardiogram, and liver function tests before treatment initiation. However, each S1P also has unique recommendations for clinical management events described in their US Prescribing Information (USPI), which may impact their overall ease of use. S1Ps with fewer clinical management events may be easier to use than those that require more monitoring.

Objective

The objective of this study was to estimate the expected frequencies of differential clinical management events (eg, eye exam, first-dose cardiovascular monitoring, and drug-drug interactions [DDIs]) using real-world data sources of persons with MS; and to compare the use of SCS for the treatment of relapses between ponesimod (PON) and teriflunomide (TER) groups in the OPTIMUM trial (See Example 1).

Methods

Study Design

Retrospective cohort study utilized the following three US administrative claims databases:
1) IBM® MarketScan® Commercial Claims and Encounters Database (IBM CCAE);
2) IBM® MarketScan® Medicare Supplemental and Coordination of Benefits Database (IBM MDCR); and
3) Optum® Clinformatics® Extended Data Mart—Socioeconomic Status (Optum SES).

Analyses were performed on data converted to the Observational Medical Outcomes Partnership Common Data Model, version 5.3.1.

Inclusion/exclusion criteria: claim for any MS DMT within the index period (1 Jan. 2016-11 Mar. 2019) and no other demyelinating disease diagnosis within 1 year before the index date. The index date was defined as follows:
1) For each patient, identify all DMT service dates within the index period;
2) Retain DMT service dates with prior MS diagnosis between the study period start date (1 Jan. 2015) and the DMT service date;
3) Retain DMT service dates that fall within a continuous observation period spanning at least 1 year before and 1 year after the DMT service date;
4) Retain DMT service dates on which patient is aged≥18 years; and
5) Of any remaining DMT service dates, select the earliest date per patient as the index date.

Only differential events were quantified; common clinical management events that are applicable to all S1Ps were excluded from analysis, including complete blood count, Varicella zoster virus antibody testing, liver function tests (prior to S1P initiation), electrocardiogram, cancer screening, and pulmonary function tests.

Differential clinical management events prior to initiation were first-dose monitoring, genotyping, and an eye exam; after initiation, events were DDIs, eye exam, and liver function tests. The results are summarized below in Table 15.

TABLE 15

Differential Clinical Management Events Up to or After Treatment Initiation

| Event | Fingolimod | Siponimod | Ozanimod | Ponesimod |
|---|---|---|---|---|
| 1$^{st}$ Dose Observation | All Patients | Recommended for Patients with Certain Pre-Existing Cardiac Conditions | N/A | Recommended for Patients with Certain Pre-Existing Cardiac Conditions |
| Eye Exam (Prior to Initiation) | All Patients | All Patients | Recommended for Patients with History of Uveitis, Diabetes Mellitus or Macular Odema | All Patients |
| Genotyping (Prior to Initiation) | N/A | All Patients | N/A | N/A |
| Differential DDIs | Ketoconazole (systemic) | Moderate CYP2C9 inhibitors, moderate CYP2C9 inducers | Adrenergic and serotonergic drugs, BCRP inhibitors, MAO inhibitors, strong CYP2C8 inducers, strong CYP2C8 inhibitors | Strong CYP3A4 inducers, strong UGT1A1 inducers |

TABLE 15-continued

Differential Clinical Management Events Up to or After Treatment Initiation

| Event | Fingolimod | Siponimod | Ozanimod | Ponesimod |
|---|---|---|---|---|
| Eye Exam (3-4 months after initiation) | All Patients | N/A | N/A | N/A |
| Periodic Liver Function Tests During Treatment | All Patients | N/A | N/A | N/A |

S1P, sphingosine-1-phosphate receptor modulator; N/A, not available; DDI, drug-drug interaction; CYP, cytochrome 450; BCRP, breast cancer resistance protein; MAO, monoamine oxidase; UGT, UDP-glucuronosyltransferase.
aAll S1Ps recommend an eye exam at any time if there is any change in vision while on therapy and regular follow-up exams for patients with a history of diabetes or uveitis. Fingolimod differs in additionally requiring an exam 3 to 4 months post initiation for all patients.

Endpoints/Outcomes

Total number of differential clinical management events (first-dose observation, eye exam, DDIs) before and during the first year of treatment for each S1P.

Prevalence of comorbidities for which a first-dose observation is recommended prior to siponimod or ponesimod.

Prevalence of comorbidities (uveitis, macular oedema, diabetes mellitus) for which an eye exam is recommended prior to ozanimod.

Relative risk of DDIs among S1Ps (ie, number of drugs taken concomitantly with any DMT for MS that would result in a DDI when taken with an S1P [excluding DDIs common to all S1Ps]).

Identified were DDI types, removing all DDI classes common to the 4 S1Ps (antineoplastic or immunosuppressive therapies, antiarrhythmic or QT-prolonging drugs, vaccines). Results are summarized below in Table 16.

TABLE 16

USPI Drug Interactions Among S1Ps

| Interactions | Fingolimod | Siponimod[a] | Ozanimod[b] | Ponesimod |
|---|---|---|---|---|
| Antiarrhythmic drugs, QT-prolonging drugs, drugs that slow heart rate[c] | X | X | X | X |
| Antineoplastic, immune-modulating, or immune-suppressive therapies | X | X | X | X |
| Vaccinces | X | X | X | X |
| Adrenergic and serotonergic drugs (e.g., opioid drugs, SSRIs, SNRIs, TCAs, sympathomimetic drugs) | | | X | |
| BCRP Inhibitors | | | X | |
| Lab Test Interaction[d] | X | | | |
| MAO Inhibitors | | | X | |
| Moderate CYP2C9 Inducers | | X | | |
| Moderate CYP2C9 Inhibitors | | X | | |
| Strong CYP2C8 Inducers | | | X | |
| Strong CYP2C8 Inhibitors | | | X | |
| Strong CYP3A4 Inducers | | | | X |
| Strong UGT1A1 Inducers | | | | X |
| Systemic Ketoconazole | X | | | |
| Tyramine[d] | | | X | |

USPI, US Prescribing Information; S1P, sphingosine-1-phosphate receptor modulator; FIN, fingolimod; SIP, siponimod; OZA, ozanimod; PON, ponesimod; SSRI, selective serotonin reuptake inhibitor; SNRI, selective norepinephrine reuptake inhibitor; TCA, tricyclic antidepressant; BCRP, breast cancer resistance protein; MAO, monoamine oxidase; CYP, cytochrome 450; UGT, UDP-glucuronosyltransferase; DDI, drug-drug interaction.
[a]For SIP: 1) Moderate or strong CYP3A4 inhibitors are specified as a DDI only when combined with moderate CYP2C9 inhibitors; here, it is sufficient to identify moderate CYP2C9 inhibitors (including moderate CYP2C9/CYP3A4 dual inhibitors); 2) Strong CYP3A4 inducers are specified as a DDI only when combined with moderate CYP2C9 inducers; here, it is sufficient to identify moderate CYP2C9 inducers (including moderate CYP2C9/strong CYP3A4 dual inducers).
[b]OZA's USPI lists CYP3A4 inhibitors and inducers as DDIs only when combined with other DDI types shown in this table (eg, dual inducers). Thus, for this study, it was not necessary to include these as separate DDI types.
[c]Purple highlighting indicates drug interactions that are common to all S1Ps.
[d]Pharmacogenomic and laboratory test interactions are not in scope for this study, and interactions with foods and over-the-counter medications will not be detectable in the databases.

Results

The majority of patients in all databases were female. The results are summarized in Table 17.

TABLE 17

Cohorts Demographics in Each Database

|  | IBM | IBM MDCR | OPTUM SES |
|---|---|---|---|
| Count | 22,051 | 1,599 | 17,689 |
| Female Patients, % | 76 | 74 | 75 |
| Age, Years, mean (SD) | 48.0 (9.8) | 67.9 (6.3) | 52.8 (11.8) |

IBM CCAE, IBM ® MarketScan ® Commercial Claims and Encounters Database; IBM MDCR, IBM ® MarketScan ® Medicare Supplemental and Coordination of Benefits Database; Optum SES, Optum ® Clinformatics ® Extended Data Mart - Socioeconomic Status; SD, standard deviation.

In the IBM CCAE, ponesimod had the lowest number of differential clinical management events (1.11) compared with fingolimod (4.00), siponimod (2.19), and ozanimod (1.85). The results are summarized in Table 4. Similar results were obtained in the IBM MDCR and Optum SES databases, as shown in FIG. 28.

Figure 28:
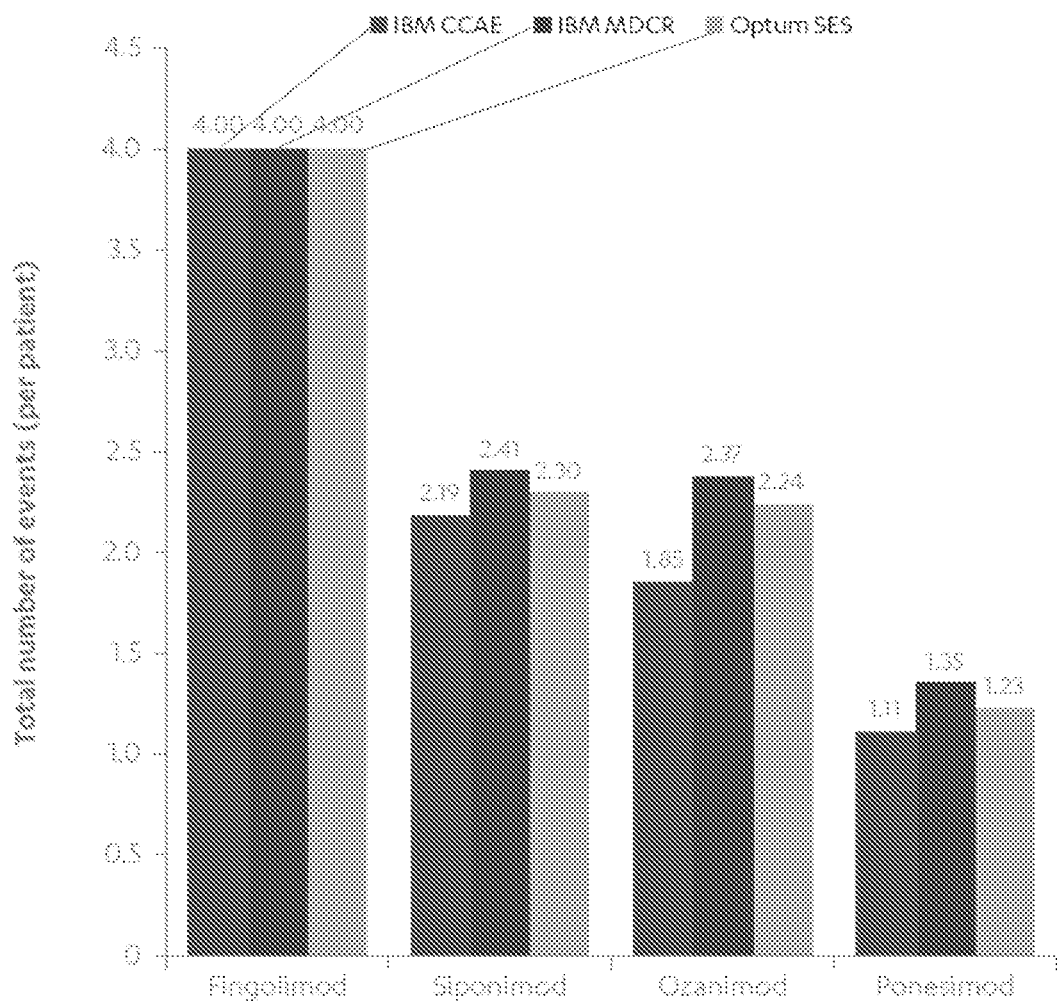
FIG. 28 depicts a bar graph of the total number of differential events in each of the administrative claims databases for each SIP.

In FIG. 28, the IBM CCAE, IBM® MarketScan® Commercial Claims and Insurance Database; IBM MDCR, IBM® MarketScan® Medicare Supplemental and Coordination of Benefits Database; Optum SES, Optum® Clinformatics® Extended Data Mart—Socioeconomic Status. The differential events are management events that have different recommendations for each SIP, such as first-dose monitoring and eye exam.

TABLE 18

Estimated Number of Events of Differential Clinical Management Events per Patient in the IBM CCAE Study Cohort

| Events | Fingolimod | Siponimod | Ozanimod | Ponesimod |
|---|---|---|---|---|
| 1$^{st}$ Dose Monitoring (data on file for all MS patients) | 1 | 0.09 | 0 | 0.09 |
| Eye Exam Before Intitiation | 1 | 1 | 0.09 | 1 |
| Genotyping | 0 | 1 | 0 | 0 |
| DDIs (average number of S1P's differential DDI drugs taken concomitantly with any MS DMT in a 1-year period) | <0.01 | 0.10 | 1.76 | 0.02 |
| Eye Exam, 3-4 Months After Initiation | 1 | 0 | 0 | 0 |
| Periodic Liver Function Tests, After Initiation | 1 | 0 | 0 | 0 |
| Total (Events/Patient) | 4.00 | 2.19 | 1.85 | 1.11 |

Per the USPI, first-dose monitoring is recommended for all patients before fingolimod initiation. The cardiovascular risks described in the USPIs for siponimod and ponesimod were observed in 9% of the IBM CCAE cohort. Thus, first-dose events were quantified as 1 per patient for fingolimod, 0.09 events per patient for siponimod and ponesimod, and 0 events for ozanimod, as shown in Table 18.

An eye exam is recommended for all patients before fingolimod, siponimod, and ponesimod initiation. For ozanimod, 9% of the IBM CCAE cohort had conditions that trigger the recommendation for an eye exam, which translates into 0.09 events per patient for ozanimod and 1 event per patient for the other S1Ps, as shown in Table 4.

In the IBM CCAE, the average number of DDI drugs used concomitantly with any MS DMTs within 1 year was 0.0005, 0.10, 1.76, and 0.02 for fingolimod, siponimod, ozanimod, and ponesimod, respectively, as shown in Table 4.

Per the USPI, periodic liver function tests are recommended during fingolimod treatment, which was estimated as 1 event in the year following initiation, as shown in Table 4.

Limitations

The study design did not include exclusion criteria based on contraindications for each SIP.

The study did not consider differences in recommended first-dose monitoring durations (6 hours for fingolimod and siponimod vs 4 hours for ponesimod) or other differences, such as reversibility of lymphocyte counts.

Generalizability was limited because each database represents a specific population of patients (eg, the IBM CCAE consists of commercially insured individuals, whereas the IBM MDCR includes those who receive supplemental Medicare coverage).

Administrative claims data lack clinical detail; a claim for a filled prescription does not indicate whether the medication was taken as prescribed and overlap of drug exposure dates (determined by overlap in drug supply by ≥1 day) may not reflect actual concomitant drug use.

Because of low sample sizes for newer agents, this analysis assessed risk of DDIs (indicated as concomitant use with any MS DMT) rather than actual DDIs for each SIP.

Conclusion

The data were consistent across different databases and suggest ponesimod is expected to have the fewest clinical management events among S1Ps and may be easier to use overall than other S1Ps Example 4: Approved Drug Product Label Highlights of Prescribing Information These highlights do not include all the information needed to use PONVORY safely and effectively. See full prescribing information for PONVORY.

PONVORY™ (ponesimod) tablets, for oral use
Initial U.S. Approval: 2021

Indications and Usage

PONVORY is a sphingosine 1-phosphate receptor modulator indicated for the treatment of relapsing forms of multiple sclerosis (MS), to include clinically isolated syndrome, relapsing-remitting disease, and active secondary progressive disease, in adults. (1

Dosage and Administration

Assessments are required prior to initiating PONVORY (2.1)
Titration is required for treatment initiation (2.2)
The recommended maintenance dosage is 20 mg taken orally once daily (2.2)
First-dose monitoring is recommended for patients with sinus bradycardia, first- or second-degree [Mobitz type I]

atrioventricular (AV) block, or a history of myocardial infarction or bean figure (2.3)

Dosage Forms and Strengths

Tablets: 2 mg, 3 mg, 4 mg, 5 mg, 6 mg, 7 mg, 8 mg, 9 mg, 10 mg, and 20 mg (3)

Contraindications

In the last 6 months. experienced myocardial infarction, unstable angina, stroke transient ischemic attack (TIA), decompensated heart failure requiring hospitalization, or Class III/IV heart failure (4)

Presence of Mobitz type II second-degree, third-degree AV block, or sick sinus syndrome, unless patient has a functioning pacemaker (4)

Warnings and Precautions

Infections: PONVORY may increase the risk of infections. Obtain a complete blood count (CBC) before initiating treatment. Monitor for infection during treatment and for 1-2 weeks after discontinuation. Do not start PONVORY in patients with active infection. (5.1)

Bradvarrhythmia and Atrioventricular Condition Delays: PONVORY may result in a transient decrease in heart rate; titration is required for treatment initiation. Check an electrocardiogram (ECG) to assess for preexisting cardiac condition abnormalities before starting PONVORY. Consider cardiology consultation for conduction abnormalities or concomitant use with other drugs that decrease heart rate. (5.2, 7.2, 7.3)

Respiratory Effects: May cause a decline in pulmonary function. Assess pulmonary function (e.g., spirometry) if clinically indicated. (5.3)

Liver Injury: Discontinue if significant liver injury is confirmed. Obtain liver function tests before initiating PONVORY. (5.4)

Increased Blood Pressure (BP): Monitor BP during treatment. (5.5)

Cutaneous Malignancies: Periodic skin examination is recommended. (5.6)

Fetal Risk: Women of childbearing potential should use effective contraception during and for 1 week after stopping PONVORY. (5.7)

Macular Edema: An ophthalmic evaluation is recommended before starting treatment and if there is any change in vision while taking PONVORY. Diabetes mellitus and uveitis increase the risk. (5.8)

Adverse Reactions

Most common adverse reactions (incidence at least 10%) are upper respiratory tract infection, hepatic transaminase elevation and hypertension. (6.1).

To report SUSPECTED ADVERSE REACTIONS, contact Janssen Pharmaceuticals, Inc. at 1400-JANSSEN (1400426-7736) FDA at 1400-FDA-1088 or www.fda.gov/medwatch.

Drug Interactions

Vaccines: Avoid live attenuated vaccines during and for up to 1-2 weeks after treatment with PONVORY (7.4)

Strong CYP3A4 and UGT1A1 Inducers: Coadministration with PONVORY is not recommended (7.5)

Use in Specific Populations

Hepatic Impairment: PONVORY is not recommended in patients with moderate or severe hepatic impairment (Child-Pugh class B and C). (8.6)

See 17 for PATIENT COUNSELING INFORMATION and Medication Guide.

FULL PRESCRIBING INFORMATION: CONTENTS*
1 INDICATIONS AND USAGE
2 DOSAGE AND ADMINISTRATION
2.1 Assessments Prior to First Dose of PONVORY
2.2 Recommended Dosage
2.3 First Dose Monitoring in Patients with Certain Preexisting Cardiac Conditions
2.4 Reinitiation of PONVORY After Treatment Interruption
3 DOSAGE FORMS AND STRENGTHS
4 CONTRAINDICATIONS
5 WARNINGS AND PRECAUTIONS
5.1 Infections
5.2 Bradyarrhythmia and Atrioventricular Conduction Delays
5.3 Respiratory Effects
5.4 Liver Injury
5.5 Increased Blood Pressure
5.8 Cutaneous Malignancies
5.7 Fetal Risk
5.8 Macular Edema
5.9 Posterior Reversible Encephalopathy Syndrome
5.10 Unintended Additive Immunosuppressive Effects From Prior Treatment With Immunosuppressive or Immune-Modulating Therapies
5.11 Severe Increase in Disability After Stopping PONVORY
5.12 Immune System Effects After Stopping PONVORY
6 ADVERSE REACTIONS
6.1 Clinical Trials Experience
7 DRUG INTERACTIONS
7.1 Anti-Neoplastic, Immune-Modulating, or Immunosuppressive Therapies
7.2 Anti-Arrhythmic Drugs, QT Prolonging Drugs, Drugs that may Decrease Heart Rate
7.3 Beta-Blockers
7.4 Vaccination
7.5 Strong CYP3A4 and UGT1A1 Inducers
8 USE IN SPECIFIC POPULATIONS
8.1 Pregnancy
82 Lactation
8.3 Females and Males of Reproductive Potential
8.4 Pediatric Use
8.5 Geriatric Use
8.6 Hepatic Impairment
10 OVERDOSAGE
11 DESCRIPTION
12 CLINICAL PHARMACOLOGY
12.1 Mechanism of Action
12.2 Pharmacodynamics
12.3 Pharmacokinetics
13 NONCLINICAL TOXICOLOGY
13.1 Carcinogenesis, Mutagenesis, Impairment of Fertility
13.2 Animal Toxicology and/or Pharmacology
14 CLINICAL STUDIES 16 HOW SUPPLIED/STORAGE AND HANDLING
16.1 How Supplied
16.2 Storage and Handing
17 PATIENT COUNSELING INFORMATION
Sections or subsections omitted from full prescribing information are not listed.
Full Prescribing Information
1. Indications and Usage
PONVORY is indicated for the treatment of relapsing forms of multiple sclerosis (MS), to include clinically isolated syndrome, relapsing-remitting disease, and active secondary progressive disease, in adults.
2. Dosage and Administration
2.1 Assessments Prior to First Dose of PONVORY
Before initiation of treatment with PONVORY, assess the following:
Complete Blood Count
Obtain a recent (i.e., within the last 6 months or after discontinuation of prior MS therapy) complete blood count (CBC), including lymphocyte count [see Warnings and Precautions (5.1)].
Cardiac Evaluation
Obtain an electrocardiogram (ECG) to determine whether preexisting conduction abnormalities are present. In patients with certain preexisting conditions, advice from a cardiologist should be sought and first-dose monitoring is recommended [see Dosage and Administration (2.3) and Warnings and Precautions (5.2)].
Determine whether patients are taking drugs that could slow heart rate or atrioventricular (AV) conduction [see Warnings and Precautions (5.2)] and Drug Interactions (7.2, 7.3)].
Liver Function Tests
Obtain recent (i.e., within the last 6 months) transaminase and bilirubin levels [see Warnings and Precautions [(5.4)].
Ophthalmic Evaluation
Obtain an evaluation of the fundus, including the macula [see Warnings and Precautions (5.8)].
Current or Prior Medications with Immune System Effects
If patients are taking anti-neoplastic, immunosuppressive, or immune-modulating therapies, or if there is a history of prior use of these drugs, consider possible unintended additive immunosuppressive effects before initiating treatment with PONVORY [see Warnings and Precautions (5.1, 5.10) and Drug Interactions (7.1)].
Vaccinations
Test patients for antibodies to varicella zoster virus (VZV) before initiating PONVORY; VZV vaccination of antibody-negative patients is recommended prior to commencing treatment with PONVORY [see Warnings and Precautions (5.1)]. If live attenuated vaccine immunizations are required, administer at least 1 month prior to initiation of PONVORY.
2.2. Recommended Dosage
Maintenance Dosage
After dose titration is complete (see Treatment Initiation), the recommended maintenance dosage of PONVORY is 20 mg taken orally once daily starting on Day 15. Administer PONVORY orally once daily. Swallow the tablet whole. PONVORY can be taken with or without food.
Treatment Initiation
A starter pack must be used for patients initiating treatment with PONVORY [see How Supplied/Storage and Handling (16.1)]. Initiate PONVORY treatment with a 14-day titration; start with one 2 mg tablet orally once daily and progress with the titration schedule as shown in Table 19 [see Warnings and Precautions (5.2)].

TABLE 19

Dose Titration Regimen

| Titration Day | Daily Dose |
|---|---|
| Days 1 and 2 | 2 mg |
| Days 3 and 4 | 3 mg |
| Days 5 and 6 | 4 mg |
| Day 7 | 5 mg |
| Day 8 | 6 mg |
| Day 9 | 7 mg |
| Day 10 | 8 mg |
| Day 11 | 9 mg |
| Days 12, 13, and 14 | 10 mg |
| Maintenance | |
| Day 15 and thereafter | 20 mg |

If dose titration is interrupted, missed dose instructions must be followed [see Dosage and Administration (2.4)].
2.3 First Dose Monitoring in Patients with Certain Preexisting Cardiac Conditions
Because initiation of PONVORY treatment results in a decrease in heart rate (HR), first-dose 4-hour monitoring is recommended for patients with sinus bradycardia [HR less than 55 beats per minute (bpm)], first- or second-degree [Mobitz type I] AV block, or a history of myocardial infarction or heart failure occurring more than 6 months prior to treatment initiation and in stable condition [see Warnings and Precautions (5.3) and Clinical Pharmacology (12.2)].
First Dose 4-Hour Monitoring
Administer the first dose of PONVORY in a setting where resources to appropriately manage symptomatic bradycardia are available. Monitor patients for 4 hours after the first dose for signs and symptoms of bradycardia with a minimum of hourly pulse and blood pressure measurements. Obtain an ECG in these patients prior to dosing and at the end of the 4-hour observation period.
Additional Monitoring After 4-Hour Monitoring
If any of the following abnormalities are present after 4 hours (even in the absence of symptoms). continue monitoring until the abnormality resolves: The heart rate 4 hours post-dose is less than 45 bpm
The heart rate 4 hours post-dose is at the lowest value post-dose, suggesting that the maximum pharmacodynamic effect on the heart may not have occurred
The ECG 4 hours post-dose shows new onset second-degree or higher AV block.
If post-dose symptomatic bradycardia, bradyarrhythmia, or conduction related symptoms occur, or if ECG 4 hours post-dose shows new onset second degree or higher AV block or QTc greater than or equal to 500 msec, initiate appropriate management, begin continuous ECG monitoring, and continue monitoring until the symptoms have resolved if no pharmacological treatment is required. If pharmacological treatment is required, continue monitoring overnight and repeat 4-hour monitoring after the second dose.
Advice from a cardiologist should be sought to determine the most appropriate monitoring strategy (which may include overnight monitoring) during treatment initiation, if treatment with PONVORY is considered in patients: With some preexisting heart and cerebrovascular conditions [see Warnings and Precautions (5.2)]
With a prolonged QTc interval before dosing or during the 4-hour observation, or at additional risk for QT prolongation, or on concurrent therapy with QT prolonging drugs with a known risk of torsades de pointes [see Warnings and Precautions (5.2) and Drug Interactions (7.2)]

Receiving concurrent therapy with drugs that slow heart rate or AV conduction [see Drug Interactions (7.2, 7.3)].

2.4 Reinitiation of PONVORY after Treatment Interruption

Interruption during treatment, especially during titration, is not recommended; however:

If fewer than 4 consecutive doses are missed:
  during titration: resume treatment with the first missed titration dose and resume the titration schedule at that dose and titration day.
  during maintenance: resume treatment with the maintenance dosage.

If 4 or more consecutive doses are missed during titration or maintenance:
  treatment should be reinitiated with Day 1 of the titration regimen (new starter pack).

If treatment needs to be reinitiated with Day 1 of the titration regimen (new starter pack), complete first-dose monitoring in patients for whom it is recommended [see Dosage and Administration (2.3)].

3. Dosage Forms and Strengths

PONVORY is available as round, biconvex, film-coated tablets for oral use. PONVORY contains ponesimod in the following dosage strengths (see Table 20).

TABLE 20

Dosage Form and Strengths for PONVORY

| Tablet Strength | Tablet Color | Tablet Size | Tablet Debossing |
|---|---|---|---|
| 2 mg | White | 5.0 mm | "2" on one side and an arch on the other side. |
| 3 mg | Red | 5.0 mm | "3" on one side and an arch on the other side. |
| 4 mg | Purple | 5.0 mm | "4" on one side and an arch on the other side. |
| 5 mg | Green | 8.6 mm | "5" on one side and an arch and an "A" on the other side. |
| 6 mg | White | 8.6 mm | "6" on one side and an arch and an "A" on the other side. |
| 7 mg | Red | 8.6 mm | "7" on one side and an arch and an "A" on the other side. |
| 8 mg | Purple | 8.6 mm | "8" on one side and an arch and an "A" on the other side. |
| 9 mg | Brown | 8.6 mm | "9" on one side and an arch and an "A" on the other side. |
| 10 mg | Orange | 8.6 mm | "10" on one side and an arch and an "A" on the other side. |
| 20 mg | Yellow | 8.6 mm | "20" on one side and an arch and an "A" on the other side. |

4. Contraindications

PONVORY is contraindicated in patients who:

In the last 6 months, have experienced myocardial infarction, unstable angina, stroke, transient ischemic attack (TLA), decompensated heart failure requiring hospitalization, or Class III or IV heart failure [see Warnings and Precautions (5.2)]

Have presence of Mobitz type II second-degree. third-degree atrioventricular (AV) block, or sick sinus syndrome, or sino-atrial block, unless patient has a functioning pacemaker [see Warnings and Precautions (5.2)].

5. Warnings and Precautions 5.1 Infections

Risk of Infections

PONVORY causes a dose-dependent reduction in peripheral lymphocyte count to 30-40% of baseline values because of reversible sequestration of lymphocytes in lymphoid tissues [see Clinical Pharmacology (12.2)]. PONVORY may therefore increase the susceptibility to infections. Life-threatening and rare fatal infections have been reported in association with other sphingosine 1-phosphate (SIP) receptor modulators.

In Study 1 [see Clinical Studies (14)], the overall rate of infections was comparable between the PONVORY-treated patients and those receiving teriflunomide 14 mg (54.2% vs 52.1%, respectively). PONVORY increased the risk of upper respiratory tract infections. Serious or severe infections occurred in 1.6% of PONVORY-treated patients compared to 0.9% of patients receiving teriflunomide 14 mg.

Before initiating treatment with PONVORY, results from a recent (i.e., within 6 months or after discontinuation of prior therapy) complete blood count including lymphocyte count should be reviewed.

Initiation of treatment with PONVORY should be delayed in patients with active infection until resolution. Lymphocyte counts returned to the normal range in 90% of patients within 1 week of stopping therapy in modeling studies [see Clinical Pharmacology (12.2)]. In Study 1, peripheral lymphocyte counts returned to normal range within 2 weeks after discontinuation of PONVORY, which was the first timepoint evaluated. Because residual pharmacodynamic effects, such as lowering effects on peripheral lymphocyte count, may persist for 1 to 2 weeks after discontinuation of PONVORY, vigilance for infection should be continued for 1 to 2 weeks after PONVORY is discontinued [see Warnings and Precautions (5.12)].

In Study 1, the proportion of patients who experienced lymphocyte counts less than $0.2 \times 10^9$/L was 3.2%. Effective diagnostic and therapeutic strategies should be employed in patients with symptoms of infection while on therapy. Consider interruption of treatment with PONVORY if a patient develops a serious infection.

Herpes Viral Infections

Cases of herpes viral infection have been reported in the development program of PONVORY; herpes simplex encephalitis and varicella zoster meningitis have been reported with other S1P receptor modulators.

In Study 1, the rate of heipetic infections was 4.8% for both PONVORY-treated patients and those receiving teriflunomide 14 mg. Patients without a healthcare professional confirmed history of varicella (chickenpox) or without documentation of a full course of vaccination against VZV should be tested for antibodies to VZV before initiating PONVORY (see Vaccinations).

Cryptococcal Infections

Cases of fatal cryptococcal meningitis (CM) and disseminated cryptococcal infections have been reported with other S1P receptor modulators. Physicians should be vigilant for clinical symptoms or signs of CM. Patients with symptoms or signs consistent with a cryptococcal infection should undergo prompt diagnostic evaluation and treatment. PONVORY treatment should be suspended until a cryptococcal infection has been excluded. If CM is diagnosed, appropriate treatment should be initiated.

Progressive Multifocal Leukoencephalopathy

Progressive multifocal leukoencephalopathy (PML) is an opportunistic viral infection of the brain caused by the JC virus (JCV) that typically only occurs in patients who are immunocompromised, and that usually leads to death or severe disability. Typical symptoms associated with PML are diverse, progress over days to weeks. and include progressive weakness on one side of the body or clumsiness of limbs, disturbance of vision, and changes in thinking, memory, and orientation leading to confusion and personality changes.

PML has been reported in patients treated with a S1P receptor modulator and other multiple sclerosis (MS) therapies and has been associated with some risk factors (e.g., immunocompromised patients, polytherapy with immunosuppressants). Physicians should be vigilant for clinical symptoms or magnetic resonance imaging (MRI) findings that may be suggestive of PML. MRI findings may be apparent before clinical signs or symptoms. If PML is suspected, treatment with PONVORY should be suspended until PML has been excluded. If PML is confirmed, treatment with PONVORY should be discontinued.

Prior and Concomitant Treatment with Anti-Neoplastic, Immune-Modulating, or Immunosuppressive Therapies Anti-neoplastic, immune-modulating, or immunosuppressive therapies (including corticosteroids) should be coadministered with caution because of the risk of additive immune system effects [see Drug Interactions (7.1)].

Vaccinations

Patients without a healthcare professional confirmed history of chickenpox or without documentation of a full course of vaccination against VZV should be tested for antibodies to VZV before initiating PONVORY treatment. A full course of vaccination for antibody-negative patients with varicella vaccine is recommended prior to commencing treatment with POVORY, following which initiation of treatment with PONVORY should be postponed for 4 weeks to allow the full effect of vaccination to occur.

No clinical data are available on the efficacy and safety of vaccinations in patients taking PONVORY. Vaccinations may be less effective if administered during PONVORY treatment.

If live attenuated vaccine immunizations are required, administer at least 1 month prior to initiation of PONVORY. Avoid the use of live attenuated vaccines during and for 1 to 2 weeks after treatment with PONVORY.

5.2 Bradyarrhythmia and Atrioventricular Conduction Delays

Since initiation of PONVORY treatment results in a transient decrease in heart rate and atrioventricular (AV) conduction delays, an up-titration scheme must be used to reach the maintenance dosage of PONVORY (20 mg) [see Dosage and Administration (2.2) and Clinical Pharmacology (12.2)].

Study 1 did not include patients who had:

A resting heart rate (HR) less than 50 beats per minute (bpm) on baseline electrocardiogram Myocardial infarction or unstable ischemic heart disease in the last 6 months Cardiac failure (New York Heart Association class III-IV) or presence of any severe cardiac disease Cardiac conduction or rhythm disorders (including sinoatrial heart block, symptomatic bradycardia, atrial flutter or atrial fibrillation, ventricular arrhythmia, cardiac arrest) either in history or observed at screening Mobitz Type II second degree AV block or higher-grade AV block observed at screening QTcF interval greater than 470 ms (females) and greater than 450 ms (males) observed at screening History of syncope associated with cardiac disorders Uncontrolled systemic arterial hypertension Reduction in Heart Rate.

Reduction in Heart Rate

Initiation of PONVORY may result in a transient decrease in HR. In Study 1, bradycardia at treatment initiation and sinus bradycardia on ECG (defined as HR less than 50 bpm) occurred in 5.8% of PONVORY-treated patients compared to 1.6% of patients receiving teriflunomide 14 mg. After the first titration dose of PONVORY, the decrease in heart rate typically begins within an hour and reaches its nadir within 2-4 hours. The heart rate typically recovers to baseline levels 4-5 hours after administration. The mean decrease in heart rate on Day 1 of dosing was 6 bpm. With up-titration after Day 1, the post-dose decrease in heart rate is less pronounced. Bradycardia resolved in all patients in Study 1 without intervention and did not require discontinuation of PONVORY treatment. On Day 1, 3 patients treated with PONVORY had asymptomatic post-dose HR below or equal to 40 bpm; all 3 patients had baseline HRs below 55 bpm.

Atrioventricular Conduction Delays

Initiation of PONVORY treatment has been associated with transient atrioventricular conduction delays that follow a similar temporal pattern as the observed decrease in heart rate during dose titration. In Study 1, the AV conduction delays manifested as first-degree AV block (prolonged PR interval on ECG). which occurred in 3.4% of PONVORY-treated patients and in 1.2% of patients receiving teriflunomide 14 mg. The conduction abnormalities typically were transient, asymptomatic, resolved within 24 hours, resolved without intervention, and did not require discontinuation of PONVORY treatment. In Study 1, second- and third-degree AV blocks were not reported in patients treated with PONVORY.

If treatment with PONVORY is considered, advice from a cardiologist should be sought for individuals:

With significant QT prolongation (QTc greater than 500 msec)

With atrial flutter fibrillation or arrhythmia treated with Class Ia or Class III anti-arrhythmic drugs [see Drug Interactions (7.2)]

With unstable ischemic heart disease, cardiac decompensated failure occurring more than 6 months prior to treatment initiation history of cardiac arrest, cerebrovascular disease (TIA, stroke occurring more than 6 months prior to treatment initiation), or uncontrolled hypertension With a history of Mobitz Type II second degree AV block or higher-grade AV block, sick-sinus syndrome, or sinoatrial heart block [see Contraindications (4)].

Treatment Initiation Recommendations

Obtain an ECG in all patients to determine whether preexisting conduction abnormalities are present.

In all patients, a dose titration is recommended for initiation of PONVORY treatment to help reduce cardiac effects [see Dosage and Administration (2.2)].

In patients with sinus bradycardia, first—or second—degree [Mobitz type I] AV block, or a history of myocardial infarction or heart failure with onset more than 6 months prior to initiation first-dose monitoring is recommended [see Dosage and Administration (2.1, 2.3)].

PONVORY is not recommended in patients with a history of cardiac arrest, cerebrovascular disease (e.g., TIA, stroke occurring more than 6 months prior to treatment initiation), uncontrolled hypertension, or severe untreated sleep apnea, since significant bradycardia may be poorly tolerated in these patients. If treatment is considered, advice from a cardiologist should be sought prior to initiation of treatment in order to determine the most appropriate monitoring strategy.

Use of PONVORY in patients with a history of recurrent syncope or symptomatic bradycardia should be based on an overall benefit-risk assessment. If treatment is considered, advice from a cardiologist should be sought prior to initiation of treatment in order to determine the most appropriate monitoring.

Experience with PONVORY is limited in patients receiving concurrent therapy with drugs that decrease heart rate (e.g., beta-blockers, non-dihydropyridine calcium channel blockers—diltiazem and verapamil, and other drugs that may decrease heart rate such as digoxin). Concomitant use of these drugs during PONVORY initiation may be associated with severe bradycardia and heart block. If treatment is considered, advice from a cardiologist should be sought prior to initiation of treatment in order to determine the most appropriate monitoring.

For patients receiving a stable dose of a beta-blocker, the resting heart rate should be considered before introducing PONVORY treatment. If the resting heart rate is greater than 55 bpm under chronic beta-blocker treatment, PONVORY can be introduced. If resting heart rate is less than or equal to 55 bpm, beta-blocker treatment should be interrupted until the baseline heart rate is greater than 55 bpm. Treatment with PONVORY can then be initiated and treatment with a beta-blocker can be reinitiated after PONVORY has been up-titrated to the target maintenance dosage [see Drug Interactions (7.3)].

For patients taking other drugs that decrease heart rate, treatment with PONVORY should generally not be initiated without consultation from a cardiologist because of the potential additive effect on heart rate [see Dosage and Administration (2.3) and Drug Interactions (7.2)].

Missed Dose During Treatment Initiation or Maintenance Treatment

If 4 or more consecutive daily doses are missed during treatment initiation or maintenance treatment, reinitiate Day 1 of the dose titration (new starter pack) and follow first-dose monitoring recommendations [see Dosage and Administration (2.4)].

5.3 Respiratory Effects

Dose-dependent reductions in forced expiratory volume over 1 second ($FEV_1$) and reductions in diffusion lung capacity for carbon monoxide ($DL_{CO}$) were observed in PONVORY-treated patients mostly occurring in the first month after treatment initiation. In Study 1, the reduction from baseline in percent predicted $FEV_1$ at 2 years was 8.3% in PONVORY-treated patients compared to 4.4% in patients receiving teriflunomide 14 mg. In Study 1, 7 patients discontinued PONVORY because of pulmonary adverse events. There is insufficient information to determine the reversibility of the decrease in $FEV_1$ or FVC after treatment discontinuation. PONVORY should be used with caution in patients with severe respiratory disease (i.e., pulmonary fibrosis, asthma, and chronic obstructive pulmonary disease). Spirometric evaluation of respiratory function should be performed during therapy with PONVORY if clinically indicated.

5.4 Liver Injury

Elevations of transaminases may occur in PONVORY-treated patients.

Obtain transaminase and bilirubin levels, if not recently available (i.e., within last 6 months) before initiation of PONVORY.

In Study 1, elevations of ALT to 5-fold the upper limit of normal (ULN) or greater occurred in 4.6% of patients treated with PONVORY compared to 2.5% of patients who received teriflunomide 14 mg. Elevation of ALT to 3-fold the ULN or greater occurred in 17.3% of patients treated with PONVORY and 8.3% of patients treated with teriflunomide 14 mg. The median time to an elevation of 3-fold the ULN was 3 months. The majority (89%) of patients with ALT increases 3-fold or greater the ULN continued treatment with PONVORY with values returning to less than three times the ULN within approximately 2-4 weeks.

In Study 1, the discontinuation rate because of elevations in hepatic enzymes was 2.3% of patients treated with PONVORY and 1.9% of patients who received teriflunomide 14 mg.

Patients who develop symptoms suggestive of hepatic dysfunction, such as unexplained nausea, vomiting, abdominal pain, fatigue, anorexia, rash with eosinophilia, or jaundice and/or dark urine during treatment, should have hepatic enzymes checked. PONVORY should be discontinued if significant liver injury is confirmed.

No dosage adjustment is necessary in patients with mild hepatic impairment (Child-Pugh class A). PONVORY is not recommended in patients with moderate or severe hepatic impairment (Child-Pugh class B and C, respectively) [see Use in Specific Populations (8.6) and Clinical Pharmacology (12.3)].

5.5 Increased Blood Pressure

In Study 1, PONVORY-treated patients had an average increase of 2.9 mm Hg in systolic blood pressure and 2.8 mm Hg in diastolic blood pressure compared to 2.8 mm Hg and 3.1 mm Hg in patients receiving teriflunomide 14 mg, respectively. An increase in blood pressure with PONVORY was first detected after approximately 1 month of treatment initiation and persisted with continued treatment. Hypertensive events were reported as an adverse reaction in 10.1% of PONVORY-treated patients and in 9.0% of patients receiving teriflunomide 14 mg. One patient treated with PONVORY experienced a hypertensive crisis but had evidence of longstanding hypertensive heart disease. Blood pressure should be monitored during treatment with PONVORY and managed appropriately.

5.6 Cutaneous Malignancies

Cases of basal cell carcinoma and other skin malignancies have been reported in patients treated with S1P receptor modulators, including PONVORY. In Study 1, the incidence of basal cell carcinoma was 0.4% in PONVORY-treated patients compared to 0.2% in patients receiving teriflunomide 14 mg. Cases of other cutaneous malignancies, including melanoma and squamous cell carcinoma, have also been reported in patients treated with PONVORY and in patients treated with other S1P modulators.

Periodic skin examination is recommended for all patients, particularly those with risk factors for skin cancer. Providers and patients are advised to monitor for suspicious skin lesions. If a suspicious skin lesion is observed, it should be promptly evaluated. As usual for patients with increased risk for skin cancer, exposure to sunlight and ultraviolet light should be limited by wearing protective clothing and using a sunscreen with a high protection factor. Concomitant phototherapy with UV-B radiation or PUVA-photochemotherapy is not recommended in patients taking PONVORY.

5.7 Fetal Risk

Based on animal studies, PONVORY may cause fetal harm [see Use in Specific Populations 8.1, 8.3)]. Because it takes approximately 1 week to eliminate PONVORY from the body, women of childbearing potential should use effective contraception to avoid pregnancy during and for 1 week after stopping PONVORY treatment.

5.8 Macular Edema

S1P receptor modulators, including PONVORY, have been associated with an increased risk of macular edema. In Study 1, macular edema was reported in 1.1% of PONVORY-treated patients compared to none of the patients receiving teriflunomide 14 mg.

An ophthalmic evaluation of the fundus, including the macula, is recommended in all patients before starting treatment and again at any time if a patient reports any change in vision while on PONVORY therapy.

Continuation of PONVORY therapy in patients with macular edema has not been evaluated. A decision on whether PONVORY should be discontinued should take into account the potential benefits and risks for the individual patient.

Macular Edema in Patients with a History of Uveitis or Diabetes Mellitus

Patients with a history of uveitis and patients with diabetes mellitus are at increased risk of macular edema during therapy with S1P receptor modulators, including PONVORY. Therefore, these patients should have regular follow-up examinations of the fundus, including the macula, during treatment with PONVORY.

5.9 Posterior Reversible Encephalopathy Syndrome

Rare cases of posterior reversible encephalopathy syndrome (PRES) have been reported in patients receiving a sphingosine 1-phosphate (S1P) receptor modulator. Such events have not been reported for PONVORY-treated patients in the development program. However, should a PONVORY-treated patient develop any unexpected neurological or psychiatric symptoms/signs (e.g., cognitive deficits, behavioral changes, cortical visual disturbances, or any other neurological cortical symptoms/signs), any symptom/sign suggestive of an increase of intracranial pressure, or accelerated neurological deterioration, the physician should promptly schedule a complete physical and neurological examination and should consider an MRI. Symptoms of PRES are usually reversible but may evolve into ischemic stroke or cerebral hemorrhage. Delay in diagnosis and treatment may lead to permanent neurological sequelae. If PRES is suspected, PONVORY should be discontinued.

5.10 Unintended Additive Immunosuppressive Effects from Prior Treatment with Immunosuppressive or Immune-Modulating Therapies When switching from drugs with prolonged immune effects, the half-life and mode of action of these drugs must be considered in order to avoid unintended additive effects on the immune system while at the same time minimizing risk of disease reactivation, when initiating PONVORY.

Initiating treatment with PONVORY after treatment with alemtuzumab is not recommended.

5.11 Severe Increase in Disability after Stopping PONVORY

Severe exacerbation of disease, including disease rebound. has been rarely reported after discontinuation of a S1P receptor modulator. The possibility of severe exacerbation of disease should be considered after stopping PONVORY treatment. Patients should be observed for a severe increase in disability upon PONVORY discontinuation and appropriate treatment should be instituted, as required.

5.12 Immune System Effects After Stopping PONVORY

After stopping PONVORY therapy, ponesimod remains in the blood for up to 1 week. Starting other therapies during this interval will result in concomitant exposure to ponesimod. Lymphocyte counts returned to the normal range in 90% of patients within 1 week of stopping PONVORY therapy in modeling studies [see Clinical Pharmacology (12.2)]. However, residual pharmacodynamics effects, such as lowering effects on peripheral lymphocyte count, may persist for 1 to 2 weeks after the last dose. Use of immunesuppressants within this period may lead to an additive effect on the immune system, and therefore caution should be applied 1 to 2 weeks after the last dose of PONVORY [see Drug Interactions (7.1)].

6. Adverse Reactions

The following serious adverse reactions are described elsewhere in labeling: Infections [see Warnings and Precautions (5.1)]

Bradyarrhythmia and Atrioventricular Conduction Delays [see Warnings and Precautions (5.2)]

Respiratory Effects [see Warnings and Precautions (5.3)]
Liver Injury [see Warnings and Precautions (5.4)]
Increased Blood Pressure [see Warnings and Precautions (5.5)]
Cutaneous Malignancies [see Warnings and Precautions (5.6)]
Fetal Risk [see Warnings and Precautions (5.7)]
Macular Edema [see Warnings and Precautions (5.8)]
Posterior Reversible Encephalopathy Syndrome [see Warnings and Precautions (5.9)]
Unintended Additive Immunosuppressive Effects From Prior Treatment With Immunosuppressive or Immune-Modulating Therapies [see Warnings and Precautions (5.10)]
Severe Increase in Disability After Stopping PONVORY [see Warnings and Precautions (5.11)]
Immune System Effects After Stopping PONVORY [see Warnings and Precautions (5.12)].

6.1 Clinical Trials Experience

Because clinical trials are conducted under widely varying conditions, adverse reaction rates observed in the clinical trials of a drug cannot be directly compared to rates in the clinical trials of another drug and may not reflect the rates observed in practice.

A total of 1438 MS patients have received PONVORY at doses of at least 2 mg daily. These patients were included in Study 1 (2-year active-controlled versus teriflunomide 14 mg) [see Clinical Studies (14)] and in a Phase 2 (6-month placebo-controlled) study in patients with MS and the uncontrolled extension studies.

In Study 1, 82% of PONVORY-treated patients completed 2 years of study treatment, compared to 82.2% of patients receiving teriflunomide 14 mg. Adverse events led to discontinuation of treatment in 8.7% of PONVORY-treated patients. compared to 6% of patients receiving teriflunomide 14 mg. The most common adverse reactions (incidence at least 10%) in PONVORY-treated patients in Study 1 were upper respiratory tract infection, hepatic transaminase elevation, and hypertension. Table 21 lists adverse reactions that occurred in at least 2% of PONVORY-treated patients and at a higher rate than in patients receiving teriflunomide 14 mg.

TABLE 21

Adverse Reactions Reported in Study 1 Occurring in at Least 2% of PONVORY-Treated Patients and at a Higher Rate Than in Patients Receiving Teriflunomide 14 mg

| Adverse Reaction | PONVORY N = 565 (%) | Teriflunomide 14 mg N = 566 (%) |
|---|---|---|
| Upper respiratory infection [a] | 37 | 34 |
| Hepatic transaminase elevation [b] | 23 | 12 |
| Hypertension [c] | 10 | 9 |

TABLE 21-continued

Adverse Reactions Reported in Study 1 Occurring in at Least 2% of PONVORY-Treated Patients and at a Higher Rate Than in Patients Receiving Teriflunomide 14 mg

| Adverse Reaction | PONVORY<br>N = 565<br>(%) | Teriflunomide<br>14 mg<br>N = 566<br>(%) |
|---|---|---|
| Urinary tract infection | 6 | 5 |
| Dyspnea | 5 | 1 |
| Dizziness | 5 | 3 |
| Cough | 4 | 2 |
| Pain in extremity | 4 | 3 |
| Somnolence | 3 | 2 |
| Pyrexia | 2 | 1 |
| C-reactive protein increased | 2 | 1 |
| Hypercholesterolemia | 2 | 1 |
| Vertigo | 2 | 1 |

[a] Includes the following terms: nasopharyngitis, upper respiratory tract infection, pharyngitis, respiratory tract infection, bronchitis, respiratory tract infection viral, viral upper respiratory tract infection, tracheitis, and laryngitis.
[b] Includes the following terms: alanine aminotransferase increased, aspartate aminotransferase increased, hepatic enzyme increased, and transaminases increased
[c] Includes the following terms: hypertension, hypertensive crisis, blood pressure increased, blood pressure systolic increased, and blood pressure diastolic increased.

In Study 1, the following adverse reactions occurred in less than 2% of PONVORY-treated patients, but at a rate at least 1% higher than in patients receiving teriflunomide 14 mg: viral infection, herpes zoster, hyperkalemia, lymphopenia [see Warnings and Precautions (5.1), and macular edema [see Warnings and Precautions (5.8)].

Adverse reactions in patients treated with PONVORY in an additional 6-month placebo-controlled study were generally similar to those in Study 1. The following additional adverse reactions occurred in at least 2% of PONVORY 20 mg-treated patients and at a higher rate than in patients receiving placebo (but did not meet the reporting rate criteria for inclusion in Study 1): rhinitis, fatigue, chest discomfort, peripheral edema, joint swelling, blood cholesterol increased, migraine, insomnia, depression, dyspepsia, dry mouth, bradycardia, back pain, and sinusitis.

Additionally, in uncontrolled extension trials, the adverse reaction of pneumonia was reported.

Seizures

In Study 1, cases of seizures were reported in 1.4% of PONVORY-treated patients, compared to 0.2% in patients receiving teriflunomide 14 mg. It is not known whether these events were related to the effects of MS, to PONVORY, or to a combination of both.

Respiratory Effects

In Study 1, dose-dependent reductions in forced expiratory volume over 1 second ($FEV_1$) were observed in patients treated with PONVORY [see Warnings and Precautions (5.3)].

Malignancies

In Study 1, two cases of basal cell carcinoma (0.4%) were reported in PONVORY-treated patients, compared to one case of basal cell carcinoma (0.2%) in patients receiving teriflunomide 14 mg, and a case of malignant melanoma was reported in a PONVORY-treated patient. An increased risk of cutaneous malignancies has been reported in association with other S1P receptor modulators, including PONVORY [see Warnings and Precautions (5.6)].

7. Drug Interactions 7.1 Anti-Neoplastic, Immune-Modulating, or Immunosuppressive Therapies PONVORY has not been studied in combination with anti-neoplastic, immune-modulating, or immunosuppressive therapies. Caution should be used during concomitant administration because of the risk of additive immune effects during such therapy and in the weeks following administration [see Warnings and Precautions (5.1)].

When switching from drugs with prolonged immune effects, the half-life and mode of action of these drugs must be considered in order to avoid unintended additive effects on the immune system [see Warnings and Precautions (5.10)].

Because of the characteristics and duration of alemtuzumab immune suppressive effects, initiating treatment with PONVORY after alemtuzumab is not recommended.

PONVORY can generally be started immediately after discontinuation of beta interferon or glatiramer acetate.

7.2 Anti-Arrhythmic Drugs, QT Prolonging Drugs, Drugs that may Decrease Heart Rate PONVORY has not been studied in patients taking QT prolonging drugs.

Class Ia (e.g., quinidine, procainamide) and Class III (e.g., amiodarone, sotalol) anti-arrhythmic drugs have been associated with cases of Torsades de Pointes in patients with bradycardia. If treatment with PONVORY is considered, advice from a cardiologist should be sought.

Because of the potential additive effects on heart rate, treatment with PONVORY should generally not be initiated in patients who are concurrently treated with QT prolonging drugs with known arrhythmogenic properties, heart rate lowering calcium channel blockers (e.g., verapamil, diltiazem), or other drugs that may decrease heart rate (e.g., digoxin) [see Warnings and Precautions (5.2) and Drug Interactions (7.3)]. If treatment with PONVORY is considered, advice from a cardiologist should be sought.

7.3 Beta-Blockers

Caution should be applied when PONVORY is initiated in patients receiving treatment with a beta-blocker because of the additive effects on lowering heart rate; temporary interruption of the beta-blocker treatment may be needed prior to initiation of PONVORY [see Warnings and Precautions (5.2)]. Beta-blocker treatment can be initiated in patients receiving stable doses of PONVORY.

7.4 Vaccination

During, and for up to 1 to 2 weeks after discontinuation of, treatment with PONVORY, vaccinations may be less effective. The use of live attenuated vaccines may carry the risk of infection and should therefore be avoided during PONVORY treatment and for 1 to 2 weeks after discontinuation of treatment with PONVORY [see Warnings and Precautions (5.1)].

7.5 Strong CYP3A4 and UGT1A1 Inducers

In vitro assessments and limited clinical data indicated that concomitant use of strong CYP3A4 and UGT1A1 inducers (e.g., rifampin, phenytoin, carbamazepine) may decrease the systemic exposure of ponesimod. It is unclear whether this decrease in ponesimod systemic exposure would be considered of clinical relevance. Coadministration of PONVORY with strong CYP3A4 and UGT1A1 inducers is not recommended.

8. Use in Specific Populations 8.1 Pregnancy

Risk Summary

There are no adequate and well-controlled studies of PONVORY in pregnant women. In animal studies, administration of ponesimod during pregnancy produced adverse effects on development, including embryo lethality and fetal malformations, in the absence of maternal toxicity. In rats and rabbits, visceral and skeletal malformations occurred at clinically relevant maternal ponesimod exposures (see Data). The receptor affected by ponesimod (sphingosine-1-phosphate receptor 1) has been demonstrated to have an important role in embryogenesis, including vascular and neural development.

In the US general population, the estimated background risk of major birth defects and miscarriage in clinically recognized pregnancies is 2%-4% and 15%-20%, respectively. The background risk of major birth defects and miscarriage for the indicated population is unknown.

Data

Animal Data

When ponesimod (0, 1, 10, or 40 mg/kg/day) was orally administered to pregnant rats during the period of organogenesis, increased incidences of fetal malformations primarily involving the limbs (syndactyly and ectrodactyly) and cardiovascular system (including ventricular septal defects) were observed at all but the lowest dose tested. A high incidence of embryofetal death was observed at the highest dose tested. Maternal toxicity was not observed, indicating a selective effect on the fetus. Plasma exposure (AUC) at the no-effect dose (1 mg/kg/day) for adverse effects on embryofetal development in rats was lower than that in humans at the recommended human dose (RHD) of 20 mg/day.

When ponesimod (0, 0.25, 1, or 4 mg/kg/day) was orally administered to pregnant rabbits during the period of organogenesis, an increase in post-implantation loss and fetal variations (visceral and skeletal) were noted at the highest dose tested. No maternal toxicity was observed. Plasma exposure at the no-effect dose (1 mg/kg/day) for adverse effects on embryofetal development in rabbits was lower than that in humans at the RHD. In a dose-range finding study in pregnant rabbits. oral administration of ponesimod (0, 6, 20, or 60 mg/kg/day) during organogenesis, an increase in embryofetal death and fetal limb malformation (brachydactyly) were observed at the lowest dose tested; at the higher doses, there were no live fetuses.

When ponesimod (5, 10, or 20 mg/kg) was orally administered to female rats throughout pregnancy and lactation, the offspring exhibited decreased survival, reduced body weight gain, and reduced fertility and reproductive performance (increases in pre- and post-implantation loss) at the highest dose tested, neurobehavioral impairment (increased locomotor activity) at the mid and high doses, and delayed sexual maturation at all doses tested. A no-effect dose for adverse effects on pre- and postnatal development in rats was not identified. Plasma exposure (AUC) in dams at the lowest dose tested was less than that in humans at the RHD.

8.2 Lactation

Risk Summary

There are no data on the presence of PONVORY in human milk, the effects on the breastfed infant, or the effects of the drug on milk production. When ponesimod was orally administered to female rats during pregnancy and lactation, ponesimod was detected in the plasma of the offspring, suggesting excretion of ponesimod in milk.

The developmental and health benefits of breastfeeding should be considered along with the mother's clinical need for PONVORY and any potential adverse effects on the breastfed infant from PONVORY or from the underlying maternal condition.

8.3 Females and Males of Reproductive Potential

Contraception

Females

Before initiation of PONVORY treatment, women of childbearing potential should be counseled on the potential for a serious risk to the fetus and the need for effective contraception during treatment with PONVORY [see Use in Specific Populations (8.1)]. Since it takes approximately one week to eliminate ponesimod from the body after stopping treatment, the potential risk to the fetus may persist, and women should use effective contraception during this period [see Warnings and Precautions (5.7)].

8.4 Pediatric Use

Safety and effectiveness in pediatric patients have not been established.

Juvenile Animal Toxicity Data

Oral administration of ponesimod (0, 1, 10, 30, or 100 mg/kg/day) to young rats from postnatal day 28 to 91 resulted in lung histopathology (alveolar histiocytosis/edema) and decreased immune function (T-cell dependent antibody response) at the two highest doses tested. Decreased growth (body weight gain and/or long bone length) was observed at all but the low dose, and neurobehavioral impairment (increased locomotor activity) was observed at the highest dose tested. Decreased lymphocyte count and neurobehavioral impairment persisted at the end of a 4-week recovery period.

8.5 Geriatric Use

Clinical studies of PONVORY did not include patients 65 years of age and over to determine whether they respond differently from younger subjects. Use of PONVORY in elderly patients should be cautious, reflecting the greater frequency of decreased hepatic, renal, or cardiac function, and of concomitant disease or other drug therapy [see Clinical Pharmacology (12.3)].

8.6 Hepatic Impairment

No dosage adjustment is necessary in patients with mild hepatic impairment (Child-Pugh class A) [see Clinical Pharmacology (12.3)].

PONVORY is not recommended in patients with moderate or severe hepatic impairment (Child-Pugh class B and C, respectively), as the risk of adverse reactions may be greater [see Clinical Pharmacology (12.3)].

9. Overdosage

Symptoms and Signs

In patients with overdosage of PONVORY, especially upon initiation/re-initiation of treatment, it is important to observe for signs and symptoms of bradycardia as well as AV conduction blocks, which may include overnight monitoring. Regular measurements of pulse rate and blood pressure are required, and ECGs should be performed [see Warnings and Precautions (5.2, 5.5) and Clinical Pharmacology (12.2)].

Treatment

There is no specific antidote to ponesimod. Neither dialysis nor plasma exchange would result in meaningful removal of ponesimod from the body. The decrease in heart rate induced by PONVORY can be reversed by atropine.

In the event of overdose, PONVORY should be discontinued, and general supportive treatment given until clinical toxicity has been diminished or resolved. It is advisable to contact a poison control center to obtain the latest recommendations for the management of an overdose.

10. Description

PONVORY (ponesimod) is a sphingosine 1-phosphate receptor modulator.

The chemical name for ponesimod is (2Z,5Z)-5-[3-chloro-4-[(2R)-2,3-dihydroxypropoxy]benzylidene]-3-(2-methylphenyl)-2-(propylimino)-1,3-thiazolidin-4-one. It has one chiral center with absolute configuration of (R). Its molecular formula is $C_{23}H_{35}ClN_2O_4S$ and its molecular weight is 460.97 g/mol. Ponesimod has the following structural formula:

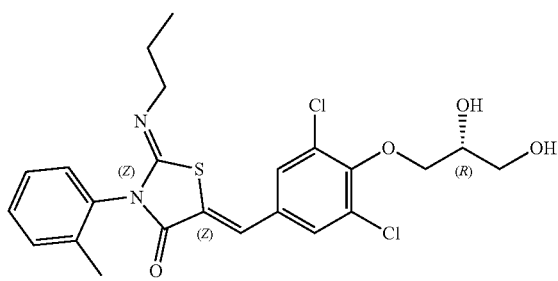

Ponesimod is a white to light yellowish powder that is practically insoluble or insoluble in water.

PONVORY (ponesimod) is provided as 2 mg, 3 mg, 4 mg, 5 mg, 6 mg, 7 mg, 8 mg, 9 mg, 10 mg, and 20 mg film-coated tablets for oral administration.

Each tablet contains the following inactive ingredients: croscarmellose sodium. lactose monohydrate, magnesium stearate, microcrystalline cellulose. povidone K30. silica colloidal anhydrous. and sodium lauryl sulfate.

Each tablet coating contains ferrosoferric oxide (included in 4 mg, 5 mg, 8 mg, and 9 mg film-coated tablets), hydroxypropyl methylcellulose 2910, iron oxide red (included in 3 mg, 4 mg, 7 mg, 8 mg, 9 mg, and 10 mg film-coated tablets), iron oxide yellow (included in 3 mg, 5 mg, 7 mg, 9 mg, 10 mg, and 20 mg film-coated tablets), lactose monohydrate, polyethylene glycol 3350, titanium dioxide, and triacetin.

11. Clinical Pharmacology
11.1 Mechanism of Action

Ponesimod is a sphingosine 1-phosphate (S1P) receptor 1 modulator that binds with high affinity to S1P receptor 1.

Ponesimod blocks the capacity of lymphocytes to egress from lymph nodes, reducing the number of lymphocytes in peripheral blood. The mechanism by which ponesimod exerts therapeutic effects in multiple sclerosis is unknown, but may involve reduction of lymphocyte migration into the central nervous system.

11.2 Pharmacodynamics
Immune System

In healthy volunteers, PONVORY induces a dose-dependent reduction of the peripheral blood lymphocyte count from a single dose of 5 mg onwards, with the greatest reduction observed 6 hours post-dose, caused by reversible sequestration of lymphocytes in lymphoid tissues. After 7 daily doses of 20 mg, the greatest decrease in absolute mean lymphocyte count was to 26% of baseline (650 cells/µL), observed 6 hours after administration. Peripheral blood B cells [CD19+] and T cells [CD3+], T-helper [CD3+CD4+], and T-cytotoxic [CD3+CD8+] cell subsets are all affected, while NK cells are not. T-helper cells were more sensitive to the effects of ponesimod than T-cytotoxic cells.

PK/PD modeling indicates lymphocyte counts returned to the normal range in greater than 90% of healthy subjects within 1 to 2 weeks of stopping therapy. In Study 1, peripheral lymphocyte counts returned to the normal range within 2 weeks after discontinuation of PONVORY.

Heart Rate and Rhythm

PONVORY causes a transient dose-dependent reduction in heart rate (HR) and AV conduction delays upon treatment initiation [see Warnings and Precautions (5.2)]. The heart rate decreases plateaued at doses greater than or equal to 40 mg [2 times the recommended maintenance dosage], and bradyarrhythmic events (AV blocks) were detected at a higher incidence under PONVORY treatment, compared to placebo. This effect starts within the first hour of dosing and is maximal at 2-4 hours post-dose. HR generally returns to pre-dose values by 4-5 hours post-dose on Day 1, and the effect diminishes with repeated administration. indicating tolerance.

The decrease in heart rate induced by ponesimod can be reversed by atropine.

Beta-Blockers

The negative chronotropic effect of coadministration of PONVORY and propranolol was evaluated in a dedicated pharmacodynamics safety study. The addition of PONVORY to propranolol at steady state has an additive effect on HR effect [see Drug Interactions (7.3)].

Cardiac Electrophysiology

In a thorough QT study, daily administration of ponesimod doses of 40 mg and 100 mg (respectively 2- and 5-fold the recommended maintenance dose) until steady-state conditions were achieved resulted in prolongation of Fridericia-corrected QT (QTcF) intervals, with the maximum mean (upper bound of 90% two-sided confidence interval) at 11.8 ms (40 mg) and 16.2 ms (100 mg). No subject had absolute QTcF greater than 480 ms or AQTcF greater than 90 ms for ponesimod treatment.

Pulmonary Function

Dose-dependent reductions in $FEV_1$ and FVC were observed in PONVORY-treated subjects, and were greater than in subjects taking placebo [see Warnings and Precautions (5.3)]. These effects can be reversed with administration of a short acting beta2 agonist.

11.3 Pharmacokinetics

Following ponesimod oral dosing, $C_{max}$ and AUC increased approximately dose-proportionally in the dose-range studied (1-75 mg). Steady-state levels are approximately 2.0 to 2.6-fold greater than with a single dose, and are achieved following 3 days of administration of the maintenance dose of ponesimod.

The pharmacokinetics of ponesimod are similar in healthy subjects and patients with multiple sclerosis, with 25% inter-subject variability across studies.

Absorption

The time to reach maximum plasma concentration of ponesimod is 2-4 hours post-dose. The absolute oral bioavailability of a 10 mg dose is 84%.

Food Effect

Food does not have a clinically relevant effect on ponesimod pharmacokinetics; therefore, PONVORY may be taken with or without food.

Distribution

Following IV administration in healthy subjects, the steady-state volume of distribution of ponesimod is 160 L.

Ponesimod is highly bound to plasma proteins (>99%) and is mainly (78.5%) distributed in the plasma fraction of whole blood. Animal studies show that ponesimod readily crosses the blood-brain-barrier.

Metabolism

Ponesimod is extensively metabolized prior to excretion in humans, though unchanged ponesimod was the main circulating component in plasma. Two inactive circulating metabolites, M12 and M13, have also been identified in human plasma. M13 and M12 are respectively about 20% and 6% of total drug-related exposure. Both metabolites are inactive at S1P receptors at concentrations achieved with recommended doses of ponesimod.

Experiments with human liver preparations indicate that metabolism of ponesimod to M13 occurs primarily through a combination of non-Cytochrome P450 (CYP450) enzymatic activities. Multiple CYP450 (CYP2J2, CYP3A4, CYP3A5, CYP4F3A, and CYP4F12) and non-CYP450 enzymes catalyze the oxidation of ponesimod to M12. Ponesimod also undergoes direct glucuronidation (mainly UGT1A1 and UGT2B7).

Excretion

After a single IV administration. the total clearance of ponesimod is 3.8 L/hour. The elimination half-life after oral administration is approximately 33 hours.

Following a single oral administration of $^{14}$C-ponesimod, 57% to 80% of the dose was recovered in feces (16% as unchanged ponesimod), and 10% to 18% in urine (no unchanged ponesimod).

Specific Populations

Renal Impairment

No dose adjustment is necessary in patients with renal impairment. In adult subjects with moderate or severe renal impairment (estimated creatinine clearance [CrCl], as determined by the Cockroft-Gault, between 30-59 mL/min for moderate and <30 mL/min for severe), there were no significant changes in ponesimod $C_{max}$ and AUC, compared to subjects with normal renal function (CrCl>90 mL/min). The effect of dialysis on the PK of ponesimod has not been studied. Due to the high plasma protein binding (greater than 99%) of ponesimod, dialysis is not expected to alter the total and unbound ponesimod concentration, and no dose adjustments are anticipated based on these considerations.

Hepatic Impairment

In adult subjects with mild, moderate, or severe hepatic impairment (Child-Pugh class A, B and C, respectively), no change in ponesimod $C_m$ax was observed, but ponesimod $AUC_{0-\infty}$ was increased by 1.3-, 2.0-, and 3.1-fold, respectively, compared to healthy subjects [see Use in Specific Populations (8.6)].

Age

Age (range: 17 to 65 years) was not identified to significantly influence the PK of ponesimod in population pharmacokinetics analyses. The effect of age (65 years of age and older) on the pharmacokinetics of ponesimod is unknown [see Use in Specific Populations (8.5)].

Gender

Gender has no clinically significant influence on ponesimod pharmacokinetics.

Race

No clinically relevant pharmacokinetic differences were observed between Japanese and Caucasian subjects.

Drug Interaction Studies

Beta-Blockers

In a drug-drug interaction study. the dose titration regimen of ponesimod [see Dosage and Administration (2.2)] was administered to subjects receiving propranolol (80 mg) once daily at steady state. No significant changes in pharmacokinetics of ponesimod or propranolol were observed. Compared to ponesimod alone, the combination of propranolol and the first dose of ponesimod (2 mg) led to a mean hourly heart rate decrease of 12.4 bpm (90% CI: −15.6 to −9.1). Compared to ponesimod alone, propranolol administered in combination with the first maintenance dose of ponesimod (20 mg) led to a 7.4 bpm (90% CI: −10.9 to −3.9) mean hourly heart rate decrease.

Effect of Other Drugs on Ponesimod

In vitro studies with human liver preparations indicate that metabolism of ponesimod occurs through multiple distinct enzyme systems, including multiple CYP450 (CYP2J2, CYP3A4, CYP3A5, CYP4F3A, and CYP4F12), UGT (mainly UGT1A1 and UGT2B7), and non-CYP450 oxidative enzymes, without major contribution by any single enzyme.

Ponesimod is not a substrate of P-gp, BCRP, OATP1B1, or OATP1B3 transporters. Drugs that are inhibitors of these transporters are unlikely to impact the PK of ponesimod.

In vitro assessments and limited clinical data indicated that concomitant use of strong CYP3A4 and UGT1A1 inducers (e.g., rifampin, phenytoin, carbamazepine) may decrease the systemic exposure of ponesimod [see Drug Interactions (7.5)].

Effect of Ponesimod on Other Drugs

In vitro investigations indicate that at the recommended dose of 20 mg once-daily, ponesimod and its metabolite M13 do not show any clinically relevant drug-drug interaction potential for CYP or UGT enzymes, or transporters.

Oral Contraceptives

Coadministration of ponesimod with an oral hormonal contraceptive (containing 1 mg norethisterone/norethindrone and 35 µg ethinyl estradiol) showed no clinically relevant pharmacokinetic interaction with ponesimod. Therefore, concomitant use of ponesimod is not expected to decrease the efficacy of hormonal contraceptives. No interaction studies have been performed with oral contraceptives containing other progestogens: however, an effect of ponesimod on their exposure is not expected.

12. Nonclinical Toxicology 12.1 Carcinogenesis, Mutagenesis, Impairment of Fertility Carcinogenesis Oral administration of ponesimod to mice (0, 50, 150, or 400 mg/kg/day in males and 30, 100, or 300 mg/kg/day in females) for up to 2 years resulted in incidences in hemangiosarcoma and combined hemangioma and hemangiosarcoma in males at all doses and at the highest dose tested in females. Plasma exposure (AUC) at to lowest dose tested in males (50 mg/kg/day) was approximately 5 times that in humans at the recommended human dose (RHD) of 20 mg.

Oral administration of ponesimod to rats (0, 3, 10, or 30 mg/kg/day in males and 0, 10, 30 or 100 mg/kg/day in females) for up to 2 years did not result in an increase in tumors. Plasma exposure at the highest dose tested in males (30 mg/kg/day) was approximately 4 times that in humans at the recommended human dose (RHD) of 20 mg.

Mutagenesis

Ponesimod was negative in a battery of in vitro (Ames, chromosomal aberration in mammalian cells) and in vivo (micronucleus in rat) assays.

Fertility

In separate studies. oral administration of ponesimod (0, 10, 30, or 100 mg/kg/day) to male and female rats prior to and throughout the mating period and continuing in females to Day 6 of gestation resulted in no effects on fertility. Plasma ponesimod exposures (AUC) at the highest dose tested were approximately 10 (males) and 30 (females) times that in humans at the recommended human dose (RHD) of 20 mg/day.

12.2 Animal Toxicology and/or Pharmacology

Increases in lung weight and histopathology (alveolar histiocytosis, edema) were observed in oral toxicity studies in mice, rats, and dogs. At the higher doses tested in short-term studies, alveolar histiocytosis was associated with lung edema, emphysema, or hyalinosis, and with bronchioloalveolar hyperplasia after cessation of dosing in rats and alveolar histiocytosis and hyalinosis in dogs. Effects tended to be absent or less severe after chronic treatment. These findings are considered secondary to increased vascular permeability caused by $S1P_1$ receptor modulation. The NOAELs for lung findings in the 4-week oral toxicity studies in rats and dogs were associated with plasma exposures (AUC) similar or lower than that expected in humans at the recommended human dose (RHD) of 20 mg/day.

In dogs, coronary arterial lesions (thickening of the vessel wall, hyperplasia/hypertrophy of smooth muscles cells of the tunica media, subendocardial fibrosis) involving the papillary muscle of the left ventricle were observed in oral toxicity studies of 13 to 52 weeks in duration. At the NOAEL (2 mg/kg/day) for these findings, plasma exposures (AUC) were approximately 2 times that expected in humans at the RHD.

13. Clinical Studies

The efficacy of PONVORY was demonstrated in Study 1, a randomized, double-blind, parallel group, active-controlled superiority study in patients with relapsing forms of MS (NCT02425644). Patients were treated for 108 weeks. This study included patients who had an Expanded Disability Status Scale (EDSS) score of 0 to 5.5 at baseline, had experienced at least one relapse within the year prior, or two relapses within the prior 2 years, or who had at least one gadolinium-enhancing (Gd-enhancing) lesion on a brain MRI within the prior 6 months or at baseline. Patients with primary progressive MS were excluded.

Patients were randomized to receive either once daily PONVORY, beginning with a 14-day dose titration [see Dosage and Administration (2.2)] or teriflunomide 14 mg. Neurological evaluations were performed at baseline, every 3 months during the study, and at the time of a suspected relapse. Brain MRI scans were performed at baseline and at Weeks 60 and 108.

The primary endpoint was the annualized relapse rate (ARR) over the study period. Additional outcome measures included: 1) the number of new Gd-enhancing T1 lesions from baseline to Week 108, 2) the number of new or enlarging T2 lesions (without double-counting of lesions) from baseline to Week 108, and 3) the time to 3-month and 6-month confirmed disability progression. A confirmed disability progression was defined as an increase of at least 1.5 in EDSS for patients with a baseline EDSS score of 0, an increase of at least 1.0 in EDSS for patients with a baseline EDSS score of 1.0 to 5.0, or an increase of at least 0.5 in EDSS for patients with a baseline EDSS score at least 5.5, which was confirmed after 3 months and 6 months.

A total of 1133 patients were randomized to either PONVORY (N=567) or teriflunomide 14 mg (N=566); 86.4% of PONVORY-treated patients and 87.5% of teriflunomide 14 mg-treated patients completed the study as per protocol. At baseline, the mean age of patients was 37 years, 97% were White, and 65% were female. The mean disease duration was 7.6 years, the mean number of relapses in the previous year was 1.3, and the mean EDSS score was 2.6; 57% of patients had not received any prior non-steroid treatments for MS. At baseline, 42.6% of patients had one or more Gd-enhancing T1 lesions (mean 2.0) on their baseline MRI scan.

The ARR was statistically significantly lower in patients treated with PONVORY than in patients who received teriflunomide 14 mg. The number of Gd-enhancing T1 lesions and the number of new or enlarging T2 lesions were statistically significantly lower in patients treated with PONVORY than in patients who received teriflunomide 14 mg.

There was no statistically significant difference in the 3-month and 6-month confirmed disability progression outcomes between PONVORY— and teriflunomide 14 mg-treated patients over 108 weeks.

The efficacy results for Study 1 are presented in Table 22.

TABLE 22

Clinical and NMI Endpoints from Study 1

| Endpoints | PONVORY 20 mg N = 567 | Teriflunomide 14 mg N = 566 |
|---|---|---|
| Clinical Endpoints | | |
| Annualized Relapse Rate $^a$ | 0.202 | 0.290 |
| Relative reduction | 30.5% (p = 0.0003) | |
| Percentage of patients without relapse $^b$ | 70.7% | 60.6% |
| Proportion of Patients with 3-month Confirmed Disability Progression $^c$ | 10.8% | 13.2% |
| Hazard Ratio $^d$ | 0.83 (p = 0.29) | |
| MRI Endpoints $^{b,\,f}$ | | |
| Mean number of new or enlarging T2 hyperintense lesions per year | 1.40 | 3.16 |
| Relative reduction | 55.7% (p < 0001) | |
| Mean number of T1 Gd-enhancing lesions per MRI | 0.18 | 0.43 |
| Relative reduction | 58.5% (p < 0001) | |

All analyses are based on the full analysis set (FAS), which includes all randomized patients. N refers to the number of patients included in the FAS, per treatment group.
$^a$ Defined as confirmed relapses per year through the study period (Negative binomial regression model with stratification variables (EDSS ≤ 3.5 versus EDSS > 3.5; not-steroid treatment for MS within last 2 years prior to randomization [Yes/No]) and the number of relapses in the year prior to study entry (<=1, >=2) as marines)
$^b$ Over the study period of approximately 108 weeks
$^c$ Disability progression defined as 1.5-point in EDSS for patients with a baseline EDSS score of 0, 1.0-point increase in EDSS for patients with a baseline EDSS score of 1.0 to 5.0, or 0.5-point increase in EDSS for patients with a baseline EDSS score at least 5.5 confirmed 3 months later. Proportion of patients with 3-month confirmed disability progression refers to Kaplan-Meier estimates at Week 108.
$^d$ Defined as time to 3 months confirmed disability progression through the study period (Stratified Cox proportional hazard model, p-value based on the stratified log rank test)
$^e$ Not statistically significant
$^f$ Cumulative number of combined unique active lesions (CUALs), defined as new or enlarging T2 lesions or Gd-enhancing T1 lesions (without double counting), mean lesions per year were 1.41 on ponesimod 20 mg (N = 539), and 3.16 on teriflunomide 14 mg (N = 536), a relative reduction of 56% (p < 0.0001).

A similar effect of PONVORY on the ARR and secondary MRI outcomes compared to teriflunomide 14 mg was observed in exploratory subgroups defined by age, gender, prior non-steroid therapy for MS, and baseline disease activity.

14. How Supplied/Storage and Handling 14.1 How Supplied

PONVORY™ (ponesimod) tablet is available as round, biconvex, film-coated tablets supplied in the following dosage strengths and package configurations, Tables 23 and 24.

TABLE 23

Starter Pack

| Tablet Strength | Tablet Color | Tablet Size | Tablet Debossing | Pack Size | NDC Code |
|---|---|---|---|---|---|
| 2 mg | White | 5.0 mm | "2" on one side and an arch on the other side. | Child Resistant Starter Pack (14 tablets) | NDC 50458-707-14 |
| 3 mg | Red | 5.0 mm | "3" on one side and an arch on the other side. | | |
| 4 mg | Purple | 5.0 mm | "4" on one side and an arch on the other side. | | |
| 5 mg | Green | 8.6 mm | "5" on one side and an arch and an "A" on the other side. | | |
| 6 mg | White | 8.6 mm | "6" on one side and an arch and an "A" on the other side. | | |

TABLE 23-continued

Starter Pack

| Tablet Strength | Tablet Color | Tablet Size | Tablet Debossing | Pack Size | NDC Code |
|---|---|---|---|---|---|
| 7 mg | Red | 8.6 mm | "7" on one side and an arch and an "A" on the other side. | | |
| 8 mg | Purple | 8.6 mm | "8" on one side and an arch and an "A" on the other side. | | |
| 9 mg | Brown | 8.6 mm | "9" on one side and an arch and an "A" on the other side. | | |
| 10 mg | Orange | 8.6 mm | "10" on one side and an arch and an "A" on the other side. | | |

TABLE 24

Maintenance Dose Bottle

| Tablet Strength | Tablet Color | Tablet Size | Tablet Debossing | Pack Size | NDC Code |
|---|---|---|---|---|---|
| 20 mg | Yellow | 8.6 mm | "20" on one side and an arch and an "A" on the other side. | Bottle of 30 tablets with child-resistant closure. Each bottle contains a desiccant sachet and a polyester coil | NDC 50458-720-30 |

14.2 Storage and Handling

Starter Pack

Store at 20° C. to 25° C. (68° F. to 77° F.); excursions permitted from 15° C. to 30° C. (59° F. to 86° F.) [see USP Controlled Room Temperature].

Store in the original package.

Maintenance Dose Bottle

Store at 20° C. to 25° C. (68° F. to 77° F.); excursions permitted from 15° C. to 30° C. (59° F. to 86° F.) [see USP Controlled Room Temperature].

Store in the original package. Do not discard desiccant. Protect from moisture. Keep out of reach of children.

15. Patient Counseling Information

Advise the patient to read the FDA-approved patient labeling (Medication Guide).

Administration

Tell patients not to discontinue PONVORY without first discussing this with the prescribing healthcare provider. Advise patients to contact their healthcare provider if they accidently take more PONVORY than prescribed.

Instruct patients to administer tablets whole.

Risk of Infections

Inform patients that they may have an increased risk of infections, some of which could be life-threatening, when taking PONVORY and for 1 to 2 weeks after stopping it, and that they should contact their healthcare provider if they develop symptoms of infection [see Warnings and Precautions (5.1)]. Advise patients that the use of some vaccines containing live virus (live attenuated vaccines) should be avoided during treatment with PONVORY, and PONVORY should be paused 1 week prior and until 4 weeks after a planned vaccination. Recommend that patients postpone treatment with PONVORY for at least 1 month after VZV vaccination. Inform patients that prior or concomitant use of drugs that suppress the immune system may increase the risk of infection.

Cardiac Effects

Advise patients that initiation of PONVORY treatment results in transient decrease in heart rate [see Warnings and Precautions (5.2)]. Inform patients that to reduce this effect, dose titration is required. Advise patients that dose titration is also required if 4 or more consecutive daily doses are missed during treatment initiation or maintenance treatment [see Dosage and Administration (2.2, 2.4) and Warnings and Precautions (5.2)]. Inform certain patients with certain preexisting cardiac conditions that they will need to be observed in the doctor's office or other facility for at least 4 hours after the first dose and after re-initiation if treatment is interrupted or discontinued for certain periods [see Dosage and Administration (2.3)].

Respiratory Effects

Advise patients that they should contact their healthcare provider if they experience new onset or worsening of dyspnea [see Warnings and Precautions (5.3)].

Liver Injury

Inform patients that PONVORY may increase liver enzymes. Advise patient that they should contact their healthcare provider if they experience any unexplained nausea, vomiting, abdominal pain, fatigue, anorexia, or jaundice and/or dark urine during treatment [see Warnings and Precautions (5.4)].

Cutaneous Malignancies

Inform patients that the risk of basal cell carcinoma is increased with the use of PONVORY and that cases of melanoma and squamous cell carcinoma have been reported. Advise patients that any suspicious skin lesions should be promptly evaluated. Advise patients to limit exposure to sunlight and ultraviolet light by wearing protective clothing and using a sunscreen with high protection factor [see Warnings and Precautions (5.6)].

Pregnancy and Fetal Risk

Inform patients that, based on animal studies, PONVORY may cause fetal harm. Discuss with women of childbearing age whether they are pregnant, might be pregnant, or are trying to become pregnant. Advise women of childbearing potential of the need for effective contraception during treatment with PONVORY and for one week after stopping PONVORY. Advise a female patient to immediately inform her healthcare provider if she is pregnant or planning to become pregnant [see Warnings and Precautions (5.7)].

Macular Edema

Advise patients that PONVORY may cause macular edema, and that they should contact their healthcare provider if they experience any changes in their vision while taking PONVORY [see Warnings and Precautions (5.8)]. Inform patients with diabetes mellitus or a history of uveitis that their risk of macular edema is increased.

Posterior Reversible Encephalopathy Syndrome

Advise patients to immediately report to their healthcare provider any symptoms involving sudden onset of severe headache, altered mental status, visual disturbances, or seizure. Inform patients that delayed treatment could lead to permanent neurological sequelae [see Warnings and Precautions (5.9)].

Severe Increase in Disability After Stopping PONVORY

Inform patients that severe increase in disability has been reported after discontinuation of another S1P receptor modulator like PONVORY. Advise patients to contact their healthcare provider if they develop worsening symptoms of MS following discontinuation of PONVORY [see Warnings and Precautions (5.11)].

Immune System Effects After Stopping PONVORY

Advise patients that PONVORY continues to have effects, such as lowering effects on peripheral lymphocyte count, for 1 to 2 weeks after the last dose [see Warnings and Precautions (5.12)].

Active ingredient made in Austria.

Manufactured for: Janssen Pharmaceuticals. Inc. Titusville. NJ 08560 © 2021 Janssen Pharmaceutical Companies Medication Guide PONVORY™ (pon-VOR-ee) (ponesimod) tablets, for oral use What is the most important information I should know about PONVORY?

PONVORY may cause serious side effects. including:

Infections. PONVORY can increase your risk of serious infections that can be life-threatening and cause death. PONVORY lowers the number of white blood cells (lymphocytes) in your blood. This will usually go back to normal within 1 to 2 weeks of stopping treatment. Your healthcare provider should review a recent blood test of your white blood cells before you start taking PONVORY.

Call your healthcare provider right away if you have any of these symptoms of an infection during treatment with PONVORY and for 1 to 2 weeks after your last dose of PONVORY:

fever
tiredness
body aches
chills
nausea
vomiting
headache with fever, neck stiffness, sensitivity to light, nausea, or confusion (these may be symptoms of meningitis, an infection of the lining around your brain and spine).

Your healthcare provider may delay starting or may stop your PONVORY treatment if you have an infection.

Slow heart rate (bradycardia or bradyarrhythmia) when you start taking PONVORY. PONVORY can cause your heart rate to slow down, especially after you take your first dose. You should have a test to check the electrical activity of your heart called an electrocardiogram (ECG) before you take your first dose of PONVORY.

Only start your treatment with PONVORY using the Starter Pack. You must use the PONVORY Starter Pack to slowly increase the dose over a 14-day period to help reduce the effect of slowing of your heart rate. It is important to follow the recommended dosing instructions. See "How should I take PONVORY?"

Call your healthcare provider if you experience the following symptoms of slow heart rate:
dizziness
lightheadedness
feeling like your heart is beating slowly or skipping beats
shortness of breath
confusion
chest pain
tiredness.

Follow directions from your healthcare provider when starting PONVORY and when you miss a dose. See "How should I take PONVORY?"

See "What are possible side effects of PONVORY?" for more information about side effects.

What is PONVORY?

PONVORY is a prescription medicine that is used to treat relapsing forms of multiple sclerosis, to include clinically isolated syndrome, relapsing-remitting disease, and active secondary progressive disease, in adults.

It is not known if PONVORY is safe and effective in children.

Do not take PONVORY if you:
have had a heart attack, chest pain called unstable angina, stroke or mini-stroke (transient ischemic attack or TIA), or certain types of heart failure in the last 6 months.
have certain types of heart block or irregular or abnormal heartbeat (arrhythmia), unless you have a pacemaker.

Talk to your healthcare provider before taking PONVORY if you have any of these conditions, or do not know if you have any of these conditions.

Before you take PONVORY, tell your healthcare provider about all of your medical conditions, including if you:
have a fever or infection, or you are unable to fight infections due to a disease or taking medicines that weaken your immune system.
have had chicken pox or have received the vaccine for chicken pox. Your healthcare provider may do a blood test for chicken pox virus. You may need to get the full course of vaccine for chicken pox and then wait 1 month before you start taking PONVORY.
have slow heart rate.
have an irregular or abnormal heartbeat (arrhythmia).
have a history of stroke.
have heart problems, including a heart attack or chest pain.
have breathing problems, including during your sleep (sleep apnea).
have liver problems.
have high blood pressure.
had or now have a type of skin cancer called basal cell carcinoma (BCC), melanoma, or squamous cell carcinoma.
have eye problems, especially an inflammation of the eye called uveitis. have diabetes.
are pregnant or plan to become pregnant. PONVORY may harm your unborn baby. Talk with your healthcare provider if you are pregnant or plan to become pregnant. If you are a woman who can become pregnant, you should use effective birth control during your treatment with PONVORY and for 1 week after you stop taking PONVORY. Talk to your healthcare provider about what method of birth control is right for you during this time. Tell your healthcare provider right away if you do become pregnant while taking PONVORY or within 1 week after you stop taking PONVORY.

are breastfeeding or plan to breastfeed. It is not known if PONVORY passes into your breast milk. Talk to your healthcare provider about the best way to feed your baby if you take PONVORY.

Tell your healthcare provider about all the medicines you take, including prescription medicines, over-the-counter medicines, vitamins, and herbal supplements.

Using PONVORY and other medicines together may affect each other causing serious side effects.

Especially tell your healthcare provider if you take or have taken:
medicines to control your heart rhythm (antiarrhythmics), or blood pressure (antihypertensives), or heart beat (such as calcium channel blockers or beta-blockers).
medicines that affect your immune system, such as alemtuzumab.
medicines such as rifampin, phenytoin, or carbamazepine.

You should not receive live vaccines during treatment with PONVORY, for at least 1 month before taking PONVORY, and for 1 to 2 weeks after you stop taking PONVORY. If you receive a live vaccine, you may get the infection the vaccine was meant to prevent. Vaccines may not work as well when given during treatment with PONVORY.

Talk with your healthcare provider if you are not sure if you take any of these medicines.

Know the medicines you take. Keep a list of your medicines with you to show your healthcare provider and pharmacist when you get a new medicine.

How should I take PONVORY?

You will receive a 14-day starter pack. You must start PONVORY by slowly increasing doses over the first two weeks. Follow the dose schedule in Table 25 below. This may reduce the risk of slowing of the heart rate.

TABLE 25

Dose Schedule

|  | Daily Dose |
| --- | --- |
| Starter Pack Day | |
| Day 1 | 2 mg tablet 1 time a day |
| Day 2 | 2 mg tablet 1 time a day |
| Day 3 | 3 mg tablet 1 time a day |
| Day 4 | 3 mg tablet 1 time a day |
| Day 5 | 4 mg tablet 1 time a day |
| Day 6 | 4 mg tablet 1 time a day |
| Day 7 | 5 mg tablet 1 time a day |
| Day 8 | 6 mg tablet 1 time a day |
| Day 9 | 7 mg tablet 1 time a day |
| Day 10 | 8 mg tablet 1 time a day |
| Day 11 | 9 mg tablet 1 time a day |
| Day 12 | 10 mg tablet 1 time a day |
| Day 13 | 10 mg tablet 1 time a day |
| Day 14 | 10 mg tablet 1 time a day |
| Maintenance | |
| Day 15 and thereafter | 20 mg tablet 1 time a day |

Take PONVORY exactly as your healthcare provider tells you to take it.
Take PONVORY 1 time each day.
Swallow PONVORY tablets whole.
Take PONVORY with or without food.
Do not stop taking PONVORY without talking to your healthcare provider first.
Do not skip a dose.
Start taking PONVORY with a 14-day starter pack.
If you miss taking 1, 2, or 3 tablets in a row of PONVORY in the 14-day starter pack, continue treatment by taking the first dose you missed. Take 1 tablet as soon as you remember. Then, take 1 tablet a day to continue with the starter pack dose as planned.
If you miss taking 1, 2, or 3 tablets in a row of PONVORY while taking the 20 mg maintenance dose, continue treatment with the 20 mg maintenance dose.
If you miss taking 4 or more tablets in a row of PONVORY, while taking the 14-day starter pack or the 20 mg maintenance dose, you need to restart treatment with a new 14-day starter pack. Call your healthcare provider if you miss 4 or more doses of PONVORY. Do not restart PONVORY after stopping it for 4 or more days in a row without talking to your healthcare provider. If you have certain heart conditions, you may need to be monitored by your healthcare provider for at least 4 hours when you take your next dose.
Write down the date you start taking PONVORY so you will know if you miss 4 or more doses in a row.

What are the possible side effects of PONVORY?
PONVORY may cause serious side effects, including:
See "What is the most important information I should know about PONVORY?"
breathing problems. Some people who take PONVORY have shortness of breath. Call your healthcare provider right away if you have new or worsening breathing problems.
liver problems. PONVORY may cause liver problems. Your healthcare provider should do blood tests to check your liver before you start taking PONVORY. Call your healthcare provider right away if you have any of the following symptoms of liver problems:
unexplained nausea
vomiting
stomach (abdominal) pain
tiredness
loss of appetite
yellowing of the whites of your eyes or skin
dark urine.
increased blood pressure. Your healthcare provider should check your blood pressure during treatment with PONVORY.
types of skin cancer called basal cell carcinoma (BCC), melanoma, and squamous cell carcinoma. Certain types of skin cancer have happened with drugs in the same class. Tell your healthcare provider if you have any changes in the appearance of your skin, including changes in a mole, a new darkened area on your skin, a sore that does not heal, or growths on your skin, such as a bump that may be shiny, pearly white, skin-colored, or pink. Your doctor should check your skin for any changes during treatment with PONVORY. Limit the amount of time you spend in sunlight and ultraviolet (UV) light. Wear protective clothing and use a sunscreen with a high sun protection factor.
a problem with your vision called macular edema. Tell your healthcare provider about any changes in your vision. Your healthcare provider should test your vision before you start taking PONVORY and any time you notice vision changes during treatment with PONVORY. Your risk of macular edema is higher if you have diabetes or have had an inflammation of your eye called uveitis.

Call your healthcare provider right away if you have any of the following symptoms:
- blurriness or shadows in the center of your vision
- a blind spot in the center of your vision
- sensitivity to light
- unusually colored (tinted) vision.
- swelling and narrowing of the blood vessels in your brain. A condition called Posterior Reversible Encephalopathy Syndrome (PRES) has happened with drugs in the same class. Symptoms of PRES usually get better when you stop taking PONVORY. However, if left untreated, it may lead to a stroke. Call your healthcare provider right away if you have any of the following symptoms:
  - sudden severe headache
  - sudden confusion
  - sudden loss of vision or other changes in your vision
  - seizure.
- severe worsening of multiple sclerosis (MS) after stopping PONVORY. When PONVORY is stopped, symptoms of MS may return and become worse compared to before or during treatment. Always talk to your healthcare provider before you stop taking PONVORY for any reason. Tell your healthcare provider if you have worsening symptoms of MS after stopping PONVORY.

The most common side effects of PONVORY include:
- upper respiratory tract infections
- elevated liver enzymes (abnormal liver tests)
- high blood pressure.

These are not all of the possible side effects of PONVORY.

For more information, ask your healthcare provider or pharmacist.

Call your healthcare provider for medical advice about side effects. You may report side effects to FDA at 1-800-FDA-1088.

How should I store PONVORY?

Store PONVORY at room temperature between 68° F. to 77° F. (20° C. to 25° C.).

Store PONVORY in the original package.

The bottle of PONVORY contains a desiccant sachet to help keep your medicine dry (protect it from moisture Do not throw away (discard) the desiccant.

Keep PONVORY and all medicines out of the reach of children.

General information about the safe and effective use of PONVORY.

Medicines are sometimes prescribed for purposes other than those listed in a Medication Guide. Do not use PONVORY for conditions for which it was not prescribed. Do not give PONVORY to other people, even if they have the same symptoms that you have. It may harm them.

You can ask your healthcare provider or pharmacist for information about PONVORY that is written for health professionals.

What are the ingredients in PONVORY?
Active ingredient: ponesimod
Inactive Ingredients:
Tablet core: croscarmellose sodium, lactose monohydrate, magnesium stearate, microcrystalline cellulose, povidone K30, silica colloidal anhydrous, and sodium lauryl sulfate.

Tablet coating: ferrosoferric oxide (included in 4 mg, 5 mg, 8 mg, and 9 mg film-coated tablets), Hydroxypropyl methylcellulose 2910, iron oxide red (included in 3 mg, 4 mg, 7 mg, 8 mg, 9 mg, and 10 mg film-coated tablets), iron oxide yellow (included in 3 mg, 5 mg, 7 mg, 9 mg, 10 mg and 20 mg film-coated tablets), lactose monohydrate, polyethylene glycol 3350, titanium dioxide, and triatetin.

Manufactured for: Janssen Pharmaceuticals, Inc., Titusville, NJ 08560

© 2021 Janssen Pharmaceutical Companies

For more information, go to www.ponvory.com or call 1-800-526-7736.

This Medication Guide has been approved by the U.S. Food and Drug Administration Approved: 03/2021

What is claimed:

1. A method for reducing clinical management events before or during treatment of multiple sclerosis in a patient in need thereof, comprising administering ponesimod in an amount and manner that is described in a drug product label for an approved drug product.

2. The method of claim 1, wherein about 20 mg of ponesimod is administered orally once daily.

3. The method of claim 1, wherein the treatment comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by administering 20 mg of ponesimod once daily thereafter.

4. The method of claim 1, wherein the multiple sclerosis is relapsing multiple sclerosis.

5. The method of claim 4, wherein the relapsing multiple sclerosis comprises relapsing-remitting disease, clinically isolated syndrome, or active secondary progressive disease.

6. The method of claim 1, wherein the clinical management event comprises first-dose monitoring, genotyping, an eye exam, drug-drug interactions (DDI), or a liver function test, or combinations thereof.

7. The method of claim 6, wherein the reduction is relative to a patient population at substantially the same level of disease progression receiving a standard of care treatment comprising an S1P receptor modulator other than ponesimod.

8. The method of claim 7, wherein the standard of care treatment comprises fingolimod, siponimod, or ozanimod.

* * * * *